United States Patent
Ookubo et al.

(10) Patent No.: US 11,161,830 B2
(45) Date of Patent: Nov. 2, 2021

(54) 4-PYRIDONE COMPOUND OR SALT THEREOF, AND PHARMACEUTICAL COMPOSITION AND FORMULATION INCLUDING SAME

(71) Applicant: FUJIFILM Corporation, Tokyo (JP)

(72) Inventors: Megumi Ookubo, Ashigarakami-gun (JP); Shinichiro Sekine, Ashigarakami-gun (JP); Tomoyuki Mashiko, Ashigarakami-gun (JP); Hyoei Kawai, Ashigarakami-gun (JP); Hirofumi Fukunaga, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 21 days.

(21) Appl. No.: 16/583,916

(22) Filed: Sep. 26, 2019

(65) Prior Publication Data

US 2020/0017459 A1   Jan. 16, 2020

Related U.S. Application Data

(63) Continuation of application No. PCT/JP2018/013580, filed on Mar. 30, 2018.

(30) Foreign Application Priority Data

Mar. 31, 2017  (JP) .............................. JP2017-069837
Aug. 31, 2017  (JP) .............................. JP2017-166413

(51) Int. Cl.
| | |
|---|---|
| *C07D 417/04* | (2006.01) |
| *A61K 31/4436* | (2006.01) |
| *C07D 309/38* | (2006.01) |
| *A61P 31/20* | (2006.01) |
| *C07D 207/08* | (2006.01) |
| *C07D 207/12* | (2006.01) |
| *C07D 277/82* | (2006.01) |
| *C07D 405/10* | (2006.01) |
| *C07D 409/04* | (2006.01) |
| *C07D 417/12* | (2006.01) |
| *C07D 417/14* | (2006.01) |
| *C07D 498/04* | (2006.01) |

(52) U.S. Cl.
CPC ............ *C07D 309/38* (2013.01); *A61P 31/20* (2018.01); *C07D 207/08* (2013.01); *C07D 207/12* (2013.01); *C07D 277/82* (2013.01); *C07D 405/10* (2013.01); *C07D 409/04* (2013.01); *C07D 417/04* (2013.01); *C07D 417/12* (2013.01); *C07D 417/14* (2013.01); *C07D 498/04* (2013.01)

(58) Field of Classification Search
CPC .............. C07D 417/04; A61K 31/4436; A61K 31/4412; A61P 31/12
USPC ............... 546/270.1; 514/321, 338
See application file for complete search history.

(56) References Cited

U.S. PATENT DOCUMENTS

| | | | |
|---|---|---|---|
| 4,698,352 | A  | 10/1987 | Narita et al. |
| 5,217,972 | A  | 6/1993  | Grohe et al. |
| 6,436,943 | B1 | 8/2002  | Stoltefuss et al. |
| 6,777,420 | B2 | 8/2004  | Zhi et al. |
| 10,308,642 | B2 | 6/2019 | Shimane et al. |
| 2010/0240655 | A1 | 9/2010 | Siegfried et al. |
| 2012/0022255 | A1 | 1/2012 | Fujishita et al. |
| 2012/0041208 | A1 | 2/2012 | Hanselmann et al. |
| 2013/0084346 | A1 | 4/2013 | Wolkenberg et al. |
| 2018/0291011 | A1 | 10/2018 | Shimane et al. |

FOREIGN PATENT DOCUMENTS

| | | |
|---|---|---|
| CN | 1465567 A     | 1/2004 |
| CN | 103992290 A   | 8/2014 |
| JP | 59-080665 A   | 5/1984 |
| JP | S61-246163 A  | 11/1986 |

(Continued)

OTHER PUBLICATIONS

Extended European Search Report dated Jan. 3, 2020 from the European Patent Office in European application No. 18775249.8.

(Continued)

*Primary Examiner* — Charanjit Aulakh

(74) *Attorney, Agent, or Firm* — Sughrue Mion, PLLC

(57) ABSTRACT

An object of the present invention is to provide a compound or a salt thereof having anti-HBV activity, a pharmaceutical composition, an anti-hepatitis B virus agent, a production inhibitor of DNA of a hepatitis B virus, and a production or secretion inhibitor of a hepatitis B surface antigen. According to the present invention, provided are a compound represented by General Formula [1] or a salt thereof:

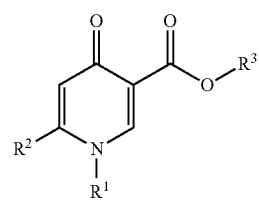

[1]

(in the formula, $R^1$ represents a benzothiazolyl group which may be substituted (in which a carbon atom constituting the 6-membered ring of the benzothiazolyl group of $R^1$ is bonded to the nitrogen atom of the pyridone ring); $R^2$ represents a $C_{2-6}$ alkenyl group which may be substituted, or the like; and $R^3$ represents a hydrogen atom or the like).

16 Claims, No Drawings

(56) References Cited

FOREIGN PATENT DOCUMENTS

| JP | H02-061947 B2 | 12/1990 |
|---|---|---|
| JP | 2002-512233 A | 4/2002 |
| JP | 2010-530374 A | 9/2010 |
| JP | 2013-521285 A | 6/2013 |
| RU | 2011116052 A | 10/2012 |
| WO | 2010/110231 A1 | 9/2010 |
| WO | 2016/128335 A1 | 8/2016 |
| WO | 2017/013046 A1 | 1/2017 |
| WO | 2017/061466 A1 | 4/2017 |

OTHER PUBLICATIONS

Tanaka et al., "Fundamental and Clinical Evaluation of Hepatitis B virus core-related antigen assay", Modern Media, vol. 54, No. 12, pp. 347-352.
International Search Report dated Jun. 12, 2018 in International Application No. PCT/JP2018/013580.
Written Opinion of the International Searching Authority dated Jun. 12, 2018 in International Application No. PCT/JP2018/013580.
International Preliminary Report on Patentability dated Oct. 1, 2019 in International Application No. PCT/JP2018/013580.
Bhattacharya, Debika et al, "Review of Hepatitis B Therapeutics", Clinical Infectious Diseases, vol. 51, No. 10, pp. 1201-1208, Nov. 15, 2010 (15 pages total).
Extended European Search Report dated Apr. 23, 2019 in European Application No. 16853620.9.
International Search Report dated Nov. 1, 2016 in International Application No. PCT/JP2016/079614.
Rajbhandari, Ruma et al, "Treatment of Hepatitis B: A Concise Review", Clinical and Translational Gastroenterology, vol. 7, No. 9, e190, Sep. 1, 2016 (10 pages total).
Zhiliang Lv et al., "Design, Synthesis, and Antihepatitis B Virus Activities of Novel 2-Pyridone Derivatives", Journal of Medicinal Chemistry, 2010, pp. 660-668, vol. 53, No. 2.
Laursen, Jane et al., "Further Exploration of Antimicrobial Ketodihydronicotinic Acid Derivatives by Multiple Parallel Syntheses", Combinatorial Chemistry & High Throughput Screening, vol. 9, No. 9, pp. 663-681, 2006.
Narita, Hirokazu et al., "Pyridonecarboxylic Acids as Antibacterial Agents. I. Synthesis and Structure-Activity Relationship of 1-Aryl-6-(4-dimethylaminophenyl)-4-pyridone-3-carboxylic Acids", Yakugaku Zasshi, vol. 106, No. 9, pp. 775-781, 1986.
Office Action dated Jul. 31, 2018 in U.S. Appl. No. 15/765,011.
Notice of Allowance dated Jan. 3, 2019 in U.S. Appl. No. 15/765,011.
Office Action dated Apr. 10, 2020, from the Federal Service for Intellectual Property of Russia in Russian Application No. 2019130519/04.
Office Action dated May 22, 2020 from Indian Patent Office in Indian Application No. 201947039566.
Office Action dated Oct. 6, 2020, issued by the Japanese Patent Office in Japanese application No. 2019-510237.
Office Action dated Feb. 3, 2021, from the Intellectual Property of India in Indian application No. 201947039566.

4-PYRIDONE COMPOUND OR SALT THEREOF, AND PHARMACEUTICAL COMPOSITION AND FORMULATION INCLUDING SAME

CROSS-REFERENCE TO RELATED APPLICATIONS

This application is a Continuation of PCT International Application No. PCT/JP2018/013580 filed on Mar. 30, 2018, which claims priority under 35 U.S.C § 119(a) to Japanese Patent Application No. 2017-069837 filed on Mar. 31, 2017 and Japanese Patent Application No. 2017-166413 filed on Aug. 31, 2017. Each of the above application(s) is hereby expressly incorporated by reference, in its entirety, into the present application.

BACKGROUND OF THE INVENTION

1. Field of the Invention

The present invention relates to a 4-pyridone compound or a salt thereof having anti-hepatitis B virus activity, a pharmaceutical composition, an anti-hepatitis B virus agent, a production inhibitor of DNA of a hepatitis B virus, and a production or secretion inhibitor of a hepatitis B surface antigen.

2. Description of the Related Art

A hepatitis B virus (HBV) is a virus belonging to a Hepadnavirus genus and is a spherical DNA virus having a diameter of about 42 nm. The virus itself is a DNA virus including a core with a diameter of 27 nm, which includes an envelope, an incomplete double-stranded DNA, a DNA polymerase, a reverse transcriptase, and the like, and is called a Dane particle. The virus forms a double structure, and has an external side including an HBs antigen (hepatitis B surface antigen, HBsAg) and an inner side including an HBc antigen (hepatitis B core antigen, HBcAg) and gene DNA (Non-Patent Document 1).

The HBs antigen is present as a hollow particle, a small spherical particle, or a rod particle, in addition to Dane particle. The DNA includes four types of transcriptional open reading frames (ORE) of a pre-S/S gene region, a P gene region, an X gene region, and a pre-C/C gene region. The core promoter of the X gene region and the precore region of the C gene region are involved in the production of constitutive protein for an HBe antigen (hepatitis B envelope antigen, HBeAg), and an HBe antigen-constituting protein is not produced due to point mutation of the region, whereby it becomes the HBe antigen negative.

In a case where HBV invades a hepatocyte, a viral gene moves into the nucleus of the hepatocyte, and the incomplete circular double-stranded DNA is converted to a covalently closed circular DNA (cccDNA). In a chronic infection state with HBV, 5 to 50 replicative intermediate cccDNAs exist in one hepatocyte as a minichromosome. Four kinds of mRNAs are transcribed from cccDNA in the nucleus of the hepatocyte, from which an HBs antigen that is a structural protein, an HBc antigen, an HBe antigen, a polymerase that includes a reverse transcriptase, and an X protein are translated. One of the mRNAs is incorporated as a pregenomic RNA into a core particle, a minus-strand DNA is synthesized by the function of a reverse transcriptase, and then a plus-strand DNA is synthesized, and thus, becomes an incomplete circular double-stranded DNA. Further, the DNA is covered with an envelope formed with the HBs antigen to become a virus particle (Dane particle), which is discharged into the blood. In a proliferation route other than the discharge of the Dane particle into the blood, a hollow particle (particle having no nucleus of DNA) including the HBs antigen, the HBc antigen, and the p22cr antigen that are each translated by mRNA, the HBe antigen that passes through the hepatocyte membrane, and the like are discharged and secreted into the blood in large amounts in a route different from that of the discharge of the Dane particle into the blood. This action is considered an action for an escape from an attack of a host immune mechanism in HBV infection. The HBe antigen, the HBc antigen, and the p22cr antigen can be measured as an HBcr antigen (hepatitis B core-related antigen, HBcrAg), and has been used as a marker of viral replication.

Hepatitis B is one type of viral hepatitis which develops by the infection with a hepatitis B virus, and it is thought that about 350 million people worldwide are infected with hepatitis B.

For the treatment of Hepatitis B, interferon, nucleic acid analogs, and the like are used, but their effects are not sufficient.

On the other hand, a pyridone-carboxylic acid derivative having antibacterial activity is known (for example, Patent Documents 1 and 2). However, it is not known that the pyridone-carboxylic acid derivatives described in Patent Documents 1 and 2 have antiviral activity.

PATENT DOCUMENTS

Patent Document 1: JP 1990-061947B (JP-H02-061947B)
Patent Document 2: JP 1986-246163A (JP-S61-246163A)

Non-Patent Document

Non-Patent Document 1: Tanaka et al., Modern Media Vol. 54, No. 12, pp. 347 to 352

SUMMARY OF THE INVENTION

An object of the present invention is to provide a compound or a salt thereof having anti-HBV activity, a pharmaceutical composition, an anti-hepatitis B virus agent, a production inhibitor of DNA of a hepatitis B virus, and a production or secretion inhibitor of a hepatitis B surface antigen.

The present inventors have conducted extensive studies on the objects, and as a result, a compound represented by General Formula [1] or a salt thereof has excellent anti-HBV activity, thereby leading to completion of the present invention.

That is, the present invention provides the following aspects.

<1> A compound represented by General Formula [1] or a salt thereof:

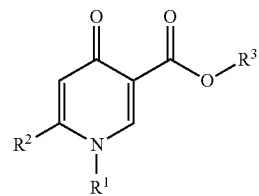

[1]

in the formula, $R^1$ represents a benzothiazolyl group which may be substituted (in which a carbon atom constituting the 6-membered ring of the benzothiazolyl group of $R^1$ is bonded to the nitrogen atom of the pyridone ring);

$R^2$ represents a $C_{2-6}$ alkenyl group which may be substituted, a $C_{2-6}$ alkynyl group which may be substituted, a $C_{3-8}$ cycloalkyl group which may be substituted, an aryl group which may be substituted, or a heterocyclic group which may be substituted; and $R^3$ represents a hydrogen atom or a carboxy-protecting group.

<2> The compound or a salt thereof as described in <1>, in which the compound is a compound represented by General Formula [1-1]:

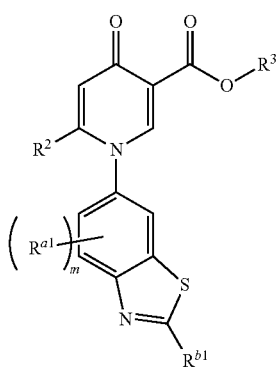

[1-1]

in the formula, m $R^{a1}$'s are each independently the same as or different from each other, and represent a halogen atom, a cyano group, a nitro group, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, a carbamoyl group which may be substituted, a sulfamoyl group which may be substituted, or a carboxyl group which may be protected;

$R^{b1}$ represents a hydrogen atom, a halogen atom, a cyano group, a nitro group, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, an acylamino group which may be substituted, a carbamoyl group which may be substituted, a sulfamoyl group which may be substituted, a heterocyclic group which may be substituted, or a carboxyl group which may be protected;

$R^2$ represents a $C_{2-6}$ alkenyl group which may be substituted, a $C_{2-6}$ alkynyl group which may be substituted, a $C_{3-8}$ cycloalkyl group which may be substituted, an aryl group which may be substituted, or a heterocyclic group which may be substituted;

$R^3$ represents a hydrogen atom or a carboxy-protecting group; and m represents an integer of 0 to 3.

<3> The compound or a salt thereof as described in <2>, in which m $R^{a1}$'s are each independently the same as or different from each other, and are each a halogen atom, a $C_{1-6}$ alkyl group which may be substituted, or a $C_{1-6}$ alkoxy group which may be substituted; and m is an integer of 0 or 1.

<4> The compound or a salt thereof as described in <2> or <3>, in which $R^{b1}$ is a hydrogen atom, a halogen atom, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, or a heterocyclic group which may be substituted.

<5> The compound or a salt thereof as described in any one of <1> to <4>, in which $R^2$ is a phenyl group which may be substituted, a thienyl group which may be substituted, a thiazolyl group which may be substituted, or a benzoxazinyl group which may be substituted.

<6> The compound or a salt thereof as described in any one of <1> to <4>, in which $R^2$ is a phenyl group which may have one or more substituents selected from a substituent group $A_1$, a thienyl group which may have one or more substituents selected from the substituent group $A_1$, a thiazolyl group which may have one or more substituents selected from the substituent group $A_1$, or a benzoxazinyl group represented by General Formula [2]:

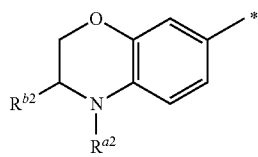

[2]

in the formula, $R^{a2}$ represents a hydrogen atom, a $C_{1-6}$ alkyl group which may be substituted, an acyl group which may be substituted, a $C_{1-6}$ alkylsulfonyl group which may be substituted, or an arylsulfonyl group which may be substituted;

$R^{b2}$ represents a hydrogen atom, a $C_{1-6}$ alkyl group which may be substituted, an aryl group which may be substituted, an acyl group which may be substituted, a carbamoyl group which may be substituted, a sulfamoyl group which may be substituted, a heterocyclic group which may be substituted, or a carboxyl group which may be protected; or $R^{a2}$ and $R^{b2}$ may be combined with an atom to which they are bonded to form a 5-membered heterocycle which may be substituted or a 6-membered heterocycle which may be substituted; and * represents a bonding position, in which the substituent group $A_1$ consists of groups represented by:

a halogen atom, a cyano group, a nitro group, a $C_{1-6}$ alkyl group which may have one or more substituents selected from the substituent group $A_2$, an aryl group which may have one or more substituents selected from the substituent group $A_2$, a $C_{1-6}$ alkoxy group which may have one or more substituents selected from the substituent group $A_2$, a $C_{1-6}$ alkylamino group which may have one or more substituents selected from the substituent group $A_2$, a di($C_{1-6}$ alkyl)amino group which may have one or more substituents selected from the substituent group $A_2$, a carbamoyl group which may have one or more substituents selected from the substituent group $A_2$, a sulfamoyl group which may have one or more substituents selected from the substituent group $A_2$, a heterocyclic group which may have one or more substituents selected from the substituent group $A_2$, and
a carboxyl group which may be protected;
the substituent group $A_2$ consists of groups represented by:
a halogen atom,
a cyano group,
a nitro group,
a $C_{1-6}$ alkyl group which may have one or more substituents selected from the substituent group $A_3$,
an aryl group which may have one or more substituents selected from the substituent group $A_3$,
a $C_{1-6}$ alkoxy group which may have one or more substituents selected from the substituent group $A_3$,
a $C_{1-6}$ alkylamino group which may have one or more substituents selected from the substituent group $A_3$,
a di($C_{1-6}$ alkyl)amino group which may have one or more substituents selected from the substituent group $A_3$,
an acylamino group which may have one or more substituents selected from the substituent group $A_3$,
a carbamoyl group which may have one or more substituents selected from the substituent group $A_3$,
a sulfamoyl group which may have one or more substituents selected from the substituent group $A_3$,
a heterocyclic group which may have one or more substituents selected from the substituent group $A_3$, and
a carboxyl group which may be protected;
the substituent group $A_3$ consists of groups represented by:
a halogen atom,
a cyano group,
a nitro group,
a $C_{1-6}$ alkyl group which may have one or more substituents selected from the substituent group $A_4$,
an aryl group which may have one or more substituents selected from the substituent group $A_4$,
a $C_{1-6}$ alkoxy group which may have one or more substituents selected from the substituent group $A_4$,
a $C_{1-6}$ alkylamino group which may have one or more substituents selected from the substituent group $A_4$,
a di($C_{1-6}$ alkyl)amino group which may have one or more substituents selected from the substituent group $A_4$,
a carbamoyl group which may have one or more substituents selected from the substituent group $A_4$,
a sulfamoyl group which may have one or more substituents selected from the substituent group $A_4$,
a heterocyclic group which may have one or more substituents selected from the substituent group $A_4$, and
a carboxyl group which may be protected; and
the substituent group $A_4$ consists of groups represented by:
a halogen atom,
a cyano group,
a nitro group,
a $C_{1-6}$ alkyl group,
an aryl group,
a $C_{1-6}$ alkoxy group,
a $C_{1-6}$ alkylamino group,
a di($C_{1-6}$ alkyl)amino group,
a carbamoyl group,
a sulfamoyl group,
a heterocyclic group, and
a carboxyl group.
<7> The compound or a salt thereof as described in <6>, in which the substituent group $A_1$ is:
a halogen atom,
a cyano group, a $C_{1-6}$ alkyl group which may have one or more substituents selected from the substituent group $A_2$,
a $C_{1-6}$ alkoxy group which may have one or more substituents selected from the substituent group $A_2$,
a $C_{1-6}$ alkylamino group which may have one or more substituents selected from the substituent group $A_2$,
a di($C_{1-6}$ alkyl)amino group which may have one or more substituents selected from the substituent group $A_2$, or
a heterocyclic group which may have one or more substituents selected from the substituent group $A_2$;
the substituent group $A_2$ is:
a $C_{1-6}$ alkoxy group which may have one or more substituents selected from the substituent group $A_3$,
an acylamino group which may have one or more substituents selected from the substituent group $A_3$, or
a carbamoyl group which may have one or more substituents selected from the substituent group $A_3$;
the substituent group $A_3$ is:
a $C_{1-6}$ alkyl group which may have one or more substituents selected from the substituent group $A_4$,
an aryl group which may have one or more substituents selected from the substituent group $A_4$, or
a $C_{1-6}$ alkoxy group which may have one or more substituents selected from the substituent group $A_4$; and
the substituent group $A_4$ is:
a halogen atom,
a cyano group, or
a $C_{1-6}$ alkyl group.
<8> The compound or a salt thereof as described in <6>, in which the substituent group $A_1$ is:
a halogen atom,
a cyano group,
a nitro group,
a $C_{1-6}$ alkyl group which may have one or more substituents selected from the substituent group $A_2$,
an aryl group which may have one or more substituents selected from the substituent group $A_2$,
a $C_{1-6}$ alkoxy group which may have one or more substituents selected from the substituent group $A_2$,
a $C_{1-6}$ alkylamino group which may have one or more substituents selected from the substituent group $A_2$,
a di($C_{1-6}$ alkyl)amino group which may have one or more substituents selected from the substituent group $A_2$,
a carbamoyl group which may have one or more substituents selected from the substituent group $A_2$,
a sulfamoyl group which may have one or more substituents selected from the substituent group $A_2$,
a heterocyclic group which may have one or more substituents selected from the substituent group $A_2$, or
a carboxyl group which may be protected; and
the substituent group $A_2$ is:
a halogen atom,
a cyano group,
a nitro group,
a $C_{1-6}$ alkyl group,
an aryl group,
a $C_{1-6}$ alkoxy group,
a $C_{1-6}$ alkylamino group,
a di($C_{1-6}$ alkyl)amino group,
a carbamoyl group,
a sulfamoyl group,
a heterocyclic group, or
a carboxyl group.
<9> The compound or a salt thereof as described in <6>, in which the substituent group $A_1$ is:
a halogen atom,
a cyano group, a nitro group,
a $C_{1-6}$ alkyl group,
an aryl group,
a $C_{1-6}$ alkoxy group,
a $C_{1-6}$ alkylamino group,
a di($C_{1-6}$ alkyl)amino group,
a carbamoyl group,
a sulfamoyl group,
a heterocyclic group, or
a carboxyl group.

<10> The compound or a salt thereof as described in <6>, in which $R^{a2}$ is a hydrogen atom or a $C_{1-6}$ alkyl group which may be substituted;
$R^{b2}$ is a hydrogen atom; or
$R^{a2}$ and $R^{b2}$ may be combined with an atom to which they are bonded to form a 5-membered heterocycle which may be substituted.

<11> A pharmaceutical composition comprising:
the compound or a salt thereof as described in any one of <1> to <10>.

<12> An anti-hepatitis B virus agent comprising:
the compound or a salt thereof as described in any one of <1> to <10>.

<13> A production inhibitor of DNA of a hepatitis B virus (also described as HBV) comprising:
the compound or a salt thereof as described in any one of <1> to <10>.

<14> A production or secretion inhibitor of a hepatitis B surface antigen (also described as an HBs antigen or HBsAg) comprising:
the compound or a salt thereof as described in any one of <1> to <10>.

The present invention further provides the following aspects.

<a> The compound or a salt thereof as described in any one of <1> to <10> for use in treatment or prevention of HBV infection.

<b> Use of the compound or a salt thereof as described in any one of <1> to <10> for treatment or prevention of HBV infection.

<c> Use of the compound or a salt thereof as described in any one of <1> to <10> in production of a pharmaceutical for treatment or prevention of HBV infection.

<d> A method for treating or preventing HBV infection, comprising:
an effective amount of the compound or a salt thereof as described in any one of <1> to <10> to a subject.

<e> The compound or a salt thereof as described in any one of <1> to <10> for inhibiting the production or secretion of HBsAg.

<f> The compound or a salt thereof as described in any one of <1> to <10> for inhibiting the production of DNA of HBV.

<g> An therapeutic agent for a disease involving HBV infection, comprising the compound or a salt thereof as described in any one of <1> to <10>.

<h> A method for treating or preventing HBV infection, comprising:
administering the compound or a salt thereof as described in any one of <1> to <10> to a subject.

<i> A therapeutic method for a disease involving HBV infection, comprising:
administering the compound or a salt thereof as described in any one of <1> to <10> to a subject.

<j> A method for inhibiting the production or secretion of HBsAg, comprising:
administering the compound or a salt thereof as described in any one of <1> to <10> to a subject.

<k> A method for inhibiting the production of DNA of HBV, comprising:
administering the compound or a salt thereof as described in any one of <1> to <10> to a subject.

The compound represented by General Formula [1] or a salt thereof of an embodiment of the present invention has excellent anti-HBV activity and is useful as an anti-hepatitis B virus agent.

DESCRIPTION OF THE PREFERRED EMBODIMENTS

The present invention will be described in detail.

In the present invention, % is % by mass unless otherwise specified.

In the present invention, the terms have the following definitions, respectively, unless otherwise specified.

A halogen atom means a fluorine atom, a chlorine atom, a bromine atom, or an iodine atom.

A $C_{1-3}$ alkyl group means a methyl, ethyl, propyl, or isopropyl group.

A $C_{1-6}$ alkyl group means a linear or branched $C_{1-6}$ alkyl group such as methyl, ethyl, propyl, isopropyl, butyl, sec-butyl, isobutyl, tert-butyl, pentyl, isopentyl, and hexyl groups.

A $C_{2-6}$ alkenyl group means a linear or branched $C_{2-6}$ alkenyl group such as vinyl, allyl, propenyl, isopropenyl, butenyl, isobutenyl, 1,3-butadienyl, pentenyl, and hexenyl groups.

A $C_{2-6}$ alkynyl group means a linear or branched $C_{2-6}$ alkynyl group such as ethynyl, propynyl, butynyl, pentynyl, and hexynyl groups.

A $C_{3-8}$ cycloalkyl group means a $C_{3-8}$ cycloalkyl group such as cyclopropyl, cyclobutyl, cyclopentyl, and cyclohexyl groups.

An aryl group means a $C_{6-18}$ aryl group such as phenyl, tolyl, and naphthyl groups.

An aryl $C_{1-6}$ alkyl group means an aryl $C_{1-6}$ alkyl group such as benzyl, diphenylmethyl, trytyl, phenethyl, and naphthylmethyl groups.

A $C_{1-3}$ alkoxy group means a methoxy, ethoxy, propoxy, or isopropoxy group.

A $C_{1-6}$ alkoxy group means a linear or branched $C_{1-6}$ alkoxy group such as methoxy, ethoxy, propoxy, isopropoxy, butoxy, isobutoxy, sec-butoxy, tert-butoxy, pentyloxy, and hexyloxy groups.

A $C_{1-6}$ alkoxy $C_{1-6}$ alkyl group means a $C_{1-6}$ alkoxy $C_{1-6}$ alkyl group such as methoxymethyl, 2-methoxyethyl, and 1-ethoxyethyl groups.

An aryl $C_{1-6}$ alkoxy $C_{1-6}$ alkyl group means an aryl $C_{1-6}$ alkoxy $C_{1-6}$ alkyl group such as benzyloxymethyl and phenethyloxymethyl groups.

A $C_{2-6}$ alkanoyl group means a linear, branched, or cyclic $C_{2-6}$ alkanoyl group such as acetyl, propionyl, valeryl, isovaleryl, pivaloyl, cyclopropylcarbonyl, cyclobutylcarbonyl, and cyclopentylcarbonyl groups.

An aroyl group means a $C_{6-18}$ arylcarbonyl group such as benzoyl, toluoyl, and naphthoyl groups.

A heterocyclic carbonyl group means a nicotinoyl, thenoyl, pyrrolidinocarbonyl, or furoyl group, or the like.

An acyl group means a formyl group, a $C_{2-6}$ alkanoyl group, an aroyl group, a heterocyclic carbonyl group, or the like.

A $C_{1-6}$ alkylsulfonyl group means a $C_{1-6}$ alkylsulfonyl group such as methylsulfonyl, ethylsulfonyl, and propylsulfonyl groups.

An arylsulfonyl group means a $C_{6-18}$ arylsulfonyl group such as benzenesulfonyl, p-toluenesulfonyl, and naphthalenesulfonyl groups.

A $C_{1-6}$ alkylsulfonyloxy group means a $C_{1-6}$ alkylsulfonyloxy group such as methylsulfonyloxy, ethylsulfonyloxy, and propylsulfonyloxy groups.

An arylsulfonyloxy group means a $C_{6-18}$ arylsulfonyloxy group such as benzenesulfonyloxy, p-toluenesulfonyloxy, and naphthalenesulfonyloxy groups.

A $C_{1-3}$ alkylamino group means a methylamino, ethylamino, propylamine, or isopropylamino group.

A $C_{1-6}$ alkylamino group means a linear or branched $C_{1-6}$ alkylamino group such as methylamino, ethylamino, propylamino, isopropylamino, butylamino, sec-butylamino, tert-butylamino, pentylamine, and hexylamino groups.

A di($C_{1-3}$ alkyl)amino group means a linear or branched di($C_{1-3}$ alkyl)amino group such as dimethylamino, diethylamino, dipropylamino, diisopropylamino, N-ethyl-N-methylamino, and N-methyl-N-propylamino groups.

A di($C_{1-6}$ alkyl)amino group means a linear or branched di($C_{1-6}$ alkyl)amino group such as dimethylamino, diethylamino, dipropylamino, diisopropylamino, dibutylamino, di(tert-butyl)amino, dipentylamino, dihexylamino, N-ethyl-N-methylamino, and N-methyl-N-propylamino groups.

An arylamino group means a $C_{6-18}$ arylamino group such as phenylamino, p-tolylamino, and 2-naphthylamino groups.

An acylamino group means an acyl group-substituted amino, $C_{1-6}$ alkylamino, or arylamino group such as formylamino, acetylamino, propionylamino, cyclopropylcarbonylamino, pivalolyamino, benzoylamino, toluylamino, naphthoylamino, proylamino, thenoylamino, pyrrolindinyl-carbonylamino, piperidinylcarbonylamino, piperazinylcarbonylamino, morpholinylcarbonylamino, pyridinylcarbonylamino, pyrimidinylcarbonylamino, N-formyl-N-methylamino, N-acetyl-N-methylamino, N-acetyl-N-ethylamino, N-benzoyl-N-methylamino, N-methyl-N-pyridinylcarbonylamino, N-methyl-N-pyrimidinylcarbonylamino, N-formyl-N-phenylamino, and N-acetyl-N-phenylamino groups.

A monocyclic nitrogen-containing heterocyclic group means a monocyclic nitrogen-containing heterocyclic group that includes only a nitrogen atom as a heteroatom forming a ring, such as azepanyl, 1,4-diazepanyl, azetidinyl, pyrrolindinyrl, pyrrolinyl, pyrrolyl, piperidyl, tetrahydropyridyl, pyridyl, homopiperidinyl, octahydroazocinyl, imidazolindinyl, imidazolinyl, imidazolyl, pyrazolindinyl, pyrazolinyl, pyrazolyl, piperazinyl, pyrazinyl, pyridazinyl, pyrimidinyl, homopiperazinyl, triazolyl and tetrazolyl groups.

A monocyclic oxygen-containing heterocyclic group means a tetrahydrofuranyl, furanyl, tetrahydropyranyl, dihydropyranyl, or pyranyl group.

A monocyclic sulfur-containing heterocyclic group means a thienyl group.

A monocyclic nitrogen-oxygen-containing heterocyclic group means a monocyclic nitrogen-oxygen-containing heterocyclic group that includes only a nitrogen atom and an oxygen atom as a heteroatom forming a ring, such as oxazolyl, isoxazolyl, oxadiazolyl, and morpholinyl groups.

A monocyclic nitrogen sulfur-containing heterocyclic group means a monocyclic nitrogen-sulfur-containing heterocyclic group that includes only a nitrogen atom and a sulfur atom as a heteroatom forming a ring, such as thiazolyl, isothiazolyl, thiadiazolyl, thiomorpholinyl, 1-oxidethiomorpholinyl, and 1,1-dioxidethiomorpholinyl.

A monocyclic heterocyclic group means a monocyclic nitrogen-containing heterocyclic group, a monocyclic oxygen-containing heterocyclic group, a monocyclic sulfur-containing heterocyclic group, a monocyclic nitrogen-oxygen-containing heterocyclic group, or a monocyclic nitrogen-sulfur-containing heterocyclic group.

A bicyclic nitrogen-containing heterocyclic group means a bicyclic nitrogen-containing heterocyclic group that includes only a nitrogen atom as a heteroatom forming a ring, such as indolinyl, indolyl, isoindolinyl, isoindolyl, pyrrolopyridinyl, indazolyl, benzimidazolyl, benzotriazolyl, tetrahydroquinolinyl, dihydroquinolinyl, quinolinyl, tetrahydroisoquinolinyl, decahydroisoquinolinyl, isoquinolinyl, dihydroquinazolinyl, cinnolinyl, phthalazinyl, quinazolinyl, dihydroquinoxalinyl, quinoxalinyl, naphthylidinyl, purinyl, pteridinyl, and quinuclidinyl groups.

A bicyclic oxygen-containing heterocyclic group means a bicyclic oxygen-containing heterocyclic group that includes only an oxygen atom as a heteroatom forming a ring, such as a 2,3-dihydrobenzofuranyl, benzofiranyl, isobenzofuranyl, chromanyl, chromenyl, isochromanyl, 1,3-benzodioxolyl, 1,3-benzodioxanyl, and 1,4-benzodioxanyl groups.

A bicyclic sulfur-containing heterocyclic group means a bicyclic sulfur-containing heterocyclic group that includes only a sulfur atom as a heteroatom forming a ring, such as 2,3-dihydrobenzothienyl and benzothienyl groups.

A bicyclic nitrogen-oxygen-containing heterocyclic group means a bicyclic nitrogen-oxygen-containing heterocyclic group that includes only a nitrogen atom and an oxygen atom as a heteroatom forming a ring, such as benzoxazolyl, benzisoxazolyl, benzoxadiazolyl, benzomorpholinyl, dihydropyranopyridyl, dihydrodioxinopyridyl, and dihydropyridooxazinyl groups.

A bicyclic nitrogen-sulfur-containing heterocyclic group means a bicyclic nitrogen-sulfur-containing heterocyclic group that includes a nitrogen atom and a sulfur atom as a heteroatom forming a ring, such as dihydrobenzothiazolyl, benzothiazolyl, benzoisothiazolyl, and benzothiadiazolyl.

A bicyclic heterocyclic group means a bicyclic nitrogen-containing heterocyclic group, a bicyclic oxygen-containing heterocyclic group, a bicyclic sulfur-containing heterocyclic group, a bicyclic nitrogen-oxygen-containing heterocyclic group, or a bicyclic nitrogen-sulfur-containing heterocyclic group.

A spirocyclic heterocyclic group means a spirocyclic heterocyclic group that includes one or more nitrogen atoms, oxygen atoms, or sulfur atoms, such as 2,6-diazaspiro[3.3]heptyl, 2,7-diazaspiro[3.5]nonyl, 2-oxa-6-azaspiro[3.3]heptyl, 1,4-dioxaspiro[4.5]decyl, 1-oxa-8-azaspiro[4.5]decyl, 1-thia-8-azaspiro[4.5]decyl, 6-oxa-6-azaspiro[3.3]heptyl, and 2-oxa-5-azaspiro[3.4]octyl groups.

A heterocyclic group means a monocyclic heterocyclic group, a bicyclic heterocyclic group, a spirocyclic heterocyclic group, or the like.

Substituent group α: a halogen atom, a nitro group, a cyano group, a $C_{1-6}$ alkyl group which may be substituted with one or more groups selected from the substituent group β, an aryl group which may be substituted with one or more groups selected from the substituent group β, a $C_{1-6}$ alkoxy group which may be substituted with one or more groups selected from the substituent group β, a $C_{1-6}$ alkylamino group which may be substituted with one or more groups selected from the substituent group β, a di($C_{1-6}$ alkyl)amino group which may be substituted with one or more groups selected from the substituent group β, a heterocyclic group which may be substituted with one or more groups selected from the substituent group β, and an oxo group which may be substituted with one or more groups selected from the substituent group β.

Substituent group β: a halogen atom, a nitro group, a cyano group, a $C_{1-6}$ alkyl group, aryl group, a $C_{1-6}$ alkoxy group, a $C_{1-6}$ alkylamino group, a di($C_{1-6}$ alkyl)amino group, a heterocyclic group, and an oxo group.

A carboxy protective group includes all of the groups that can be used as general protective groups for a carboxyl group, and examples thereof include the groups described in Greene's Protective Groups in Organic Synthesis, 5$^{th}$ edition, pp, 686 to 836, 2014, John Wiley & Sons, INC. Specific examples thereof include a $C_{1-6}$ alkyl group, an aryl $C_{1-6}$ alkyl group, a $C_{1-6}$ alkoxy $C_{1-6}$ alkyl group, and an aryl $C_{1-6}$ alkoxy $C_{1-6}$ alkyl group. These groups may be substituted with one or more groups selected from the substituent group α.

Examples of the leaving group include a halogen atom, a $C_{1-6}$ alkylsulfonyloxy group, and an arylsulfonyloxy group. The $C_{1-6}$ alkylsulfonyloxy group and the arylsulfonyloxy group may be substituted with one or more groups selected from the substituent group α.

Examples of the alcohols include methanol, ethanol, propanol, 2-propanol, butanol, and 2-methyl-2-propanol.

Examples of the ethers include diethyl ether, diisopropyl ether, dioxane, tetrahydrofuran, anisole, ethylene glycol dimethyl ether, diethylene glycol dimethyl ether, and diethylene glycol diethyl ether.

Examples of the aromatic hydrocarbons include benzene, toluene, and xylene.

In the compound represented by General Formula [1] for use in the present invention, preferred examples of the compound include the following compounds.

$R^1$ is a benzothiazolyl group which may be substituted. Here, a carbon atom constituting the 6-membered ring of the benzothiazolyl group of $R^1$ is bonded to the nitrogen atom of the pyridone ring.

The benzothiazolyl group of $R^1$ may be substituted with one or more groups selected from substituent group $A_1$.

The compound represented by General Formula [1] is preferably a compound represented by General Formula [1-1]:

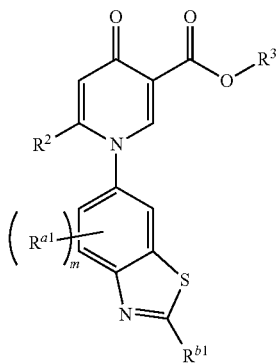

[1-1]

(in the formula, $R^{a1}$, $R^{b1}$, $R^2$, $R^3$, and m have the same definitions.)

m $R^{a1}$'s are each independently the same as or different from each other, and are each a halogen atom, a cyano group, a nitro group, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, a carbamoyl group which may be substituted, a sulfamoyl group which may be substituted, or a carboxyl group which may be protected.

The $C_{1-6}$ alkyl group, the $C_{1-6}$ alkoxy group, the $C_{1-6}$ alkylamino group, the di($C_{1-6}$ alkyl)amino group, the carbamoyl group, and the sulfamoyl group of $R^{a1}$ may be substituted with one or more groups selected from substituent group $A_1$.

The compound in which $R^{a1}$ is a halogen atom, a $C_{1-6}$ alkyl group which may be substituted, or a $C1_{-6}$ alkoxy group which may be substituted is preferable.

The compound in which $R^{a1}$ is a fluorine atom, a chlorine atom, a $C_{1-3}$ alkyl group which may be substituted, or a $C_{1-3}$ alkoxy group which may be substituted is more preferable, and the compound in which $R^{a1}$ is a methyl group is still more preferable.

$R^{b1}$ is a hydrogen atom, a halogen atom, a cyano group, a nitro group, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, an acylamino group which may be substituted, a carbamoyl group which may be substituted, a sulfamoyl group which may be substituted, a heterocyclic group which may be substituted, or a carboxyl group which may be protected.

Each of the $C_{1-6}$ alkyl group, the $C_{1-6}$ alkoxy group, the $C_{1-6}$ alkylamino group, the di($C_{1-6}$ alkyl)amino group, the acylamino group, the carbamoyl group, the sulfamoyl group, and the heterocyclic group of $R^{b1}$ may be substituted with one or more groups selected from substituent group $A_1$.

As the substituent group $A_1$ that substitutes $R^{b1}$, a $C_{1-3}$ alkyl group which may be substituted with one or more groups selected from the substituent group $A_2$, a $C_{1-3}$ alkoxy group which may be substituted with one or more groups selected from the substituent group $A_2$, or a heterocyclic group which may be substituted with one or more groups selected from the substituent group $A_2$ is preferable.

The compound in which $R^{b1}$ is a hydrogen atom, a halogen atom, a $C_{1-6}$ alkyl group which may be substituted, a $C_{1-6}$ alkoxy group which may be substituted, a $C_{1-6}$ alkylamino group which may be substituted, a di($C_{1-6}$ alkyl) amino group which may be substituted, or a heterocyclic group which may be substituted is preferable.

The compound in which $R^{b1}$ is a hydrogen atom, a fluorine atom, a chlorine atom, a $C_{1-3}$ alkyl group which may be substituted, a $C_{1-3}$ alkoxy group which may be substituted, a $C_{1-3}$ alkylamino group which may be substituted, a di($C_{1-3}$ alkyl)amino group which may be substituted, or a heterocyclic group which may be substituted is more preferable.

The compound in which $R^{b1}$ is a hydrogen atom, a methyl group, a methoxy group, a $C_{1-3}$ alkylamino group which may be substituted, a di($C_{1-3}$ alkyl)amino group which may be substituted, or a heterocyclic group which may be substituted is still more preferable.

In a case where $R^{b1}$ is a $C_{1-3}$ alkylamino group which may be substituted, the compound in which $R^{b1}$ is a $C_{1-3}$ alkylamino group substituted with a heterocyclic group having one or more substituents selected from a pyridyl group and a pyrimidyl group is particularly preferable.

In a case where $R^{b1}$ is a di($C_{1-3}$ alkyl)amino group which may be substituted, the compound in which $R^{b1}$ is a di($C_{1-3}$ alkyl)amino group substituted with a $C_{1-3}$ alkoxy group is even more preferable.

In a case where $R^{b1}$ is a heterocyclic group which may be substituted, it is even more preferably a monocyclic nitrogen-containing heterocyclic group which may be substituted or a monocyclic nitrogen-oxygen-containing heterocyclic group which may be substituted.

In a case where $R^{b1}$ is a heterocyclic group which may be substituted, it is particularly preferably a heterocyclic group having one or more substituents selected from a $C_{1-3}$ alkyl group, a $C_{1-3}$ alkoxy group, a $C_{1-6}$ alkoxy $C_{1-6}$ alkyl group, and a di($C_{1-3}$ alkyl)amino group.

The monocyclic nitrogen-containing heterocyclic group as $R^{b1}$, a pyrrolindinyl, piperidinyl, piperazinyl, azetidinyl, or 1,4-diazepanyl group is particularly preferable.

The monocyclic nitrogen-oxygen-containing heterocyclic group as $R^{b1}$ is particularly preferably a morpholinyl group.

m is an integer of 0 to 3.

The compound in which m is 0 or 1 is preferable, and the compound in which m is 0 is more preferable.

$R^2$ is a $C_{2-6}$ alkenyl group which may be substituted, a $C_{2-6}$ alkynyl group which may be substituted, a $C_{3-8}$ cycloalkyl group which may be substituted, an aryl group which may be substituted, or a heterocyclic group which may be substituted.

Each of the $C_{2-6}$ alkenyl group, the $C_{2-6}$ alkynyl group, the $C_{3-8}$ cycloalkyl group, the aryl group, and the heterocyclic group of $R^2$ may be substituted with one or more groups selected from substituent group $A_1$.

The compound in which $R^2$ is an aryl group which may be substituted, or a heterocyclic group which may be substituted is preferable, the compound in which $R^2$ is a phenyl group which may be substituted, a thienyl group which may be substituted, a thiazolyl group which may be substituted, or a benzoxazinyl group which may be substituted is more preferable, and the compound in which $R^2$ is a phenyl group which may have one or more substituents selected from the substituent group $A_1$, a thienyl group which may have one or more substituents selected from the substituent group $A_1$, a thiazolyl group which may have one or more substituents selected from the substituent group $A_1$, or a benzoxazinyl group represented by General Formula [2] is still more preferable:

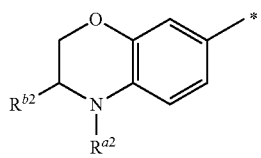

[2]

(in the formula, $R^{a2}$, $R^{b2}$, and * have the same definitions as above).

The number of the substituents of $R^2$ is preferably 1 or 2.

$R^{a2}$ is a hydrogen atom, a $C_{1-6}$ alkyl group which may be substituted, an acyl group which may be substituted, a $C_{1-6}$ alkylsulfonyl group which may be substituted, or an arylsulfonyl group which may be substituted.

Each of the $C_{1-6}$ alkyl group, the acyl group, the $C_{1-6}$ alkylsulfonyl group, and the arylsulfonyl group of $R^{a2}$ may be substituted with one or more groups selected from substituent group $A_1$.

The compound in which $R^{a2}$ is a hydrogen atom or a $C_{1-6}$ alkyl group which may be substituted is preferable, and the compound in which $R^{a2}$ is a hydrogen atom or a $C_{1-3}$ alkyl group which may be substituted is more preferable.

$R^{b2}$ is a hydrogen atom, a $C_{1-6}$ alkyl group which may be substituted, an aryl group which may be substituted, an acyl group which may be substituted, a carbamoyl group which may be substituted, a sulfamoyl group which may be substituted, a heterocyclic group which may be substituted, or a carboxyl group which may be protected.

The $C_{1-6}$ alkyl group, the aryl group, the acyl group, the carbamoyl group, the sulfamoyl group, and the heterocyclic group of $R^{b2}$ may be substituted with one or more groups selected from substituent group $A_1$.

The compound in which $R^{b2}$ is a hydrogen atom is preferable.

In another aspect, $R^{a2}$ and $R^{b2}$ may be combined with an atom to which they are bonded to form a 5-membered heterocycle which may be substituted or a 6-membered heterocycle which may be substituted.

The 5-membered heterocycle or 6-membered heterocycle formed by combination of $R^{a2}$, $R^{b2}$, and an atom to which $R^{a2}$ and $R^{b2}$ are bonded may be substituted with one or more groups selected from substituent group $A_1$.

Examples of the 5-membered heterocycle formed by combination of $R^{a2}$, $R^{b2}$, and an atom to which $R^{a2}$ and $R^{b2}$ are bonded include pyrrolidine, imidazolidine, and pyrazolidine.

Preferred examples of the 5-membered heterocycle include pyrrolidine.

Examples of the 6-membered heterocycle formed by combination of $R^{a2}$, $R^{b2}$, and an atom to which $R^{a2}$ and $R^{b2}$ are bonded include piperidine, tetrahydropyridine, piperazine, and morpholine.

It is preferable that $R^{a2}$, $R^{b2}$, and an atom to which $R^{a2}$ and $R^{b2}$ are bonded are combined to form a 5-membered heterocycle which may be substituted.

The compound in which $R^{a2}$ is a hydrogen atom or a $C_{1-6}$ alkyl group which may be substituted and $R^{b2}$ is a hydrogen atom; or the compound in which $R^{a2}$, $R^{b2}$, and an atom to which $R^{a2}$ and $R^{b2}$ are bonded are combined to form a 5-membered heterocycle which may be substituted is more preferable.

The compound in which $R^{a2}$, $R^{b2}$, and an atom to which $R^{a2}$ and $R^{b2}$ are bonded are combined to form a 5-membered heterocycle which may be substituted is still more preferable.

Substituent Group $A_1$:

a halogen atom, a cyano group, a nitro group, a $C_{1-6}$ alkyl group which may have one or more substituents selected from the substituent group $A_2$, an aryl group which may have one or more substituents selected from the substituent group $A_2$, a $C_{1-6}$ alkoxy group which may have one or more substituents selected from the substituent group $A_2$, a $C_{1-6}$ alkylamino group which may have one or more substituents selected from the substituent group $A_2$, a di($C_{1-6}$ alkyl)amino group which may have one or more substituents selected from the substituent group $A_2$, a carbamoyl group which may have one or more substituents selected from the substituent group $A_2$, a sulfamoyl group which may have one or more substituents selected from the substituent group $A_2$, a heterocyclic group which may have one or more substituents selected from the substituent group $A_2$, and a carboxyl group which may be protected.

Substituent Group $A_2$:

a halogen atom, a cyano group, a nitro group, a $C_{1-6}$ alkyl group which may have one or more substituents selected from the substituent group $A_3$, an aryl group which may have one or more substituents selected from the substituent group $A_3$, a $C_{1-6}$ alkoxy group which may have one or more substituents selected from the substituent group $A_3$, a $C_{1-6}$ alkylamino group which may have one or more substituents selected from the substituent group $A_3$, a di($C_{1-6}$ alkyl)amino group which may have one or more substituents selected from the substituent group $A_3$, an acylamino group which may have one or more substituents selected from the substituent group $A_3$, a carbamoyl group which may have one or more substituents selected from the substituent group $A_3$, a sulfamoyl group which may have one or more substituents selected from the substituent group $A_3$, a heterocyclic group which may have one or more substituents selected from the substituent group $A_3$, and a carboxyl group which may be protected.

Substituent Group $A_3$:

a halogen atom, a cyano group, a nitro group, a $C_{1-6}$ alkyl group which may have one or more substituents selected from the substituent group $A_4$, an aryl group which may have one or more substituents selected from the substituent group $A_4$, a $C_{1-6}$ alkoxy group which may have one or more substituents selected from the substituent group $A_4$, a $C_{1-6}$ alkylamino group which may have one or more substituents selected from the substituent group $A_4$, a di($C_{1-6}$ alkyl)amino group which may have one or more substituents selected from the substituent group $A_4$, a carbamoyl group which may have one or more substituents selected from the substituent group $A_4$, a sulfamoyl group which may have one or more substituents selected from the substituent group $A_4$, a heterocyclic group which may have one or more substituents selected from the substituent group $A_4$, and a carboxyl group.

Substituent Group $A_4$:

a halogen atom, a cyano group, a nitro group, a $C_{1-6}$ alkyl group, aryl group, a $C_{1-6}$ alkoxy group, a $C_{1-6}$ alkylamino group, a di($C_{1-6}$ alkyl)amino group, a carbamoyl group, a sulfamoyl group, heterocyclic group, and a carboxyl group.

In a case where $R^2$ is a phenyl group which may have one or more substituents selected from the substituent group $A_1$, it is preferable that the substituent group $A_1$ is:

a halogen atom, a cyano group, a $C_{1-6}$ alkyl group which may have one or more substituents selected from the substituent group $A_2$, a $C_{1-6}$ alkoxy group which may have one or more substituents selected from the substituent group $A_2$, a $C_{1-6}$ alkylamino group which may have one or more substituents selected from the substituent group $A_2$, a di($C_{1-6}$ alkyl)amino group which may have one or more substituents selected from the substituent group $A_2$, or a heterocyclic group which may have one or more substituents selected from the substituent group $A_2$;

the substituent group $A_2$ is:

a $C_{1-6}$ alkoxy group which may have one or more substituents selected from the substituent group $A_3$, an acylamino group which may have one or more substituents selected from the substituent group $A_3$, or a carbamoyl group which may have one or more substituents selected from the substituent group $A_3$;

the substituent group $A_3$ is:

a $C_{1-6}$ alkyl group which may have one or more substituents selected from the substituent group $A_4$, an aryl group which may have one or more substituents selected from the substituent group $A_4$, or a $C_{1-6}$ alkoxy group which may have one or more substituents selected from the substituent group $A_4$; and the substituent group $A_4$ is:

a halogen atom, a cyano group, or a $C_{1-6}$ alkyl group.

It is more preferable that the substituent group $A_1$ is:

a halogen atom, a cyano group, a $C_{1-3}$ alkoxy group, a di($C_{1-3}$ alkyl)amino group, or a pyrrolindinyl group which may have one or more substituents selected from the substituent group $A_2$;

the substituent group $A_2$ is:

a $C_{1-3}$ alkoxy group which may have one or more substituents selected from the substituent group $A_3$;

the substituent group $A_3$ is:

a phenyl group which may have one or more substituents selected from the substituent group $A_4$ or a $C_{1-3}$ alkoxy group; and the substituent group $A_4$ is:

a halogen atom.

In another aspect, in a case where $R^2$ is a thienyl group which may have one or more substituents selected from the substituent group $A_1$, it is preferable that the substituent group $A_1$ is:

a halogen atom, a cyano group, a nitro group, a $C_{1-6}$ alkyl group which may have one or more substituents selected from the substituent group $A_2$, an aryl group which may have one or more substituents selected from the substituent group $A_2$, a $C_{1-6}$ alkoxy group which may have one or more substituents selected from the substituent group $A_2$, a $C_{1-6}$ alkylamino group which may have one or more substituents selected from the substituent group $A_2$, a di($C_{1-6}$ alkyl)amino group which may have one or more substituents selected from the substituent group $A_2$, a carbamoyl group which may have one or more substituents selected from the substituent group $A_2$, a sulfamoyl group which may have one or more substituents selected from the substituent group $A_2$, a heterocyclic group which may have one or more substituents selected from the substituent group $A_2$, or a carboxyl group which may be protected; and the substituent group $A_2$ is:

a halogen atom, a cyano group, a nitro group, a $C_{1-6}$ alkyl group, an aryl group, a $C_{1-6}$ alkoxy group, a $C_{1-6}$ alkylamino group, a di($C_{1-6}$ alkyl)amino group, a carbamoyl group, a sulfamoyl group, a heterocyclic group, or a carboxyl group.

It is more preferable that the substituent group $A_1$ is:

an aryl group which may have one or more substituents selected from the substituent group $A_2$; and the substituent group $A_2$ is a halogen atom or a cyano group.

Furthermore, in another aspect, in a case where $R^2$ is a thiazolyl group which may have one or more substituents selected from the substituent group $A_1$, it is preferable that the substituent group $A_1$ is:

a halogen atom, a cyano group, a nitro group, a $C_{1-6}$ alkyl group, an aryl group, a $C_{1-6}$ alkoxy group,
a $C_{1-6}$ alkylamino group,
a di($C_{1-6}$ alkyl)amino group,
a carbamoyl group,
a sulfamoyl group,
a heterocyclic group, or
a carboxyl group.

It is more preferable that the substituent group $A_1$ is a heterocyclic group, and it is still more preferable that the substituent group A j is a pyrrolindinyl group.

$R^3$ is a hydrogen atom or a carboxy-protecting group.

The compound in which $R^3$ is preferably a hydrogen atom is preferable.

The 4-pyridone compound or a salt thereof of an embodiment of the present invention is preferably at least one compound selected from the group consisting of 6-(3-chloro-4-(pyrrolidin-1-yl)phenyl)-1-(2-(4-(2-methoxyethyl)piperazin-1-yl)benzo[d]thiazol-6-yl)-4-oxo-1,4-dihydropyridine-3-carboxylic acid, 1-(2-((R)-2-(methoxymethyl)pyrrolidin-1-yl)benzo[d]thiazol-6-yl)-6-(4-((R)-3-methoxypyrrolidin-1-yl)phenyl)-4-oxo-1,4-dihydropyridine-3-carboxylic acid, (S)-1-(2-(3-(dimethylamino)pyrrolidin-1-yl)benzo[d]thiazol-6-yl)-4-oxo-6-(4-(pyrrolidin-1-yl)phenyl)-1,4-dihydropyridine-3-carboxylic acid, (R)-1-(2-(3-(dimethylamino)pyrrolidin-1-yl)benzo[d]thiazol-6-yl)-4-oxo-6-(4-(pyrrolidin-1-yl)phenyl)-1,4-dihydropyridine-3-carboxylic acid, (S)-1-(2-(3-methoxypyrrolidin-1-yl)benzo[d]thiazol-6-yl)-4-oxo-6-(4-(pyrrolidin-1-yl)phenyl)-1,4-dihydropyridine-3-carboxylic acid, (R)-1-(2-(3-methoxypyrrolidin-1-yl)benzo[d]thiazol-6-yl)-4-oxo-6-(4-(pyrrolidin-1-yl)phenyl)-1,4-dihydropyridine-3-carboxylic acid, 1-(2-((3R,4R)-3,4-dimethoxypyrrolidin-1-yl)benzo[d]thiazol-6-yl)-4-oxo-6-((S)-2,3,3a,benzo[b]pyrrolo[1,2-d][1,4]oxazin-7-yl)-1,4-dihydropyridine-3-carboxylic acid, (S)-1-(2-(3-methoxyazetidin-1-yl)benzo[d]thiazol-6-yl)-4-oxo-6-(2,3,3a,4-tetrahydro-1H-benzo[b]pyrrolo[1,2-d][1,4]oxazin-7-yl)-1,4-dihydropyridine-3-carboxylic acid, (R)-6-(4-(3-(2-methoxyethoxy)pyrrolidin-1-yl)phenyl)-1-(2-morpholinobenzo[d]thiazol-6-yl)-4-oxo-1,4-dihydropyridine-3-carboxylic acid, 6-(4-((R)-3-(2-methoxyethoxy)pyrrolidin-1-yl)phenyl)-1-(2-((R)-2-(methoxymethyl)pyrrolidin-1-yl)benzo[d]thiazol-6-yl)-4-oxo-1,4-dihydropyridine-3-carboxylic acid, (R)-6-(3-fluoro-4-(3-methoxypyrrolidin-1-yl)phenyl)-1-(2-morpholinobenzo[d]thiazol-6-yl)-4-oxo-1,4-dihydropyridine-3-carboxylic acid, (R)-6-(3-fluoro-4-(3-methoxypyrrolidin-1-yl)phenyl)-1-(2-(3-methoxyazetidin-1-yl)benzo[d]thiazol-6-yl)-4-oxo-1,4-dihydropyridine-3-carboxylic acid, 6-(3-fluoro-4-((R)-3-methoxypyrrolidin-1-yl)phenyl)-1-(2-((S)-3-morpholinopyrrolidin-1-yl)benzo[d]thiazol-6-yl)-4-oxo-1,4-dihydropyridine-3-carboxylic acid, (R)-1-(2-(3-(difluoromethoxy)azetidin-1-yl)benzo[d]thiazol-6-yl)-6-(3-fluoro-4-(3-methoxypyrrolidin-1-yl)phenyl)-4-oxo-1,4-dihydropyridine-3-carboxylic acid, 6-(3-fluoro-4-((R)-3-methoxypyrrolidin-1-yl)phenyl)-4-oxo-1-(2-(3-((tetrahydrofuran-2-yl)methoxy)azetidin-1-yl)benzo[d]thiazol-6-yl)-1,4-dihydropyridine-3-carboxylic acid, (R)-6-(3-fluoro-4-(3-methoxypyrrolidin-1-yl)phenyl)-1-(2-(3-fluoroethoxy)azetidin-1-yl)benzo[d]pyridin-6-yl)-4-oxo-1,4-dihydropyridine-3-carboxylic acid, (R)-6-(3-fluoro-4-(3-methoxypyrrolidin-1-yl)phenyl)-1-(2-(3-methoxypropoxy)azetidin-1-yl)benzo[d]pyridin-6-yl)-4-oxo-1,4-dihydropyridine-3-carboxylic acid, (R)-1-(2-(3-ethoxyazetidin-1-yl)benzo[d]thiazol-6-yl)-6-(3-fluoro-4-(3-methoxypyrrolidin-1-yl)phenyl)-4-oxo-1,4-dihydropyridine-3-carboxylic acid, (R)-6-(3-fluoro-4-(3-methoxypyrrolidin-1-yl)phenyl)-1-(2-(3-isopropoxyazetidin-1-yl)benzo[d]thiazol-6-yl)-4-oxo-1,4-dihydropyridine-3-carboxylic acid, (R)-6-(3-fluoro-4-(3-methoxypyrrolidin-1-yl)phenyl)-1-(2-(3-methoxy-3-methylazetidin-1-yl)benzo[d]thiazol-6-yl)-4-oxo-1,4-dihydropyridine-3-carboxylic acid and (R)-6-(3-fluoro-4-(3-methoxypyrrolidin-1-yl)phenyl)-1-(2-(3-(2-methoxyethoxy)azetidin-1-yl)benzo[d]pyridin-6-yl)-4-oxo-1,4-dihydropyridine-3-carboxylic acid, or a salt thereof.

Example of the salt of the compound represented by General Formula [1] include a generally known salt of a basic group such as an amino group or of an acidic group such as a hydroxyl group and a carboxyl group.

Examples of the salt of the basic group include a salt with a mineral acid such as hydrochloric acid, hydrobromic acid, nitric acid, and sulfuric acid; a salt with an organic carboxylic acid such as formic acid, acetic acid, citric acid, oxalic acid, fumaric acid, maleic acid succinic acid, malic acid, tartaric acid, aspartic acid, trichloroacetic acid, and trifluoroacetic acid; and a salt with a sulfonic acid such as methanesulfonic acid, benzenesulfonic acid, p-toluenesulfonic acid, mesitylenesulfonic acid, and naphthalenesulfonic acid.

Examples of the salt of the acidic group include a salt with an alkali metal such as sodium and potassium; a salt with an alkali earth metal such as calcium and magnesium; an ammonium salt; and a salt with a nitrogen-containing organic base such as trimethylamine, triethylamine, tributylamine, pyridine, N,N-dimethylaniline, N-methylpiperidine, 4-methylmrnorpholine, diethylamine, dicyclohexylamine, procaine, dibenzylamine, N-benzyl-β-phenethylamine, 1-ephenamine and N,N'-dibenzylethylenedianine.

Among the above-mentioned salts, preferred examples of the salts include a pharmacologically acceptable salt.

In a case where the compound represented by General Formula [1] has an isomer (for example, an optical isomer, a geometric isomer, and a tautomer), the present invention encompasses the isomers and also encompasses a solvate, a hydrate, and crystals in various shapes.

In addition, the present invention further encompasses a prodrug of the compound represented by General Formula [1].

Next, a method for producing the compound represented by General Formula [1] will be described.

The compound represented by General Formula [1] is produced by combination of per se known methods, but can be produced by, for example, a production method shown below.

[Production Process 1]

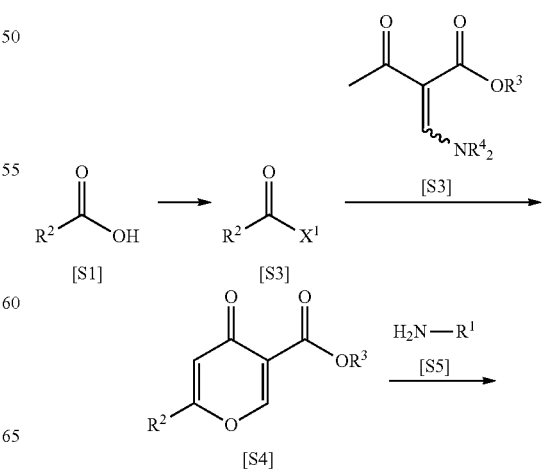

-continued $$[1] \quad \rightarrow \quad [1a]$$

(In the formula, $X^1$ is halogen atom, $R^4$ is a $C_{1-6}$ alkyl group, and $R^1$, $R^2$, and $R^3$ have the same definitions as above.)

The halogen atom represented by $X^1$ is preferably a chlorine atom.

$R^4$ is preferably a methyl group.

The compound represented by General Formula [S4] can be produced by reacting an acid halide [S2] derived from a compound represented by General Formula [S1] and a compound represented by General Formula [S3], and then subjecting the product to an acidic condition.

The reaction of the compound represented by General Formula [S2] with the compound represented by General Formula [S3] is performed in a solvent in the presence of a base.

The solvent used for this reaction is not particularly limited as long as it does not affect the reaction, but as a preferred solvent, ethers are preferable.

The amount of the solvent to be used is not particularly limited, but is preferably 1 to 500 times (v/w), and more preferably 1 to 100 times (v/w), with respect to the compound represented by General Formula [S3].

As a base used depending on the reaction, an organic base such as lithium bis(trimethylsilyl)amide is preferable.

An amount of the base to be used is preferably 1 to 10 times by mole, more preferably 1 to 5 times by mole, and still more preferably 0.1 to 3 times by mole, with respect to the compound represented by General Formula [S3].

This reaction may be carried out, preferably at −78° C. to 0° C. for 1 minute to 1 week in an inert gas (for example, nitrogen, argon) atmosphere.

The compound represented by General Formula [1] can be produced by reacting the compound represented by General Formula [S4] with a compound represented by General Formula [S5] in the presence of an acid.

The solvent used for this reaction is not particularly limited as long as it does not affect the reaction, but as a preferred solvent, alcohols and aromatic hydrocarbons are preferable.

The amount of the solvent to be used is not particularly limited, but is preferably 1 to 500 times (v/w), and more preferably 1 to 100 times (v/w), with respect to the compound represented by General Formula [S4].

As an acid used depending on the reaction, an acid such as acetic acid and p-toluene sulfonic acid is preferable.

An amount of the acid to be used is preferably 1 to 100 times by mole with respect to the compound represented by General Formula [S4].

This reaction may be preferably carried out at 0° C. to 150° C. for 1 minute to 1 week.

This reaction may be performed under irradiation of microwaves.

A compound represented by General Formula [Ia] can be produced by subjecting the compound represented by General Formula [1] to a deprotection reaction.

The deprotection may be performed by a method described in W. Greene et al., Protective Groups in Organic Synthesis, 5$^{th}$ edition, pp. 686 to 836, 2014, John Wiley & Sons, INC., or a method equivalent thereto.

As a base to be used for the deprotection, sodium hydroxide is preferable.

This reaction may be preferably carried out at 0° C. to 150° C. for 1 minute to 1 week.

In a case where an isomer (for example, an optical isomer, a geometric isomer, and a tautomer) of the compound used in the above-mentioned production method is present, these isomers can also be used. Further, a solvate, a hydrate, and crystals in various shapes are present, the solvate, the hydrate, and the crystals in various shapes can also be used.

As the compounds used in the above-mentioned preparation methods and intermediates thereof, a compound having a substituent (for example, an amino group, a hydroxyl group, and a carboxyl group) whose group can be protected with a usual protective groups beforehand, and after a reaction, the protective group can leave by a per se known method.

A compound obtained by the above-mentioned production method can be derived into another compound or a salt thereof by subjecting the compound to a per se known reaction such as condensation, addition, oxidation, reduction, rearrangement, substitution, halogenation, dehydration, and hydrolysis, or to an appropriate combination of these reactions.

The "pharmaceutical", the "agent", or the "pharmaceutical composition" of the embodiment of the present invention can be formed into a composition in appropriate mixture of preparation adjuvants such as an excipient, a carrier, and a diluent which are used in preparation, in addition to the compound or a salt thereof of the embodiment of the present invention, which is an active ingredient. The "pharmaceutical", the "agent", or the "pharmaceutical composition" may include other active ingredients or used n combination of a pharmaceutical including other active ingredients.

In a case where the compound represented by General Formula [1] or a salt thereof of the embodiment of the present invention is used as the pharmaceutical, the agent, or the pharmaceutical composition, it can be usually appropriately mixed with a pharmacologically acceptable additive.

Examples of the additive include an excipient, a disintegrating agent, a binder, a lubricant, a corrigent, a coloring agent, a flavoring agent, a surfactant, a coating agent, and a plasticizer.

Examples of the excipient include sugar alcohols such as erythritol, mannitol, xylitol, and sorbitol; saccharides such as saccharose, powder sugar, lactose, and glucose; cyclodextrins such as α-cyclodextrin, β-cyclodextrin, γ-cyclodextrin, hydroxypropyl β-cyclodextrin, and sodium sulfobutyl ether β-cyclodextrin; celluloses such as crystalline cellulose and microcrystalline cellulose; and starches such as corn starch, potato starch, and pregelatinized starch.

Examples of the disintegrating agent include carmellose, carmellose calcium, croscarmellose sodium, sodium carboxymethyl starch, crospovidone, low-substituted hydroxypropyl cellulose, and partially pregelatinized starch.

Examples of the binder include hydroxypropyl cellulose, carmellose sodium, and methyl cellulose.

Examples of the lubricant include stearic acid, magnesium stearate, calcium stearate, talc, hydrated silicon dioxide, light anhydrous silicic acid, and sucrose fatty acid esters.

Examples of the corrigent include aspartame, saccharin, stevia, thaumatin, and acesulfame potassium.

Examples of the coloring agent include titanium dioxide, iron sesquioxide, yellow iron sesquioxide, black iron oxide, edible red 102, edible yellow 4, and edible yellow 5.

Examples of the flavoring agent include essential oils such as an orange oil, a lemon oil, a mentha oil, and a pine oil; essences such as an orange essence and a peppermint essence; flavors such as a cherry flavor, a vanilla flavor, and a fruit flavor; powdered flavors such as an apple micron, a banana micron, a peach micron, a strawberry micron, and an orange micron; vanillin; and ethylvanillin.

Examples of the surfactant include sodium lauryl sulfate, dioctyl sodium sulfosuccinate, polysorbate, and polyoxyethylene hydrogenated castor oils.

Examples of the coating agent include hydroxypropylmethyl cellulose, aminoalkyl methacrylate copolymer E, aminoalkyl methacrylate copolymer RS, ethyl cellulose, cellulose acetate phthalate, hydroxypropylmethyl cellulose phthalate, methacrylic acid copolymer L, methacrylic acid copolymer LD, and methacrylic acid copolymer S.

Examples of the plasticizer include triethyl citrate, macrogol, triacetin, and propylene glycol.

These additives may be used alone or in combination of two or more kinds thereof.

The blending amount thereof is not particularly limited, and the additives may be appropriately blended so that an effect thereof is sufficiently exerted depending on each of the purposes.

These can be administered orally or parenterally in the form of a tablet, a capsule, a powder, a syrup, a granule, a pill, a suspension, an emulsion, a liquid, a powder formulation, a suppository, an eye drop, a nasal drop, an ear drop, a patch, an ointment, an injection, or the like according to an ordinary method. In addition, a method for administration, a dosage, and the number of doses can be appropriately selected in accordance with ages, weights, and symptoms of patients. Usually, an adult may be administered a dose of 0.01 to 1,000 mg/kg at a time or in several portions a day orally or parenterally (for example, administration by injection, by drip, and to a rectal region).

Prevention means inhibition of an onset, reduction in an onset risk, retardation of an onset, or the like.

Treatment means improvement of a targeted disease or condition, suppression of aggravation of the disease or condition, or the like.

A therapeutic treatment means prevention or treatment of any of various diseases, or the like.

A therapeutic agent means a substance provided for the purpose of prevention or treatment of any of various diseases, or the like.

The anti-hepatitis B virus agent of the present invention is useful for prevention or treatment of HBV infection.

The compound represented by General Formula [1] or a salt thereof of the embodiment of the present invention can inhibit the production or secretion of HBsAg and also inhibit expression of HBV gene (production of HBV DNA). Accordingly, the compound represented by General Formula [1] or a salt thereof of the embodiment of the present invention is useful for prevention or treatment of HBV infection.

The present invention relates to use of the compound represented by General Formula [1] or a salt thereof for inhibiting the production or secretion of HBsAg.

The present invention relates to use of the compound represented by General Formula [1] or a salt thereof for inhibiting the production of DNA of HBV The present invention relates to use of the compound represented by General Formula [1] or a salt thereof for inhibiting the gene expression of HBV.

The present invention relates to use of the compound represented by General Formula [1] or a salt thereof for prevention or treatment of HBV infection.

It is an object of the present invention to use the compound represented by General Formula [1] or a salt thereof for production of a pharmaceutical which is useful for treatment or prevention of diseases associated with HBV infection.

Examples of the diseases associated with HBV infection include progressive liver fibrosis, inflammation, necrosis, and the diseases progress to necrosis, cirrhosis, end-stage liver diseases, and hepatocellular carcinoma.

The present invention particularly relates to use of the compound represented by General Formula [1] or a salt thereof for production of a pharmaceutical which is useful for treatment or prevention of diseases associated with HBV infection.

In another aspect, the present invention includes a method for preventing or treating HBV infection, the method including administering an effective amount of the compound represented by General Formula [1], or a stereoisomer, a tautomer, a prodrug, a complex, or a pharmaceutically acceptable salt thereof.

The effective amount means a therapeutically or prophylactically effective amount. The therapeutically effective amount is an amount that is sufficient for stabilization of HBV infection, reduction in HBV infection, or eradication of HBV infection in an infected subject. The prophylactically effective amount is an amount that is sufficient for the prevention of HBV infection in a subject at risk of infection.

EXAMPLES

Next, the present invention will be described with reference to Reference Examples and Examples, but the present invention is not limited thereto.

An automatic purification apparatus ISOLERA (Biotage AB) or a medium-pressure liquid chromatograph YFLC W-prep 2XY (Yamazen Corporation) was used for purification by means of column chromatography unless otherwise specified.

A SNAP KP-Sil Cartridge (Biotage AB), CHROMATOREX Q-PACK S150 (Fuji Silysia Chemical Ltd.), or Hi-Flash Column W001, W002, W003, W004, or W005 (Yamazen Corporation) was used as a carrier in silica gel column chromatography unless otherwise specified.

A SNAP KP-NH Cartridge (Biotage AB) or CHROMATOREX NH60 (Fuji Silysia Chemical Ltd.)) was used as NH silica.

A SNAP KP-Sil Cartridge (Biotage AB) or Hi-Flash Column W001, W002, W003, W004, or W005 (Yamazen Corporation) was used as a carrier in silica gel column chromatography unless otherwise specified.

A SNAP KP-NH Cartridge (Biotage AB) was used as NH silica.

The mixing ratio regarding an eluent is a volume ratio.

For example, "100%-0% hexane/ethyl acetate-100%-80% ethyl acetate/methanol" means that "an eluent with 100% hexane/0% ethyl acetate was first changed to an eluent with 0% hexane/100% ethyl acetate, and then the eluent with 100% ethyl acetate/0% methanol was changed to an eluent with 80% ethyl acetate/20% methanol."

The MS spectra were measured by an ionization method in which an ACQUITY SQD LC/MS System (Waters, ionization method: an ElectroSpray Ionization (ESI)) method or an LCMS-2010 EV (Shimadzu Corporation, ionization method: ESI and Atmospheric Pressure Chemical Ionization (APCI)) is simultaneously performed.

MS in tables means MS (ESI n/z): (M+H) unless otherwise specified.

An initiator TM (Biotage AB) was used as a microwave reaction device.

NMR spectra were measured using tetramethylsilane as an internal standard and Bruker AV300 (manufactured by Bruker), and all δ values are expressed in ppm.

The abbreviations in the NMR measurement have the following definitions.

s: Singlet
brs: Broad singlet
d: Doublet
dd: Double doublet
t: Triplet
q: Quartet
m: Multiplet
DMSO-D6: Deuterated dimethylsulfoxide
MeOD: Deuterated methanol (MD$_3$OD)

A retention time (RT) was measured using SQD (Waters) and expressed in minutes (min).

Column: BEHC 18 manufactured by Waters, 1.7 μm, 2.1×30 mm
Solvents:
A liquid: 0.1% Formic acid-water
B liquid: 0.1% Formic acid-acetonitrile
Gradient cycle: 0.00 min (A liquid/B liquid=95/5), 2.00 min (A liquid/B liquid=5/95), 3.00 min (A liquid/B liquid=5/95)
Flow rate: 0.5 mL/min
Column temperature: Room temperature
Detection wavelength: 254 nm The respective abbreviations in each of Reference Examples and Examples have the following definitions.
Boc: tert-Butoxycarbonyl
DIEA: N,N-Diisopropylethylamine
DMF: N,N-Dimethylformamide
Et: Ethyl
Me: Methyl
NMP: N-Methyl-2-pyrrolidone
RT, rt: Retention time
THF: Tetrahydrofuran Reference Example 1

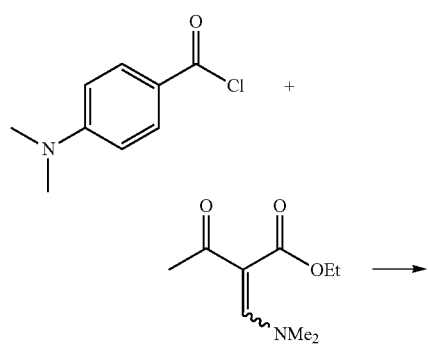

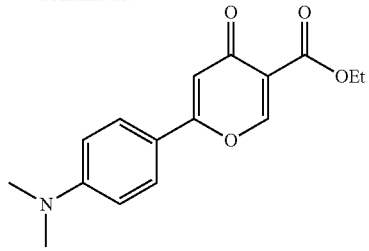

A 1.3 mol/L lithium bis(trimethylsilyl)amide-THF solution (23 mL) was cooled to −60° C., and then a THF solution (40 mL) of 4-(dimethylamino)benzoyl chloride (2.73 g) and ethyl=2-((dimethylamino)methylene)-3-oxobutanoate (2.50 g) was added dropwise thereto. The mixture was warmed to room temperature and stirred for 1 hour. The reaction mixture was cooled to −60° C., and 3 mol/L hydrochloric acid, ethyl acetate, and water were added thereto. The organic layer was collected by separation, washed with a saturated aqueous sodium chloride solution, and then dried over anhydrous sodium sulfate, and the solvent was evaporated under reduced pressure. The obtained residue was suspended in a mixed solvent of ethanol and hexane, and the precipitate was collected by filtration to ethyl 6-(4-(dimethylamino)phenyl)-4-oxo-4H-pyran-3-carboxylate (0.89 g) as a brown solid.

MS (ESI m/z): 288 (M+H)
RT (min): 1.29

Reference Example 2

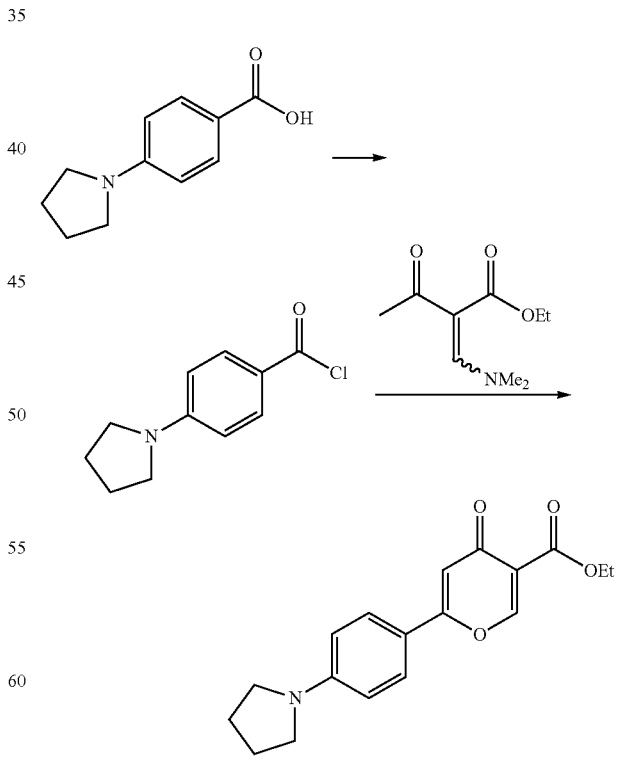

To a suspension of 4-(pyrrolidin-1-yl)benzoic acid (4.88 g) in toluene (60 mL) were added 2 droplets of DMF and oxalyl dichloride (5.47 mL), and the mixture was stirred at room temperature for 1 hour. The solvent was evaporated from the reaction mixture under reduced pressure to obtain a residue. 1.3 mol/L lithium bis(trimethylsilyl)amide/THF (43.1 mL) was cooled to −60° C., and then the residue and a THF solution (40 mL) of ethyl=2-((dimethylamino)methylene)-3-oxobutanoate (4.73 g) were added dropwise thereto. The mixture was warmed to room temperature and stirred for 30 minutes. The reaction mixture was cooled to −60° C., then 3 mol/L hydrochloric acid (90 mL) and ethyl acetate (20 mL) were added thereto, and the precipitate was collected by filtration. The organic layer of the filtrate was collected by separation, washed with a saturated aqueous sodium chloride solution, and dried over anhydrous sodium sulfate, and the solvent was evaporated under reduced pressure. The obtained residue and the precipitate collected by filtration were combined, the combination was suspended in a mixed solvent of ethanol and hexane, and the precipitate was collected by filtration to obtain ethyl 4-oxo-6-(4-(pyrrolidin-1-yl)phenyl)-4H-pyran-3-carboxylate (5.69 g) as a pale brown solid.

MS (ESI m/z): 314 (M+H)
RT (min): 1.49

Reference Example 3

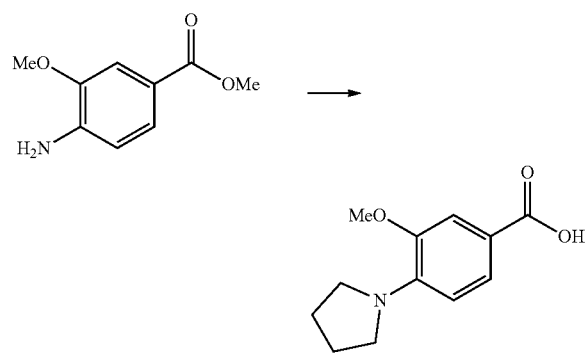

To an NMP solution (15 mL) of methyl 4-amino-3-methoxybenzoate (5.42 g) were added DIEA (7.6 g) and 1,4-diiodobutane (9.44 g), and the mixture was stirred at 90° C. for 5.5 hours. DIEA (1.52 g) and 1,4-diiodobutane (1.89 g) were added thereto, and the mixture was stirred at 90° C. for 4 hours. The reaction mixture was cooled to room temperature, then saturated saline was added thereto, and the mixture was extracted with a mixed solution of toluene and ethyl acetate. The organic layer was washed with water and saturated saline, and the aqueous layer was extracted with toluene. The organic layer and the extracted layer were combined, the combination was dried over anhydrous sodium sulfate, and then the solvent was evaporated under reduced pressure.

To a methanol solution (50 mL) of the obtained residue was added a 25% aqueous sodium hydroxide solution, and the mixture was stirred overnight at room temperature. To the reaction mixture was added 3 mol/L hydrochloric acid (15.2 mL) under ice-cooling, and the solvent was evaporated. The precipitate was collected by filtration, and the obtained solid was washed with water and azeotroped with acetonitrile to obtain 3-methoxy-4-(pyrrolidin-1-yl)benzoic acid (2 g) as a brown solid.

MS (ESI m/z): 222 (M+H)
RT (min): 0.95

Reference Example 4

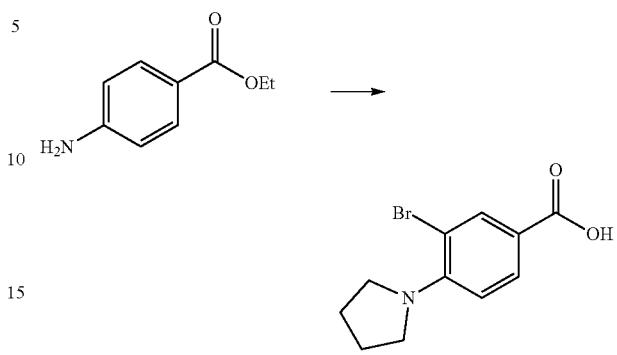

To an NMP solution (25 mL) of ethyl 4-aminobenzoate (3.0 g) were added DIEA (7.4 g) and 1,4-diiodobutane (9.4 g), and the mixture was stirred at 100° C. for 11 hours. DIEA (5.6 g) and 1,4-diiodobutane (7.1 g) were added thereto, and the mixture was stirred at 100° C. for 6 hours. The reaction mixture was cooled to room temperature, then water and saturated saline were added thereto, and the mixture was extracted with a mixed solution of toluene and ethyl acetate. The organic layer was washed with water and saturated saline, and dried over anhydrous sodium sulfate, and then the solvent was evaporated under reduced pressure.

To an acetonitrile solution (100 mL) of the obtained residue was added N-bromosuccinimide (2.7 g), and the mixture was stirred at room temperature for 2 hours. N-bromosuccinimide (2.4 g) was added thereto and the mixture was stirred at room temperature for 2 hours. To the reaction mixture was added a 5% aqueous sodium thiosulfate solution (20 mL), and then the solvent was evaporated. To the obtained mixture was added water, and the mixture was extracted with a mixed solution of toluene and ethyl acetate. The organic layer was washed with water, a saturated aqueous sodium hydrogen carbonate solution, and saturated saline, and dried over anhydrous sodium sulfate, and then the solvent was evaporated under reduced pressure.

To a methanol solution (100 mL) of the obtained residue was added a 5.0 mol/L aqueous sodium hydroxide solution (12 mL), and the mixture was stirred overnight at room temperature. A 5.0 mol/L aqueous sodium hydroxide solution (12 mL) was added thereto, and the mixture was stirred for 4 hours under ice-cooling. To the reaction mixture was added aqueous hydrochloric acid, and the solvent was evaporated. The precipitate was collected by filtration and the obtained solid was washed with water and tert-butylmethyl ether to obtain 3-bromo-4-(pyrrolidin-1-yl)benzoic acid (6.00 g) as a pale brown solid.

MS (ESI m/z): 270 (M+H)
RT (min): 1.46

Reference Example 5

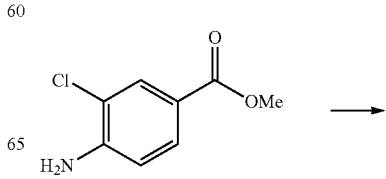

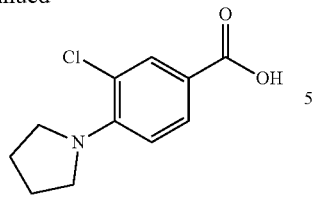

In the same manner as in Reference Example 3, the following compound was obtained. 3-Chloro-4-(pyrrolidin-1-yl)benzoic acid
MS (ESI m/z): 226 (M+H)
RT (min): 1.43

Reference Example 6

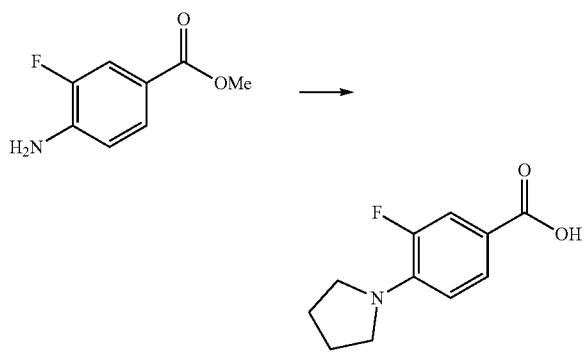

In the same manner as in Reference Example 3, the following compound was obtained.
3-Fluoro-4-(pyrrolidin-1-yl)benzoic acid
MS (ESI m/z): 210 (M+H)
RT (min): 1.35

Reference Example 7

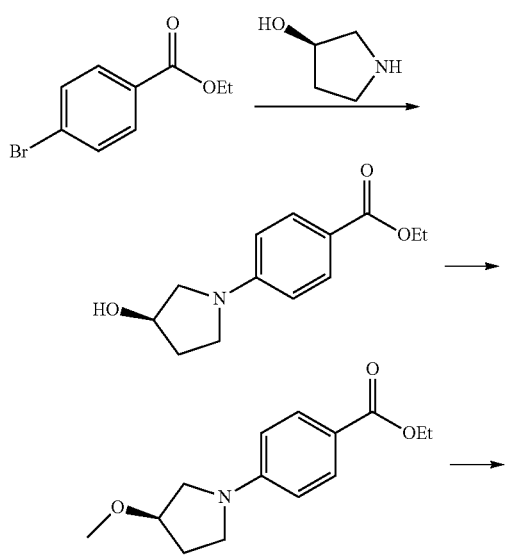

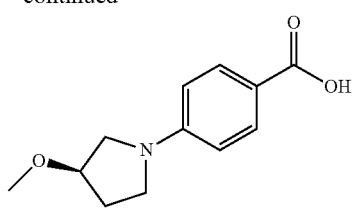

(1)

A mixture of ethyl 4-bromobenzoate (1.0 g), chloro(2-dicyclohexylphosphino-2',6'-diisopropoxy-1,1'-biphenyl)[2-(2'-amino-1,1'-biphenyl)]palladium (II) (1.73 mg), cesium carbonate (4.27 g), (R)-pyrrolidin-3-ol (1.14 g), and 1,2-dimethoxyethane (15 mL) was irradiated with microwaves (Initiator™, 120° C., 30 minutes, 2.45 GHz, 0-240 W). The same reaction was repeated three times and cooled to room temperature, then the obtained reaction mixture was combined, and the solvent was evaporated under reduced pressure. The obtained residue was purified by silica gel column chromatography [eluent; 80%-30% n-hexane/ethyl acetate] to obtain ethyl (R)-4-(3-hydroxypyrrolidin-1-yl)benzoate (3.80 g) as a yellow solid.

MS (ESI m/z): 236 (M+t)
RT (min): 1.17

(2)

To a mixture of ethyl (R)-4-(3-hydroxypyrrolidin-1-yl)benzoate obtained in (1) (4.06 g), methyl p-toluenesulfonate (6.43 g), DMF (20 mL), and THF (40 mL) was added sodium hydride (1.38 g, 60%, dispersed in fluidized paraffin) under ice-cooling. The mixture was warmed to room temperature and stirred for 1 hour, and then 1 mol/L hydrochloric acid (15 mL) and ethyl acetate were added thereto. The organic layer was collected by separation, and washed with water and a saturated aqueous sodium chloride solution, and then the solvent was evaporated under reduced pressure. The obtained residue was purified by silica gel column chromatography [eluent; 100%-60% n-hexane/ethyl acetate] to obtain ethyl (R)-4-(3-methoxypyrrolidin-1-yl)benzoate as a yellow oily substance.

MS (ESI m/z): 250 (M+H)
RT (min): 1.48

(3)

To a mixed solution of the obtained ethyl (R)-4-(3-methoxypyrrolidin-1-yl)benzoate in methanol (30 mL) was added a 1 mol/L aqueous sodium hydroxide solution (15 mL), and the mixture was stirred at 80° C. for 2 hours. To the reaction mixture were added methanol (10 mL) and a 1 mol/L aqueous sodium hydroxide solution (15 mL), and the mixture was stirred at 80° C. for 5 hours. The reaction mixture was cooled to room temperature, then 3 mol/L hydrochloric acid was added thereto, and the solvent was evaporated under reduced pressure. The obtained residue was suspended in water and the precipitate was collected by filtration to obtain (R)-4-(3-methoxypyrrolidin-1-yl)benzoic acid (3.42 g) as a white solid.

MS (ESI m/z): 222 (M+H)
RT (min): 1.04

Reference Example 8

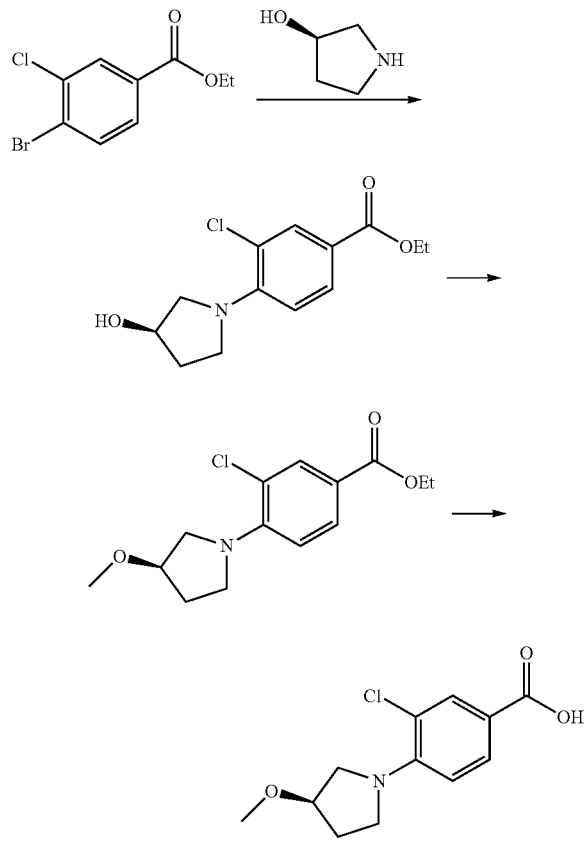

(1)

A mixture of ethyl 4-bromo-3-chlorobenzoate (4.78 g), tris(dibenzylideneacetone)dipalladium (0) (342 mg), (R)-(+)-2,2'-bis(diphenylphosphino)-1,1'-binaphthyl (699 mg), sodium tert-butoxide (2.52 g), (R)-pyrrolidin-3-ol (3.16 g), and toluene (150 mL) was stirred under heating and refluxing for 1 hour. The reaction mixture was cooled to room temperature, the insoluble matters were removed by filtration, and the solvent was evaporated under reduced pressure. To the obtained residue were added ethyl acetate and a saturated aqueous sodium hydrogen carbonate solution. The organic layer was collected by separation and washed with a saturated aqueous sodium hydrogen carbonate solution and saturated saline, and then the solvent was evaporated under reduced pressure. The obtained residue was purified by silica gel column chromatography [eluent; 50%-0% n-hexane/ ethyl acetate] to obtain ethyl (R)-3-chloro-4-(3-methoxypyrrolidin-1-yl)benzoate (982 mg) as a brown oily substance.

MS (ESI m/z): 270 (M+H)

RT (min): 1.35

(2)

In the same manner as in Reference Examples 7-(2) and 7-(3), the following compound was obtained.

(R)-3-Chloro-4-(3-methoxypyrrolidin-1-yl)benzoic acid

MS (ESI in/z): 256 (M+H)

RT (min): 1.22

Reference Example 9

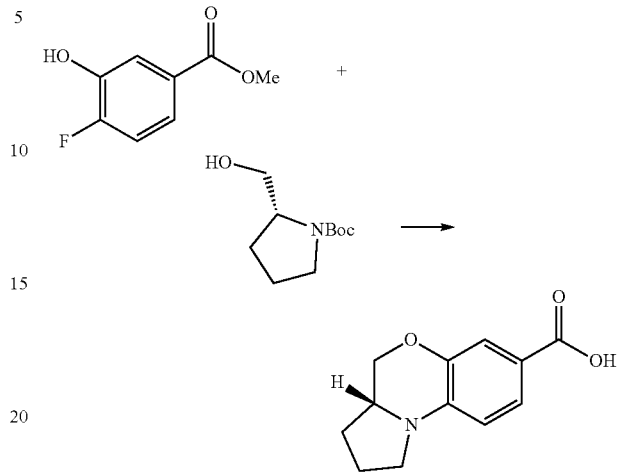

To a mixture of methyl 4-fluoro-3-hydroxybenzoate (3.25 g), tert-butyl (R)-2-(hydroxymethyl)pyrrolidine-1-carboxylate (5.0 g), triphenylphosphine (6.52 g), and THF (60 mL) was added a 2.2 mol/L diethyl azodicarboxylate-toluene solution (11.3 mL) under ice-cooling. The mixture was warmed to room temperature and stirred overnight, and then the solvent was evaporated under reduced pressure. To the obtained residue were added water (20 mL) and ethyl acetate (70 mL). The organic layer was collected by separation, washed with a saturated aqueous sodium chloride solution, and then dried over anhydrous sodium sulfate. To the obtained organic layer was added magnesium chloride (6.4 g) at room temperature, and the mixture was warmed to 50° C. and stirred for 1 hour. The reaction mixture was cooled to room temperature, then the insoluble matters were removed by filtration, and the solvent was evaporated under reduced pressure.

To the obtained residue was added 5 to 10 w/w % hydrochloric acid-methanol (30 mL) at room temperature, and the mixture was stirred for 5 days. The solvent was evaporated under reduced pressure, and then ethyl acetate (80 mL), a saturated aqueous sodium hydrogen carbonate solution (20 mL), and sodium carbonate were added thereto. The organic layer was collected by separation and then the aqueous layer was extracted with ethyl acetate. The organic layer and the extract were combined, and the solvent was evaporated under reduced pressure.

A mixture of the obtained residue, dimethyl sulfoxide (33 mL), and potassium carbonate (2.64 g) was stirred at 80° C. for 5 hours. The reaction mixture was cooled to room temperature, then saturated saline (75 mL) was added thereto, and the solid was collected by filtration and washed with water. The filtrate and the washing liquid were combined, and the combination was extracted with toluene. The obtained solid and the extract were combined, and the solvent was evaporated under reduced pressure.

To the obtained residue were added methanol (60 mL) and a 5 mol/L aqueous sodium hydroxide solution (20 mL), and the mixture was stirred at room temperature for 5 days. The reaction mixture was warmed and stirred at 50° C. for 2 hours, and then further stirred under heating and refluxing for 6 hours. The reaction mixture was cooled under ice-cooling, and then concentrated hydrochloric acid (12.1 mL)

was added thereto. The precipitate was collected by filtration and washed with water. The obtained precipitate was washed with ethyl acetate to obtain (R)-2,3,3a,4-tetrahydro-1H-benzo[b]pyrrolo[1,2-d][1,4]oxazine-7-carboxylic acid (3.34 g) as a yellow solid.

MS (ESI nm/z): 220 (M+H)
RT (min): 1.15

Reference Example 10

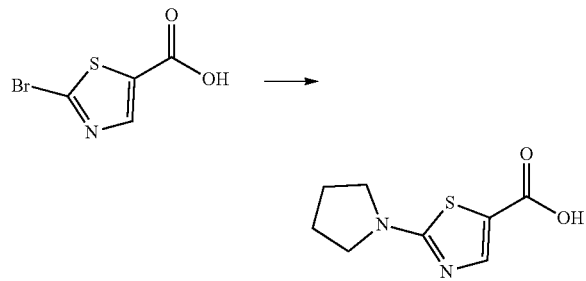

A mixture of 2-bromothiazole-5-carboxylic acid (0.5 g), pyrrolidine (2 mL), potassium carbonate (1.66 g), and 1,2-dimethoxyethane (15 mL) was irradiated with microwaves (Initiator™, 130° C., 1 hour, 2.45 GHz, 0-240 W). The reaction mixture was cooled to room temperature and then the solid was collected by filtration. The obtained solid was dissolved in water, and 3 mol/L hydrochloric acid was added thereto. The precipitate was collected by filtration to obtain 2-(pyrrolidin-1-yl)thiazole-5-carboxylic acid (229 mg) as a yellow solid.

MS (ESI n/z): 199 (M+H)
RT (min): 0.59

Reference Example 11

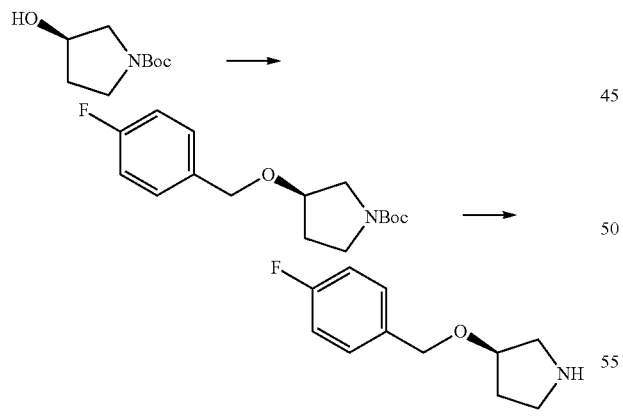

To a mixture of tert-butyl (R)-3-hydroxypyrrolidine-1-carboxylate (250 mg), 1-(bromomethyl)-4-fluorobenzene (1.08 g), DMF (0.5 mL), and THF (2.5 mL) was added sodium hydride (230 mg, 60%, dispersed in fluidized paraffin) at room temperature. The mixture was stirred at room temperature for 1 hour, and then a saturated aqueous sodium hydrogen carbonate solution and ethyl acetate were added thereto. The organic layer was collected by separation, and washed with water and a saturated aqueous sodium chloride solution, and then the solvent was evaporated under reduced pressure. The obtained residue was purified by silica gel column chromatography [eluent; 100%-60% n-hexane/ethyl acetate] to obtain tert-butyl (R)-3-((4-fluorobenzyl)oxy)pyrrolidine-1-carboxylate (381 mg).

MS (ESI m/z): 296 (M+H)
RT (min): 1.68

(2)
To a mixture of tert-butyl (R)-3-((4-fluorobenzyl)oxy) pyrrolidine-1-carboxylate obtained in (1) (381 mg) and cyclopentylmethyl ether (4 mL) was added 4.0 mol/L hydrogen chloride/cyclopentylmethyl ether (4 mL) at room temperature, and the mixture was stirred for 30 minutes. The mixture was warmed and stirred at 50° C. for 1 hour, and then the solvent was evaporated under reduced pressure. To the obtained residue was added a saturated aqueous sodium hydrogen carbonate solution, and the mixture was extracted with chloroform.

The organic layer was collected by separation and the solvent was evaporated under reduced pressure. The obtained residue was purified by silica gel column chromatography [eluent; 99%-80% ethyl acetate/methanol NH silica] to obtain (R)-3-((4-fluorobenzyl)oxy)pyrrolidine (314 mg) as a yellow oily substance.

MS (ESI m/z): 196 (M+H)
RT (min): 0.74

Reference Example 12

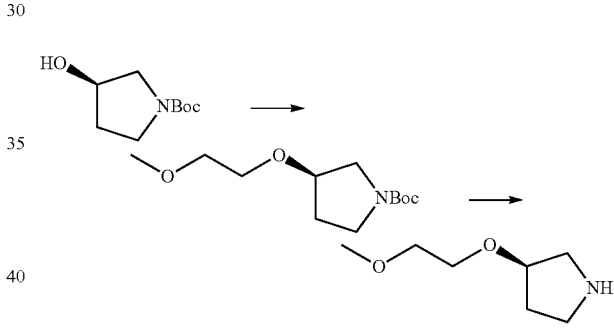

In the same manner as in Reference Examples 11-(1) and 11-(2), the following compound was obtained.
(R)-3-(2-Methoxyethoxy)pyrrolidine Reference Example 13

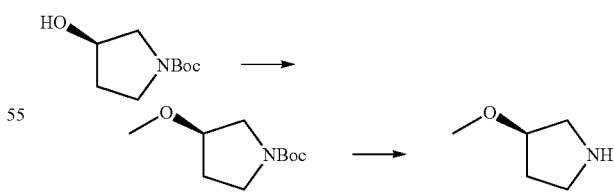

(1)
In the same manner as in Reference Example 7-(2), the following compound was obtained.
tert-Butyl (R)-3-methoxypyrrolidine-1-carboxylate (2)
To a mixture of tert-butyl (R)-3-methoxypyrrolidine-1-carboxylate obtained in (1) (487 mg) and cyclopentylmethyl ether (5 mL) was added 4.0 mol/L hydrogen chloride/ cyclopentyl methyl ether (5 mL) at room temperature. The mixture was warmed and stirred at 50° C. for 30 minutes, and the separated solvent was removed to obtain an oily substance (370 mg). To a mixture of the obtained oily substance and 1,2-dimethoxyethane (10 mL) were added DOWEX (registered trademark) and MONOSPHERE (registered trademark) 550A (1 g), and the mixture was neutralized. The reaction mixture was dried by the addition of anhydrous sodium sulfate, the insoluble matters were removed by filtration and filtered, and the residue was washed with 1,2-dimethoxyethane (5 mL). The filtrate and the washing liquid were combined to obtain a 1,2-dimethoxyethane solution of (R)-3-methoxypyrrolidine.

Reference Examples 14-1 to 14-11

In the same manner as in Reference Example 2, the following compounds were obtained.

TABLE 1

| Reference Example No. | | | MS (ESI m/z) (M + H) | RT (min) |
|---|---|---|---|---|
| 14-1 | | ethyl 6-(3-methoxy-4-(pyrrolidin-1-yl)phenyl)-4-oxo-4H-pyran-3-carboxylate | 344 | 1.03 |
| 14-2 | | ethyl 6-(3-bromo-4-(pyrrolidin-1-yl)phenyl)-4-oxo-4H-pyran-3-carboxylate | 394 | 1.68 |
| 14-3 | | ethyl 6-(3-chloro-4-(pyrrolidin-1-yl)phenyl)-4-oxo-4H-pyran-3-carboxylate | 348 | 1.66 |
| 14-4 | | ethyl 6-(3-fluoro-4-(pyrrolidin-1-yl)phenyl)-4-oxo-4H-pyran-3-carboxylate | 332 | 1.58 |

TABLE 1-continued

| Reference Example No. | Structure | Name | MS (ESI m/z) (M + H) | RT (min) |
|---|---|---|---|---|
| 14-5 | | (R)-ethyl 6-(4-(3-methoxypyrrolidin-1-yl)phenyl)-4-oxo-4H-pyran-3-carboxylate | 334 | 1.31 |
| 14-6 | | ethyl 6-(4-bromo-3-chlorophenyl)-4-oxo-4H-pyran-3-carboxylate | 359 | 1.50 |
| 14-7 | | ethyl 6-(4-bromophenyl)-4-oxo-4H-pyran-3-carboxylate | 325 | 1.38 |
| 14-8 | | (R)-ethyl 6-(3-chloro-4-(3-methoxypyrrolidin-1-yl)phenyl)-4-oxo-4H-pyran-3-carboxylate | 378 | 1.44 |

TABLE 2

| Reference Example No. | Structure | Name | MS (ESI m/z) (M + H) | RT(min) |
|---|---|---|---|---|
| 14-9 | | (R)-ethyl 4-oxo-6-(2,3,3a,4-tetrahydro-1H-benzo[b]pyrrolo[1,2-d][1,4]oxazin-7-yl)-4H-pyran-3-carboxylate | 342 | 1.41 |

TABLE 2-continued

| Reference Example No. | | Name | MS (ESI m/z) (M + H) | RT(min) |
|---|---|---|---|---|
| 14-10 | 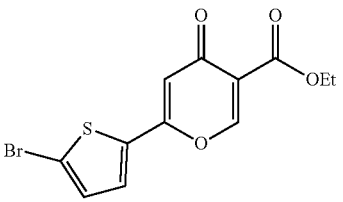 [SMILES: CCOC(=O)c1coc(-c2ccc(Br)s2)cc1=O] | ethyl 6-(5-bromothiophen-2-yl)-4-oxo-4H-pyran-3-carboxylate | 331 | 1.36 |
| 14-11 | 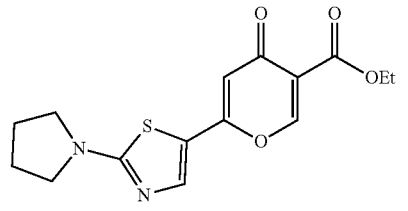 [SMILES: CCOC(=O)c1coc(-c2cnc(N3CCCC3)s2)cc1=O] | ethyl 4-oxo-6-(2-(pyrrolidin-1-yl)thiazol-5-yl)-4H-pyran-3-carboxylate | 321 | 1.10 |

Reference Example 15

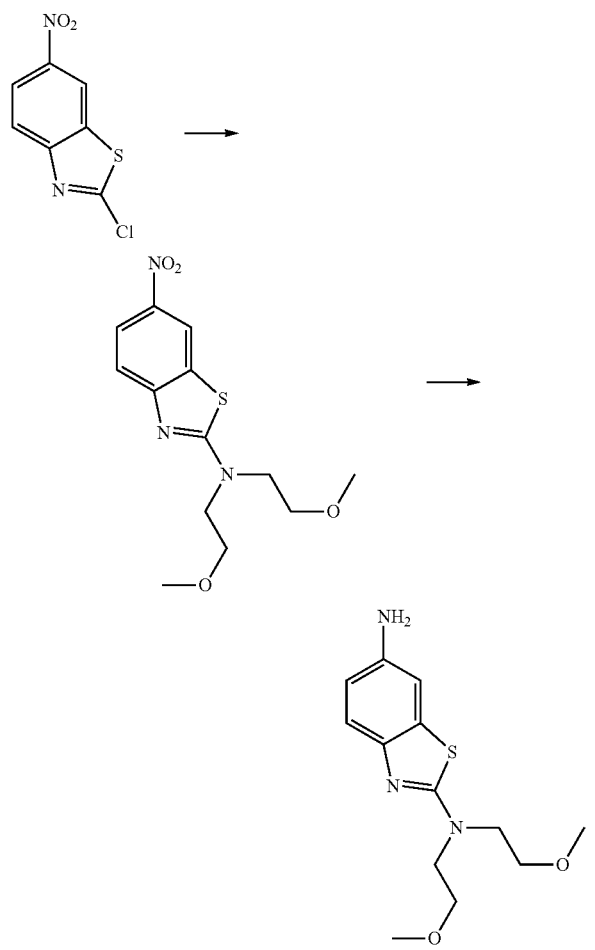

(1)

To a mixture of bis(2-methoxyethyl)amine (190 mg), triethylamine (142 mg), and dichloromethane (2 mL) was added a solution of 2-chloro-6-nitrobenzo[d]thiazole (100 mg) in DMF (1 mL) under ice-cooling. The mixture was warmed to room temperature and stirred for 1 hour, and then the solvent was evaporated under reduced pressure. To the obtained residue were added a saturated aqueous sodium chloride solution, and the mixture was extracted with ethyl acetate. The organic layer was collected by separation and the solvent was evaporated under reduced pressure to obtain N,N-bis(2-methoxyethyl)-6-nitrobenzo[d]thiazol-2-amine as a brown oily substance.

MS (ESI m/z): 312 (M+H)

RT (min): 1.46

(2)

To a mixture of N,N-bis(2-methoxyethyl)-6-nitrobenzo[d]thiazol-2-amine obtained in (1), powder zinc (244 mg), and ethanol (3 mL) was added acetic acid (1 mL), and the mixture was heated and refluxed for 30 minutes. The reaction mixture was cooled to room temperature and the insoluble matters were removed by filtration using Celite (registered trademark). The solvent was evaporated under reduced pressure and the obtained residue was purified by silica gel column chromatography [eluent; 100%-0% hexane/ethyl acetate→100%-80% ethyl acetate/methanol NH silica] to obtain $N^2,N^2$-bis(2-methoxyethyl)benzo[d]thiazole-2,6-diamine (1.27 mug).

MS (ESI m/z): 282 (M+H)

RT (min): 0.67

Reference Examples 16-1 to 16-9

In the same manner as in Reference Example 15, the following compounds were obtained.

TABLE 3
| Reference Example No. | | | MS (ESI m/z) (M + H) | RT(min) |
|---|---|---|---|---|
| 16-1 | 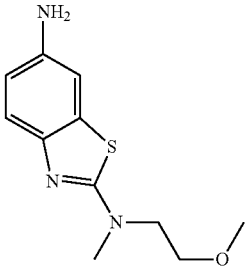 [SMILES: COCCN(C)c1nc2ccc(N)cc2s1] | N2-ethyl-N2-(2-methoxyethyl)benzo[d]-thiazole-2,6-diamine | 252 | 0.66 |
| 16-2 | 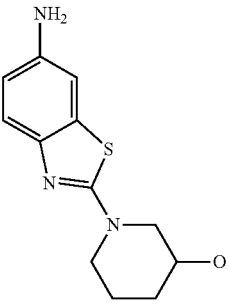 [SMILES: Nc1ccc2nc(N3CCCC(O)C3)sc2c1] | 2-(4-methoxypiperidin-1-yl)benzo[d]thiazol-6-amine | 264 | 0.65 |
| 16-3 | 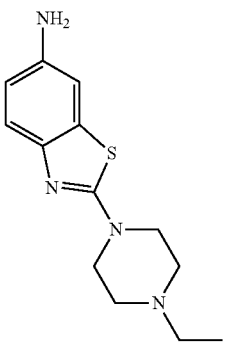 [SMILES: CCN1CCN(c2nc3ccc(N)cc3s2)CC1] | 2-(4-ethylpiperazin-1-yl)benzo[d]thiazol-6-amine | 263 | 0.23 |
| 16-4 | 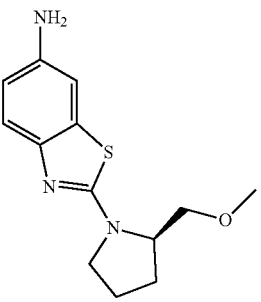 [SMILES: COC[C@H]1CCCN1c1nc2ccc(N)cc2s1] | (R)-2-(2-(methoxymethyl)pyrrolidin-1-yl)benzo[d]thiazol-6-amine | 264 | 0.65 |
| 16-5 | 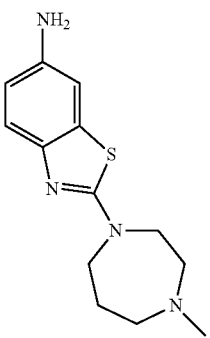 [SMILES: CN1CCCN(c2nc3ccc(N)cc3s2)CC1] | 2-(4-methyl-1,4-diazepan-1-yl)benzo[d]thiazol-6-amine | 263 | 0.22 |

TABLE 3-continued

| Reference Example No. | | | MS (ESI m/z) (M + H) | RT(min) |
|---|---|---|---|---|
| 16-6 | (structure) | N²-(Pyridin-2-ylmethyl)benzo[d]thiazole-2,6-diamine | 257 | 0.24 |
| 16-7 | (structure) | N²-(pyrimidin-2-ylmethyl)benzo[d]thiazole-2,6-diamine | 258 | 0.23 |
| 16-8 | (structure) | 2-(4-(2-methoxyethyl)piperazin-1-yl)benzo[d]thiazoi-6-amine | 293 | 0.24 |
| 16-9 | (structure) | N²-methyl-N2-((tetrahydro-2H-pyran-4-yl)methyl)benzo[d]thiazole-2,6-diamine | 278 | 0.64 |

Reference Example 17

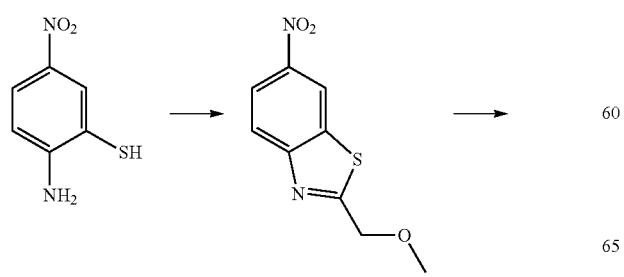

-continued

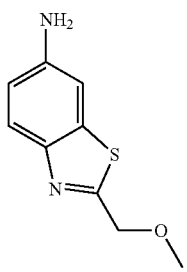

(1)

To a solution of 2-amino-5-nitrobenzenethiol (500 mg) in NMP (2 mL) was added methoxyacetyl chloride (381 mg), and the mixture was stirred at room temperature for 20 minutes. The mixture was stirred at 100° C. for 20 minutes. The reaction mixture was cooled to room temperature, and then water was added thereto. The precipitate was collected by filtration to obtain 2-(methoxymethyl)-6-nitrobenzo[d]thiazole (583 mg).

MS (ESI m/z): 225 (M+H)

RT (min): 1.27

(2)

In the same manner as in Reference Example 15-(2), the following compound was obtained.

2-(Methoxymethyl)benzo[d]thiazol-6-amine

MS (ESI m/z): 195 (M+H)

RT (min): 0.62

Reference Example 18

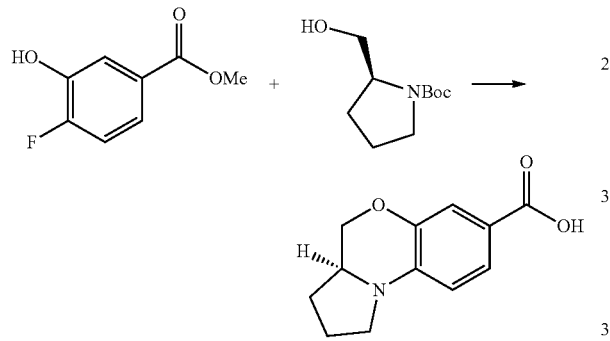

In the same manner as in Reference Example 9, the following compound was obtained.

(S)-2,3,3a,4-Tetrahydro-1H-benzo[b]pyrrolo[1,2-d][1,4]oxazine-7-carboxylic acid

MS (ESI m/z): 220 (M+H)

RT (min): 1.13

Reference Example 19

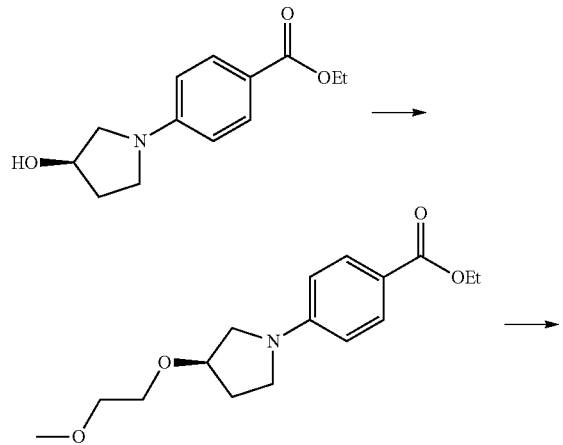

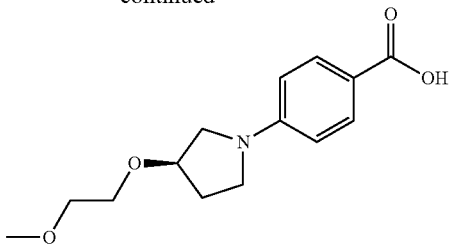

In the same manner as in Reference Examples 7-(2) and 7-(3), the following compound was obtained.

(R)-4-(3-(2-Methoxyethoxy)pyrrolidin-1-yl)benzoic acid

MS (ESI m/z): 266 (M+H)

RT (min): 1.04

Reference Example 20

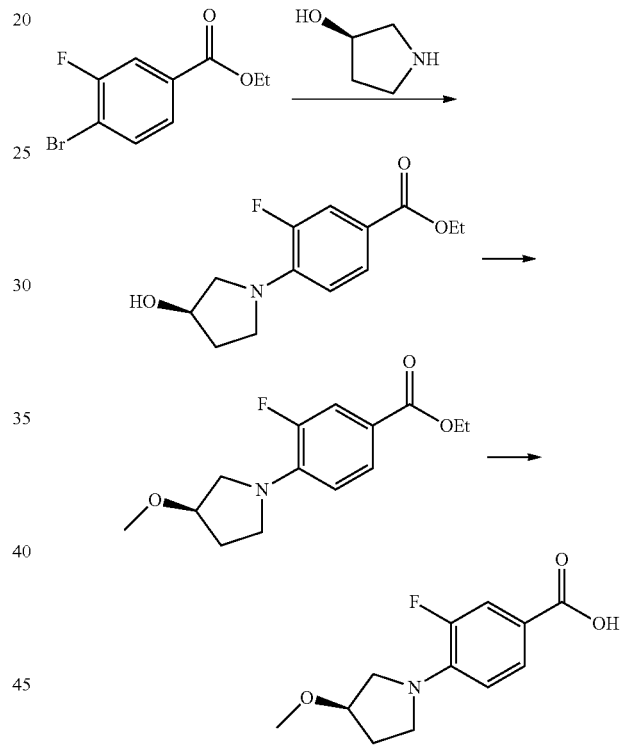

(1)

A mixture of ethyl 4-bromo-3-fluorobenzoate (500 mg), tris(dibenzylideneacetone)dipalladium (0) (94 mg), (R)-(+)-(1,1'-binaphthalene-2,2'-diyl)bis(diphenylphosphine) (189 mg), cesium carbonate (1.98 g), (R)-pyrrolidin-3-ol (353 mg), and toluene (5 mL) was stirred for 1 hour under heating and refluxing. The reaction mixture was cooled to room temperature and then the solvent was evaporated under reduced pressure. The obtained residue was purified by silica gel column chromatography [eluent; 70%-30% n-hexane/ethyl acetate] to obtain ethyl (R)-3-fluoro-4-(3-hydroxypyrrolidin-1-yl)benzoate (390 mg) as a brown oily substance.

MS (ESI nm/z): 254 (M+H)

RT (min): 1.41

(2)

In the same manner as in Reference Examples 7-(2) and 7-(3), the following compound was obtained.

(R)-3-Fluoro-4-(3-methoxypyrrolidin-1-yl)benzoic acid

MS (ESI m/z): 240 (M+H)

RT (min): 1.14

Reference Examples 21-1 to 21-3

In the same manner as in Reference Example 2, the following compounds were obtained.

TABLE 4

| Reference Example No. | | | MS (ESI m/z) (M + H) | RT(min) |
|---|---|---|---|---|
| 21-1 | 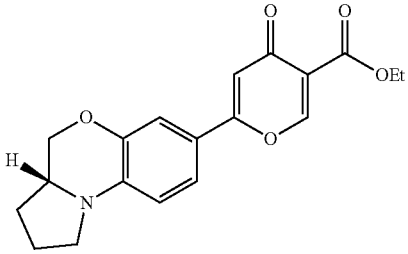 [SMILES: CCOC(=O)c1coc(-c2ccc3c(c2)OC[C@H]2CCCN32)cc1=O] | ethyl (S)-4-oxo-6-(2,3,3a,4-tetrahydro-1H-benzo[b]pyrrolo-[1,2-d][1,4]-oxadin-7-yl)-4H-pyran-3-carboxylate | 342 | 1.56 |
| 21-2 | 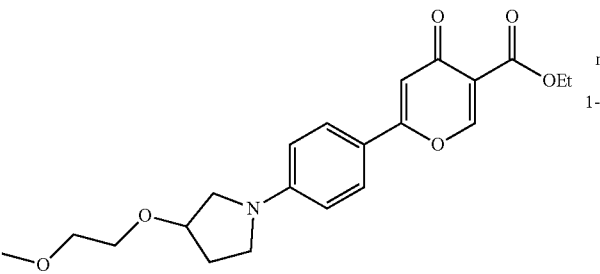 | ethyl (R)-6-(4-(3-(2-methoxyethoxy)-pyrrolidin-1-yl)phenyl)-4-oxo-4H-pyran-3-carboxylate | 388 | 1.28 |
| 21-3 | 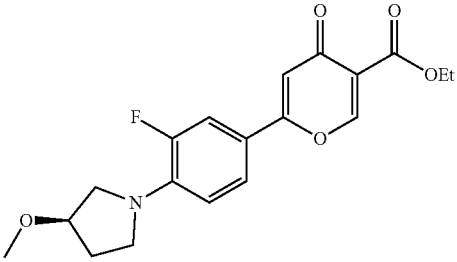 [SMILES: CCOC(=O)c1coc(-c2ccc(N3CC[C@@H](OC)C3)c(F)c2)cc1=O] | ethyl (R)-6-(3-fluoro-4-(3-methoxypyrrolidin-1-yl)phenyl)-4-oxo-4H-pyran-3-carboxylate | 362 | 1.38 |

Reference Examples 22-1 to 22-6

In the same manner as in Reference Example 15, the following compounds were obtained.

TABLE 5

| Reference Example No. | | | MS (ESI m/z) (M + H) | RT(min) |
|---|---|---|---|---|
| 22-1 | 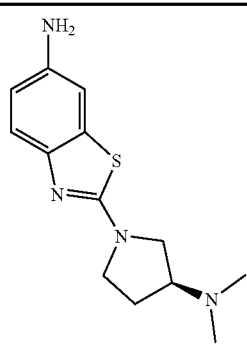 | (S)-2-(3-(dimethylamine)pyrrolidin-1-yl)benzo[d]thiazol-6-amine | 263 | 0.24 |

TABLE 5-continued
| Reference Example No. | | | MS (ESI m/z) (M + H) | RT(min) |
|---|---|---|---|---|
| 22-2 | 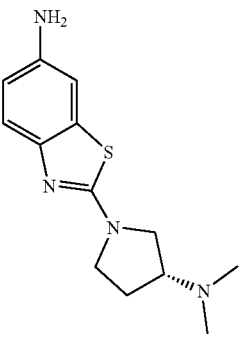 [SMILES: CN(C)[C@@H]1CCN(c2nc3ccc(N)cc3s2)C1] | (R)-2-(3-(dimethylamine)pyrrolidin-1-yl)benzo[d]thiazol-6-amine | 263 | 0.24 |
| 22-3 | 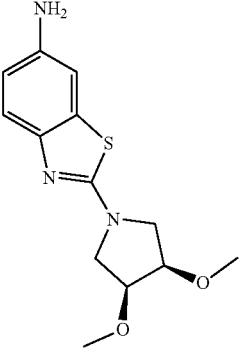 [SMILES: CO[C@H]1CN(c2nc3ccc(N)cc3s2)C[C@H]1OC] | 2-((3R,4R)-3,4-dimethoxypyrrolidin-1-yl)benzo[d]thiazol-6-amine | 280 | 0.53 |
| 22-4 | 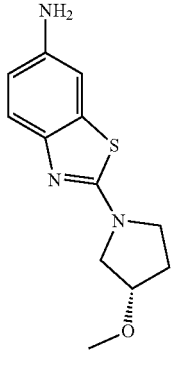 [SMILES: CO[C@H]1CCN(c2nc3ccc(N)cc3s2)C1] | (S)-2-(3-methoxypyrrolidin-1-yl)benzo[d]thiazol-6-amine | 250 | 0.55 |
| 22-5 | 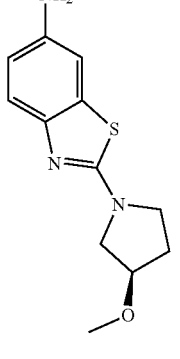 | (R)-2-(3-methoxypyrrolidin-1-yl)benzo[d]thiazol-6-amine | 250 | 0.55 |

TABLE 5-continued

| Reference Example No. | | | MS (ESI m/z) (M + H) | RT(min) |
|---|---|---|---|---|
| 22-6 | 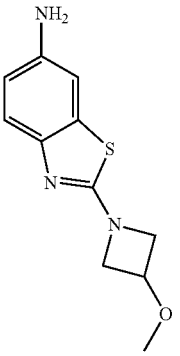 [SMILES: COC1CN(c2nc3ccc(N)cc3s2)C1] | 2-(3-methoxyazetidin-1-yl)benzo[d]thiazol-6-amine | 236 | 0.62 |

Reference Examples 23-1 to 23-8

In the same manner as in Reference Example 15, the following compounds were obtained.

TABLE 6

| Reference Example No. | | | MS (ESI m/z) (M + H) | RT(min) |
|---|---|---|---|---|
| 23-1 | 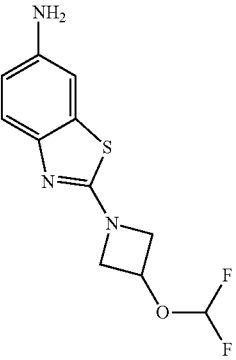 [SMILES: Nc1ccc2nc(N3CC(OC(F)F)C3)sc2c1] | 2-(3-(difluoromethoxy)azetidin-1-yl)benzo[d]thiazol-6-amine | 272 | 0.70 |
| 23-2 | 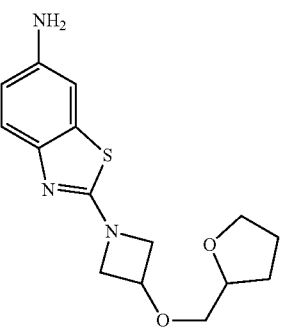 [SMILES: Nc1ccc2nc(N3CC(OCC4CCCO4)C3)sc2c1] | 2-(3-((tetrahydrofuran-2-yl)methoxy)azetidin-1-yl)benzo[d]thiazol-6-amine | 306 | 0.69 |

TABLE 6-continued
| Reference Example No. | | | MS (ESI m/z) (M + H) | RT(min) |
|---|---|---|---|---|
| 23-3 | 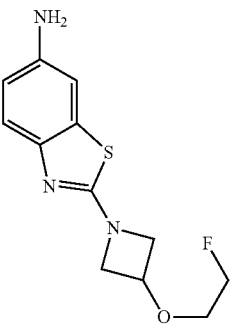 [SMILES: Nc1ccc2nc(N3CC(OCCF)C3)sc2c1] | 2-(3-(2-fluoroethoxy)azetidin-1-yl)benzo[d]thiazol-6-amine | 268 | 0.58 |
| 23-4 | 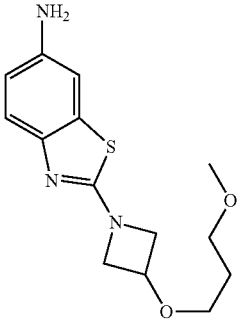 [SMILES: COCCCOC1CN(c2nc3ccc(N)cc3s2)C1] | 2-(3-(3-methoxypropoxy)azetidin-1-yl)benzo[d]thiazol-6-amine | 294 | 0.69 |
| 23-5 | 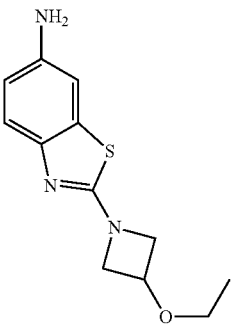 [SMILES: CCOC1CN(c2nc3ccc(N)cc3s2)C1] | 2-(3-ethoxyazetidin-1-yl)benzo[d]thiazol-6-amine | 250 | 0.64 |
| 23-6 | 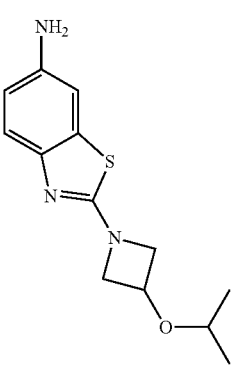 [SMILES: CC(C)OC1CN(c2nc3ccc(N)cc3s2)C1] | 2-(3-isopropoxyazetidin-1-yl)benzo[d]thiazol-6-amine | 264 | 0.74 |

TABLE 6-continued

| Reference Example No. | | | MS (ESI m/z) (M + H) | RT(min) |
|---|---|---|---|---|
| 23-7 | 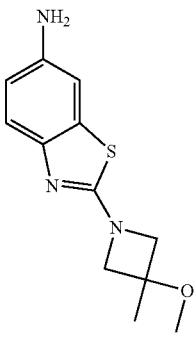 [SMILES: COC1(C)CN(c2nc3ccc(N)cc3s2)C1] | 2-(3-methoxy-3-methylazetidin-1-yl)benzo[d]thiazol-6-amine | 250 | 0.62 |
| 23-8 | 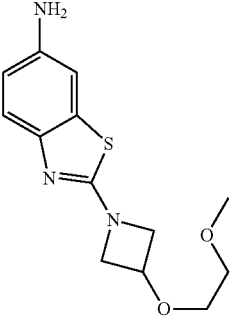 [SMILES: COCCOC1CN(c2nc3ccc(N)cc3s2)C1] | 2-(3-(2-methoxyethoxy)azetidin-1-yl)benzo[d]thiazol-6-amine | 280 | 0.59 |

Reference Example 24

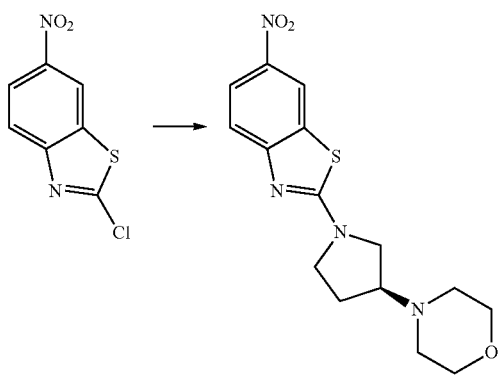 [SMILES: O=[N+]([O-])c1ccc2nc(Cl)sc2c1 ; O=[N+]([O-])c1ccc2nc(N3CC[C@H](N4CCOCC4)C3)sc2c1]

To a mixture of (R)-pyrrolidin-3-ol (1.08 g), triethylamine (2.41 g), and NMP (10 mL) was added 2-chloro-6-nitrobenzo[d]thiazole (2.02 g) under ice-cooling. The mixture was warmed to room temperature and stirred for 1 hour, a saturated aqueous sodium chloride solution was added thereto and the mixture was extracted with ethyl acetate. The organic layer was collected by separation and then the aqueous layer was extracted with chloroform. The organic layer and the extract were combined and the solvent was evaporated under reduced pressure.

To the obtained residue was added pyridine (10 mL), the mixture was cooled to be under ice-cooling, and chloromethylsulfonyl chloride (1.25 mL) was added thereto. The reaction mixture was warmed and stirred at room temperature for 1 hour, and then chloromethylsulfonyl chloride (0.2 mL) was added thereto under ice-cooling. The reaction mixture was warmed, the mixture was stirred at room temperature for 1 hour stirred, and then water was added thereto. The solvent was evaporated under reduced pressure, and then ethyl acetate and a saturated aqueous sodium hydrogen carbonate solution were added thereto. The organic layer was collected by separation and then washed with a saturated aqueous sodium hydrogen carbonate solution and saturated saline. The aqueous layer was extracted with toluene. The organic layer and the extract were combined and dried by the addition of anhydrous sodium sulfate, and then the solvent was evaporated under reduced pressure.

A mixture of the obtained residue, DMF (6 mL), morpholine (2.5 mL), and potassium carbonate (1.93 g) was stirred at 110° C. for 1.5 hours. The reaction mixture was cooled to room temperature, and water and ethyl acetate were added thereto. The precipitate was collected by filtration, the organic layer of the filtrate was collected by separation, and the aqueous layer was extracted with ethyl acetate. The precipitate collected by filtration, the organic layer, and the extract were combined, and the solvent was evaporated under reduced pressure.

To a mixture of the obtained residue, ethanol (12 mL), and acetic acid (4 mL) was added powder zinc (3.05 g) under ice-cooling, and the mixture was stirred for 1 hour. The insoluble matters of the reaction mixture were removed by filtration using Celite (registered trademark) and the solvent was evaporated under reduced pressure. The obtained residue was purified by silica gel column chromatography [eluent; 100%-0% hexane/ethyl acetate→100%-90% ethyl acetate/methanol NH silica] to obtain (S)-2-(3-morpholino-pyrrolidin-1-yl)benzo[d]thiazol-6-amine (1.02 g) as a brown solid.

MS (ESI m/z): 305 (M+H)
RT (min): 0.20

Reference Example 25

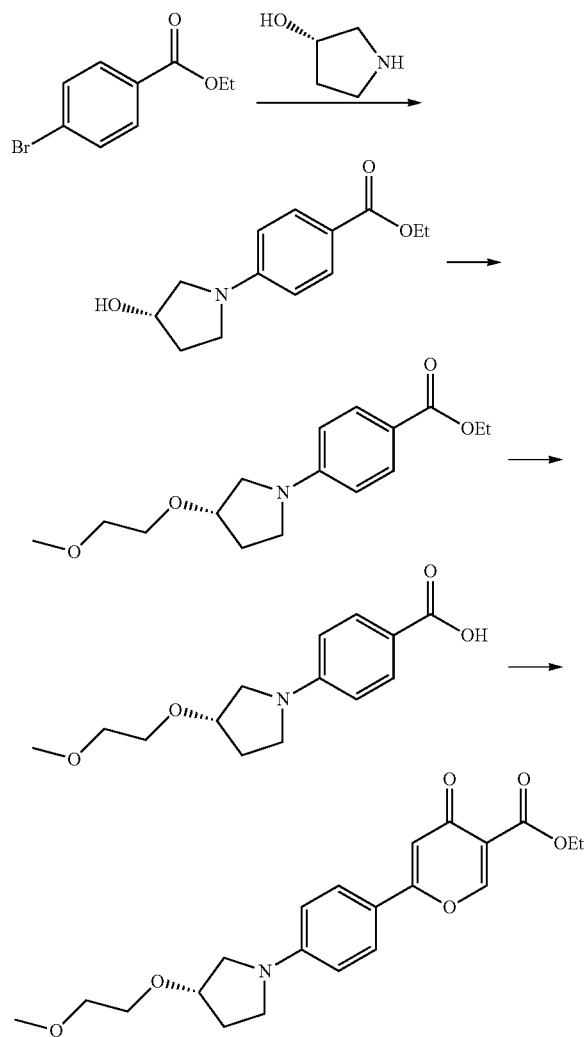

In the same manner as in Reference Example 7 and Reference Example 2, the following compound was obtained.

Ethyl (S)-6-(4-(3-(2-methoxyethoxy)pyrrolidin-1-yl)phenyl)-4-oxo-41H-pyran-3-carboxylate MS (ESI m/z): 388 (M+H)

RT (min): 1.29

Example 1

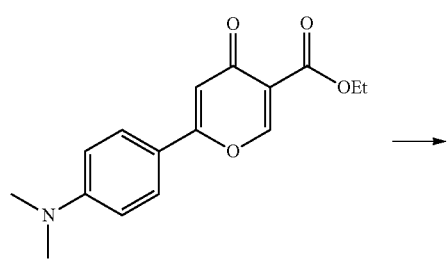

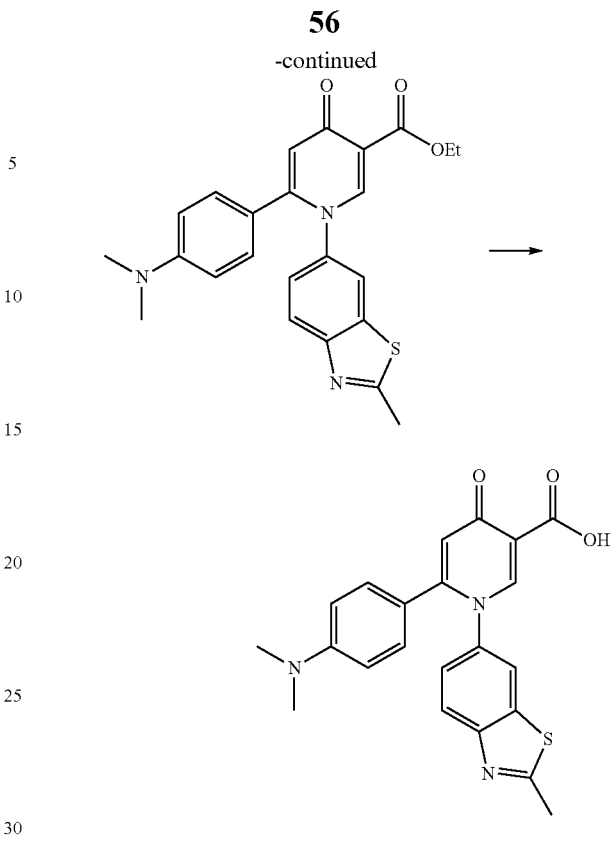

(1)

A mixture of ethyl 6-(4-(dimethylamino)phenyl)-4-oxo-4H-pyran-3-carboxylate obtained in Reference Example 1 (40 mg), 6-amino-2-methylbenzothiazole (46 mg), ethanol (3 mL) and acetic acid (1 mL) was irradiated with microwaves (Initiator™, 150° C., 30 minutes, 2.45 GHz, 0-240 W). The reaction mixture was cooled to room temperature and then the solvent was evaporated under reduced pressure. The obtained residue was purified by silica gel column chromatography [eluent; 50%-0% hexane/ethyl acetate→100%-75% ethyl acetate/methanol] to obtain ethyl 6-(4-(dimethylamino)phenyl)-1-(2-methylbenzo[d]thiazol-6-yl)-4-oxo-1,4-dihydropyridine-3-carboxylate (14 mg) as a brown oily substance.

MS (ESI m/z): 434 (M+H)

RT (min): 1.24

(2)

To ethyl 6-(4-(dimethylamino)phenyl)-4-oxo-4H-pyran-3-carboxylate obtained in (1) were added methanol (1 mL) and a 1 mol/L aqueous sodium hydroxide solution (1 mL), and the mixture was stirred at room temperature for 1 hour. To the reaction mixture was added 1 mol/L hydrochloric acid, and the precipitate was collected by filtration to obtain 6-(4-(dimethyl amino)phenyl)-1-(2-methylbenzo[d]thiazol-6-yl)-4-oxo-1,4-dihydropyridine-3-carboxylic acid (8.9 mg) as a pale yellow solid.

$^1$H-NMR (CDCl$_3$) δ: 8.69 (1H, s), 7.87 (1H, d, J=8.6 Hz), 7.72 (1H, d, J=2.0 Hz), 7.15 (1H, dd, J=8.6, 2.0 Hz), 6.95 (2H, d, J=9.2 Hz), 6.82 (1H, s), 6.46 (2H, d, J=9.2 Hz), 2.93 (6H, s), 2.87 (3H, s).

MS (ESI m/z): 406 (M+H)

RT (min): 1.28

Example 2

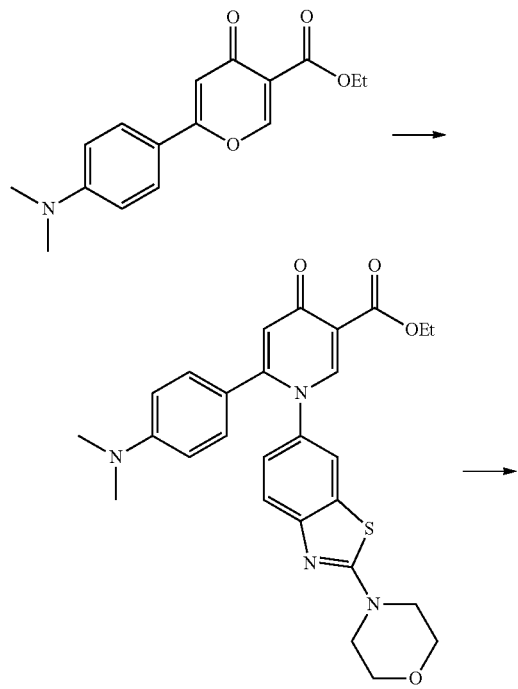

In the same manner as in Examples 1-(1) and 1-(2), the following compound was obtained. 6-(4-(Dimethylamino)phenyl)-1-(2-morpholinobenzo[d]thiazol-6-yl)-4-oxo-1,4-dihydropyridine-3-carboxylic acid MS (ESI m/z): 477 (M+H)
RT (min): 1.31

Examples 3-1 to 3-20

In the same manner as in Examples 1-(1) and 1-(2), the following compounds were obtained.

TABLE 7

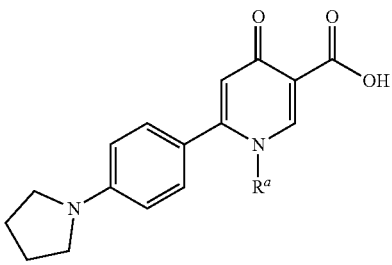

| Example No. | *─Rᵃ | | MS (ESI m/z) (M + H) | RT (min) | ¹H-NMR(300 MHz) |
|---|---|---|---|---|---|
| 3-1 | (benzo[d]thiazol-6-yl) | 1-(benzo[d]thiazol-6-yl)-4-oxo-6-(4-(pyrrolidin-1-yl)phenyl)-1,4-dihydropyridine-3-carboxylic acid | 418 | 1.39 | (DMSO-D6) δ: 9.50 (1H, s), 8.55 (1H, s), 8.41 (1H, d, J = 2.0 Hz), 8.05 (1H, d, J = 8.6 Hz), 7.46 (1H, dd, J = 8.9, 2.3 Hz), 7.04 (2H, d, J = 8.6 Hz), 6.68 (1H, s), 6.35 (2H, d, J = 8.6 Hz), 3.19-3.08 (4H, m), 1.96-1.80 (4H, m). |
| 3-2 | (2-methylbenzo[d]thiazol-6-yl) | 1-(2-methylbenzo[d]thiazol-6-yl)-4-oxo-6-(4-(pyrrolidin-1-yl)phenyl)-1,4-dihydropyridine-3-carboxylic acid | 432 | 1.47 | (DMSO-D6) δ: 8.57 (1H, s), 8.27 (1H, d, J = 2.0 Hz), 7.87 (1H, d, J = 8.6 Hz), 7.41 (1H, dd, J = 8.6, 2.0 Hz), 7.04 (2H, d, J = 8.6 Hz), 6.73 (1H, s), 6.35 (2H, d, J = 8.6 Hz), 3.20-3.08 (4H, m), 2.81 (3H, s), 1.94-1.83 (4H, m). |

TABLE 7-continued

| Example No. | *~R^a | R^a | MS (ESI m/z) (M + H) | RT (min) | ¹H-NMR(300 MHz) |
|---|---|---|---|---|---|
| 3-3 | (6-benzo[d]thiazolyl with 2-pyrrolidin-1-yl) | 4-oxo-1-(2-(pyrrolidin-1-yl)benzo[d]thiazol-6-yl)-6-(4-(pyrrolidin-1-yl)phenyl)-1,4-dihydropyridine-3-carboxylic acid | 487 | 1.54 | (DMSO-D6) δ: 8.50 (1H, s), 7.92 (1H, d, J = 2.0 Hz), 7.37 (1H, d, J = 8.6 Hz), 7.22 (1H, dd, J = 8.6, 2.0 Hz), 7.04 (2H, d, J = 8.6 Hz), 6.72 (1H, s), 6.36 (2H, d, J = 8.6 Hz), 3.59-3.43 (4H, m), 3.21-3.09 (4H, m), 2.06-1.95 (4H, m), 1.94-1.84 (4H, m). |
| 3-4 | (6-benzo[d]thiazolyl with 2-morpholine) | 1-(2-morpholinebenzo[d]thiazol-6-yl)-4-oxo-6-(4-(pyrrolidin-1-yl)phenyl)-1,4-dihydropyridine-3-carboxylic acid | 503 | 1.48 | (DMSO-D6) δ: 8.52 (1H, s), 7.97 (1H, d, J = 2.0 Hz), 7.40 (1H, d, J = 8.6 Hz), 7.26 (1H, dd, J = 8.6, 2.0 Hz), 7.04 (2H, d J = 8.6 Hz), 6.74 (1H, s), 6.37 (2H, d, J = 8.6 Hz), 3.78-3.68 (4H, m), 3.61-3.50 (4H, m), 3.21-3.11 (4H, m), 1.95-1.83 (4H, m). |
| 3-5 | (6-benzo[d]thiazolyl with 2-methoxy) | 1-(2-methoxybenzo[d]thiazol-6-yl)-4-oxo-6-(4-(pyrrolidin-1-yl)phenyl)-1,4-dihydropyridine-3-carboxylic acid | 448 | 1.58 | (DMSO-D6) δ: 8.57 (1H, s), 8.10 (1H, d, J = 2.0 Hz), 7.66 (1H, d, J = 8.6 Hz), 7.38 (1H, dd, J = 8.6, 2.0 Hz), 7.05 (2H, d, J = 8.6 Hz), 6.77 (1H, s), 6.37 (2H, d, J = 8.6 Hz), 4.17 (3H, s), 3.21-3.11 (4H, m), 1.95-1.83 (4H, m). |
| 3-6 | (6-benzo[d]thiazolyl with 2-bis(2-methoxyethyl)amino) | 1-(2-(bis(2-methoxyethyl)amino)benzo[d]thiazol-6-yl)-4-oxo-6-(4-(pyrrolidin-1-yl)phenyl)-1,4-dihydropyridine-3-carboxylic acid | 549 | 1.59 | (DMSO-D6) δ: 8.09 (1H, s), 7.81 (1H, d, J = 2.0 Hz), 7.31 (1H, d, J = 8.6 Hz), 7.05 (1H, dd, J = 8.6, 2.0 Hz), 6.99 (2H, d, J = 8.6 Hz), 5.36 (2H, d, J = 8.6 Hz), 6.18 (1H, s), 3.74-3.23 (14H, m), 3.19-3.12 (4H, m), 1.92-1.85 (4H, m). |

TABLE 7-continued

| Example No. | *~Rᵃ | Rᵃ | MS (ESI m/z) (M + H) | RT (min) | ¹H-NMR(300 MHz) |
|---|---|---|---|---|---|
| 3-7 | (benzothiazole with N-ethyl, N-(2-methoxyethyl)amino substituent) | 1-(2-(ethyl(2-methoxyethyl)amino)benzo[d]thiazol-6-yl)-4-oxo-6-(4-(pyrrolidin-1-yl)phenyl)-1,4-dihydropyridine-3-carboxylic acid | 519 | 1.53 | (DMSO-D6) : 8.13 (1H, s), 7.81 (1H, d, J = 2.3 Hz), 7.31 (1H, d, J = 8.6 Hz), 7.05 (1H, dd, J = 8.6, 2.3 Hz), 6.99 (2H, d, J = 8.6 Hz), 6.36 (2H, d, J = 8.6 Hz), 6.17 (1H, s), 3.71-3.50 (6H, m), 3.27 (3H, s), 3.18-3.12 (4H, m), 1.92-1.85 (4H, m), 1.19 (3H, t, J = 7.1 Hz). |
| 3-8 | (benzothiazole with 4-methoxypiperidin-1-yl substituent) | 1-(2-(4-methoxypiperidin-1-yl)benzo[d]thiazol-6-yl)-4-oxo-6-(4-(pyrrolidin-1-yl)phenyl)-1,4-dihydropyridine-3-carboxylic acid | 531 | 1.59 | (DMSO-D6) δ: 8.13 (1H, s), 7.81 (1H, d, J = 2.2 Hz), 7.32 (1H, d, J = 8.6 Hz), 7.07 (1H, dd, J = 8.6, 2.2 Hz), 6.98 (2H, d, J = 8.6 Hz), 6.35 (2H, d, J = 8.6 Hz), 6.17 (1H, s), 3.82-3.70 (2H, m), 3.52-3.30 (3H, m), 3.28 (3H, s), 3.18-3.10 (4H, m), 1.99-1.84 (6H, m), 1.61-1.47 (2H, m). |
| 3-9 | (benzothiazole with 4-ethylpiperazin-1-yl substituent) | 1-(2-(4-ethylpiperazin-1-yl)benzo[d]thiazol-6-yl)-4-oxo-6-(4-(pyrrolidin-1-yl)phenyl)-1,4-dihydropyridine-3-carboxylic acid | 530 | 1.11 | (DMSO-D6) δ: 8.15 (1H, s), 7.83 (1H, d, J = 2.2 Hz), 7.34 (1H, d, J = 8.6 Hz), 7.09 (1H, dd, J = 8.6, 2.2 Hz), 6.98 (2H, c, J = 8.6 Hz), 6.34 (2H, d, J = 8.6 Hz), 6.18 (1H, s), 3.60-3.48 (4H, m), 3.43-3.24 (4H, m), 3.19-3.10 (4H, m), 2.38 (2H, a, J = 7.2 Hz), 1.93-1.82 (4H, m), 1.02 (3H, t, J = 7.2 Hz). |
| 3-10 | (benzothiazole with (R)-2-(methoxymethyl)pyrrolidin-1-yl substituent) | (R)-1-(2-(2-(methoxymethyl)pyrrolidin-1-yl)benzo[d]thiazol-6-yl)-4-oxo-6-(4-(pyrrolidin-1-yl)phenyl)-1,4-dihydropyridine-3-carboxylic acid | 531 | 1.54 | (DMSO-D6) δ: 8.11 (1H, s), 7.83 (1H, d, J = 2.3 Hz), 7.36 (1H, d, J = 8.6 Hz), 707 (1H, dd, J = 86, 23 Hz), 6.98 (2H, d, J = 8.6 Hz), 6.35 (2H, d, J = 8.6 Hz), 6.16 (1H, s), 4.15-4.03 (1H, m), 3.56-3.32 (4H, m), 3.28 (3H, s), 3.20-3.10 (4H, m), 2.12-1.83 (8H, m). |

TABLE 8

| Example No. | *–Rª | | MS (ESI m/z) (M + H) | RT (min) | ¹H-MMR(300 MHz) |
|---|---|---|---|---|---|
| 3-11 | (6-benzothiazolyl with 2-(4-methyl-1,4-diazepan-1-yl) substituent) | 1-(2-(4-methyl-1,4-diazepan-1-yl)benzo[d]thiazol-6-yl)-4-oxo-6-(4-(pyrrolidin-1-yl)phenyl)-1,4-dihydropyridine-3-carboxylic acid | 530 | 1.09 | (DMSO-D6) δ: 8.11 (1H, s), 7.81 (1H, d, J = 2.3 Hz), 7.31 (1H, d, J = 8.6 Hz), 7.06 (1H, dd, J = 8.6, 2.3 Hz), 6.99 (2H, d, J = 8.6 Hz), 6.35 (2H, d, J = 8.6 Hz), 6.16 (1H, s), 3.79-3.56 (4H, m), 3.38-3.25 (2H, m), 3.20-3.08 (4H, m), 2.70-2.61 (2H, m), 2.26 (3H, s), 2.00-1.82 (6H, m). |
| 3-12 | (6-benzothiazolyl with 2-((pyridin-2-ylmethyl)amino) substituent) | 4-oxo-1-(2-((pyridin-2-ylmethyl)amino)benzo[d]thiazol-6-yl)-6-(4-(pyrrolidin-1-yl)phenyl)-1,4-dihydropyridine-3-carboxylic acid | 524 | 1.24 | |
| 3-13 | (6-benzothiazolyl with 2-((pyrimidin-2-ylmethyl)amino) substituent) | 4-oxo-1-(2-((pyrimidin-2-ylmethyl)amino)benzo[d]thiazol-6-yl)-6-(4-(pyrrolidin-1-yl)phenyl)-1,4-dihydropyridine-3-carboxylic acid | 525 | 1.30 | |
| 3-14 | (6-benzothiazolyl with 2-(4-(2-methoxyethyl)piperazin-1-yl) substituent) | 1-(2-(4-(2-methoxyethyl)piperazin-1-yl)benzo[d]thiazol-6-yl)-4-oxo-6-(4-(pyrrolidin-1-yl)phenyl)-1,4-dihydropyridine-3-carboxylic acid | 560 | 1.11 | |
| 3-15 | (6-benzothiazolyl with 2-(methyl((tetrahydro-2H-pyran-4-yl)methyl)amino) substituent) | 1-(2-(methyl((tetrahydro-2H-pyran-4-yl)methyl)amino)benzo[d]thiazol-6-yl)-4-oxo-6-(4-(pyrrolidin-1-yl)phenyl)-1,4-dihydropyridine-3-carboxylic acid | 545 | 1.53 | |

TABLE 8-continued

| Example No. | *-R<sup>a</sup> | Name | MS (ESI m/z) (M + H) | RT (min) | ¹H-MMR(300 MHz) |
|---|---|---|---|---|---|
| 3-16 | 2-(methoxymethyl)benzo[d]thiazol-6-yl (structure) | 1-(2-(methoxymethyl)benzo[d]thiazol-6-yl)-4-oxo-6-(4-(pyrrolidin-1-yl)phenyl)-1,4-dihydropyridine-3-carboxylic acid | 452 | 1.50 | (CDCl3) δ: 8.69 (1H, s), 7.93 (1H, d, J = 8.6 Hz), 7.79 (1H, d, J = 2.0 Hz), 7.20 (1H, dd, J = 8.6, 2.0 Hz), 6.93 (2H, d, J = 8.6 Hz), 6.82 (1H, s), 6.31 (2H, d, J = 8.6 Hz), 4.86 (2H, s), 3.58 (3H, s), 3.27-3.16 (4H, m), 2.02-1.93 (4H, m). |
| 3-17 | 2,5-dimethylbenzo[d]thiazol-6-yl (structure) | 1-(2,5-dimethylbenzo[d]thiazol-6-yl)-4-oxo-6-(4-(pyrrolidin-1-yl)phenyl)-1,4-dihydropyridine-3-carboxylic acid | 446 | 1.52 | (DMSO-D6) δ: 8.53 (1H, s), 8.42 (1H, s), 7.76 (1H, s), 7.09 (2H, d, J = 8.6 Hz), 6.79 (1H, s), 6.33 (2H, d, J = 8.6 Hz), 3.19-3.08 (4H, m), 2.82 (3H, s), 1.98 (3H, s), 1.93-1.82 (4H, m). |
| 3-18 | benzo[d]thiazol-4-yl (structure) | 1-(benzo[d]thiazole-4-yl)-4-oxo-6-(4-(pyrrolidin-1-yl)phenyl)-1,4-dihydropyridine-3-carboxylic acid | 418 | 1.42 | (DMSO-D6) δ: 9.39 (1H, s), 8.65 (1H, s), 8.17 (1H, d, J = 7.9 Hz), 7.89 (1H, d, J = 7.9 Hz), 7.69 (1H, dd, J = 7.9, 7.9 Hz), 7.07 (2H, d, J = 9.2 Hz), 6.83 (1H, s), 6.27 (2H, d, J = 9.2 Hz), 3.14-3.07 (4H, m), 1.90-1.82 (4H, m). |
| 3-19 | benzo[d]thiazol-7-yl (structure) | 1-(benzo[d]thiazol-7-yl)-4-oxo-6-(4-(pyrrolidin-1-yl)phenyl)-1,4-dihydropyridine-3-carboxylic acid | 418 | 1.42 | (DMSO-D6) δ: 9.39 (1H, s), 8.65 (1H, s), 8.17 (1H, d, J = 7.9 Hz), 7.89 (1H, d, J = 7.9 Hz), 7.69 (1H, dd, J = 7.9, 7.9 Hz), 7.07 (2H, d, J = 8.6 Hz), 6.83 (1H, s), 5.27 (2H, d, J = 8.6 Hz), 3.13-3.06 (4H, m), 1.91-1.82 (4H, m). |
| 3-20 | 2-methylbenzo[d]thiazol-5-yl (structure) | 1-(2-methylbenzo[d]thiazol-5-yl)-4-oxo-6-(4-(pyrrolidin-1-yl)phenyl)-1,4-dihydropyridine-3-caxboxylic acid | 432 | 1.49 | 1H-NMR (DMSO-D6) δ: 8.57 (1H, s), 8.09 (1H, s), 8.06 (1H, d, J = 8.6 Hz), 7.41 (1H, d, J = 8.6 Hz), 7.05 (2H, d, J = 8.6 Hz), 6.75 (1H, s), 6.35 (2H, d, J = 8.6 Hz), 3.20-3.08 (4H, m), 2.80 (3H, s), 1.95-1.81 (4H, m). |

Examples 4-1 to 4-5

In the same manner as in Examples 1-(1) and 1-(2), the following compounds were obtained.

TABLE 9

| Example No. | *~R$^a$ | | MS (ESI m/z) (M + H) | RT (min) | $^1$H-NMR(300 MHz) |
|---|---|---|---|---|---|
| 4-1 | (2-methylbenzo[d]thiazol-6-yl) | 6-(3-methoxy-4-(pyrrolidin-1-yl)phenyl-1)-(2-methylbenzo[d]thiazol-6-yl)-4-oxo-1,4-dihydropyridine-3-carboxylic acid | 462 | 1.27 | (DMSO-D6) : 8.63 (1H, s), 8.28 (1H, d, J = 2.3 Hz), 7.89 (1H, d, J = 8.6 Hz), 7.45 (1H, dd, J = 8.6, 2.3 Hz), 6.86 (1H, s), 6.78 (1H, dd, J = 8.6, 2.3 Hz), 6.66-6.65 (1H, m), 6.44 (1H, d, J = 8.6 Hz), 3.51-3.18 (7H, m), 2.81 (3H, s), 1.80-1.74 (4H, m). |
| 4-2 | (2-morpholinobenzo[d]thiazol-6-yl) | 6-(3-methoxy-4-(pyrrolidin-1-yl)phenyl)-1-(2-morpholinobenzo[d]thiazol-6-yl)-4-oxo-1,4-dihydropyridine-3-carboxylic acid | 533 | 1.24 | (DMSO-D6) δ: 8.57 (1H, s), 7.99 (1H, d, J = 2.3 Hz), 7.42 (1H, d, J = 8.6 Hz), 7.30 (1H, dd, J = 8.6, 2.3 Hz), 6.85 (1H, s), 6.78 (1H, dd, J = 8.6, 2.0 Hz), 6.67 (1H, d, J = 2.0 Hz), 6.46 (1H, d, J = 8.6 Hz), 3.75-3.68 (4H, m), 3.58-3.53 (4H, m), 3.48-3.21 (7H, m), 1.82-1.75 (4H, m). |
| 4-3 | (2-(bis(2-methoxyethyl)amino)benzo[d]thiazol-6-yl) | 1-(2-(bis(2-methoxyethyl)amino)benzo[d]thiazol-6-yl)-6-(3-methoxy-4-(pyrrolidin-1-yl)phenyl)-4-oxo-1,4-dihydropyridine-3-carboxylic acid | 579 | 1.39 | (DMSO-D6) δ: 8.55 (1H, s), 7.95 (1H, d, J = 2.0 Hz), 7.36 (1H, d, J = 8.6 Hz), 7.24 (1H, dd, J = 8.6, 2.0 Hz), 6.84 (1H, s), 6.77 (1H, dd, J = 8.3, 2.0 Hz) 6.71 (1H, d, J = 2.0 Hz), 6.46 (1H, d, J = 8.3 Hz), 3.78-3.05 (21H, m), 1.81-1.75 (4H, m). |
| 4-4 | (2-(4-(2-methoxyethyl)piperazin-1-yl)benzo[d]thiazol-6-yl) | 6-(3-methoxy-4-(pyrrolidin-1-yl)phenyl)-1-(2-(4-(2-methoxyethyl)piperazin-1-yl)benzo[d]thiazol-6-yl)-4-oxo-1,4-dihydropyridine-3-carboxylic acid | 590 | 0.95 | (DMSO-D6) δ: 8.54 (1H, s), 8.09 (1H, br s), 7.85 (1H, s), 7.35 (1H, d, J = 8.6 Hz), 7.20-7.08 (1H, m), 6.72 (1H, dd, J = 8.6, 2.0 Hz), 6.62 (1H, d, J = 2.0 Hz), 6.45 (1H, d, J = 8.6 Hz), 3.51-3.20 (20H, m), 2.59-2.47 (2H, m), 1.82-1.75 (4H, m). |

TABLE 9-continued

| Example No. | *—Rᵃ | | MS (ESI m/z) (M + H) | RT (min) | ¹H-NMR(300 MHz) |
|---|---|---|---|---|---|
| 4-5 | [benzothiazole with (R)-2-(methoxymethyl)pyrrolidin-1-yl substituent] | (R)-6-(3-methoxy-4-(pyrrolidin-1-yl)phenyl)-1-(2-(2-(methoxymethyl)pyrrolidin-1-yl)benzo[d]thiazol-6-yl)-4-oxo-1,4-dihydropyridine-3-carboxylic acid | 561 | 1.47 | (CDCl3) δ: 8.68 (1H, s), 7.46 (1H, d, J = 8.6 Hz), 7.39 (1H, d, J = 2.0 Hz), 7.03 (1H, d, J = 8.6, 2.0 Hz), 6.84 (1H, s), 6.70 (1H, dd, J = 7.9, 2.0 Hz), 6.48 (1H, d, J = 7.9 Hz), 6.46 (1H, d, J = 2.0 Hz), 4.27-4.10 (1H, m), 3.70-3.44 (7H, m), 3.39 (3H, s), 3.36-3.28 (4H, m), 2.26-1.39 (4H, m), 1.95-1.84 (4H, m). |

Examples 5-1 to 5-6

In the same manner as in Examples 1-(1) and 1-(2), the following compounds were obtained.

TABLE 10

| Example No. | *—Rᵃ | | MS (ESI m/z) (M + H) | RT (min) | ¹H-NMR(300 MHz) |
|---|---|---|---|---|---|
| 5-1 | [2-methylbenzo[d]thiazol-6-yl] | 6-(3-bromo-4-(pyrrolidin-1-yl)phenyl)-1-(2-methylbenzo[d]thiazol-6-yl)-4-oxo-1,4-dihydropyridine-3-carboxylic acid | 512 | 1.57 | (DMSO-D6) δ: 8.62 (1H, s), 8.28 (1H, d, J = 2.0 Hz), 7.90 (1H, d, J = 8.9 Hz), 7.47 (1H, dd, J = 8.8, 2.2 Hz), 7.41 (1H, d, J = 2.2 Hz), 7.07 (1H, dd, J = 8.8, 2.2 Hz), 6.84 (1H, s), 6.70 (1H, d, J = 8.9 Hz), 3.54-3.22 (4H, m), 2.81 (3H, s), 1.84-1.78 (4H, m). |

TABLE 10-continued

| Example No. | *—R$^a$ | | MS (ESI m/z) (M + H) | RT (min) | $^1$H-NMR(300 MHz) |
|---|---|---|---|---|---|
| 5-2 | [benzothiazole with morpholine] | 6-(3-bromo-4-(pyrrolidin-1-yl)phenyl)-1-(2-morpholinobenzo[d]thiazol-6-yl)-4-oxo-1,4-dihydropyridine-3-carboxylic acid | 583 | 1.59 | (CDCl3) : 8.67 (1H, s), 7.46 (1H, d, J = 8.6 Hz), 7.45 (1H, d, J = 2.3 Hz), 7.34 (1H, d, J = 2.3 Hz), 7.01 (1H, dd, J = 8.6, 2.3 Hz), 6.81 (1H, dd, J = 8.6, 2.3 Hz), 6.79 (1H, s), 6.53 (1H, d, J = 8.6 Hz), 3.87-3.82 (4H, m), 3.67-3.63 (4H, m), 3.44-3.38 (4H, m), 1.94-1.89 (4H, m). |
| 5-3 | [benzothiazole with bis(2-methoxyethyl)amino] | 1-(2-(bis(2-methoxyethyl)amino)benzo[d]thiazol-6-yl)-6-(3-bromo-4-(pyrrolidin-1-yl)phenyl)-4-oxo-1,4-dihydropyridine-3-carboxylic acid | 629 | 1.69 | (DMSO-D6) δ: 8.04 (1H, br s), 7.85 (1H, d, J = 2.0 Hz), 7.39 (1H, d, J = 2.0 Hz), 7.34 (1H, d, J = 8.6 Hz), 7.16-7.10 (1H, m), 7.01 (1H, dd, J = 8.6, 2.0 Hz), 6.73 (1H, d, J = 8.6 Hz), 6.20 (1H, br s), 3.75-3.67 (4H, m), 3.62-3.55 (4H, m), 3.41-3.21 (10H, m), 1.85-1.76 (4H, m). |
| 5-4 | [benzothiazole with 4-ethylpiperazine] | 6-(3-bromo-4-(pyrrolidin-1-yl)phenyl)-1-(2-(4-ethylpiperazin-1-yl)benzo[d]thiazol-6-yl)-4-oxo-1,4-dihydropyridine-3-carboxylic acid | 610 | 1.19 | (DMSO-D6) δ: 8.56 (1H, s), 8.02 (1H, s), 7.50-7.30 (3H, m), 7.09 (1H, dd, J = 8.6, 2.0 Hz), 6.85 (1H, s), 6.72 (1H, d, J = 8.6 Hz), 4.30-4.05 (2H, br m), 3.78-3.00 (12H, m), 1.82 (3H, t, J = 6.3 Hz), 1.30-1.08 (4H, m). |
| 5-5 | [benzothiazole with 4-(2-methoxyethyl)piperazine] | 6-(3-bromo-4-(pyrrolidin-1-yl)phenyl)-1-(2-(4-(2-methoxyethyl)piperazine-1-yl)benzo[d]thiazol-6-yl)-4-oxo-1,4-dihydropyridine-3-carboxylic acid | 640 | 1.21 | (MeOD) δ: 8.22 (1H, s), 7.67 (1H, s), 7.41-7.36 (2H, br m), 7.15 (1H, d, J = 9.2 Hz), 6.99 (1H, d, J = 9.2 Hz), 6.71 (1H, d, J = 8.6 Hz), 6.50 (1H, s), 3.65 (4H, br s), 3.57 (4H, br s), 3.35 (5H, br s), 2.69-2.62 (6H, br m), 1.92-1.86 (4H, br m). |

TABLE 10-continued

| Example No. | *—Rᵃ | | MS (ESI m/z) (M + H) | RT (min) | ¹H-NMR(300 MHz) |
|---|---|---|---|---|---|
| 5-6 | | (R)-6-(3-bromo-4-(pyrrolidin-1-yl)phenyl)-1-(2-(2-(methoxymethyl)pyrrolidin-1-yl)benzo[d]thiazol-6-yl)-4-oxo-1,4-dihydropyridine-3-carboxylic acid | 611 | 1.74 | (CDCl₃) δ: 8.66 (1H, s), 7.46 (1H, d, J = 8.6 Hz), 7.41 (1H, d, J = 2.6 Hz), 7.37 (1H, d, J = 2.0 Hz), 6.99 (1H, dd, J = 8.6, 2.0 Hz), 6.80 (1H, dd, J = 9.2, 2.6 Hz), 6.79 (1H, s), 6.53 (1H, d, J = 9.2 Hz), 3.65-3.49 (5H, m), 3.43-3.39 (4H, m), 3.39 (3H, s), 2.20-2.08 (4H, m), 1.94-1.89 (4H, m). |

Examples 6-1 to 6-5

In the same manner as in Examples 1-(1) and 1-(2), the following compounds were obtained.

TABLE 11

| Example No. | *—Rᵃ | | MS (ESI m/z) (M + H) | RT (min) | ¹H-NMR(300 MHz) |
|---|---|---|---|---|---|
| 6-1 | | 6-(3-chloro-4-(pyrrolidin-1-yl)phenyl)-1-(2-morpholinebenzo[d]thiazol-6-yl)-4-oxo-1,4-dihydropyridine-3-carboxylic acid | 537 | 1.57 | (CDCl3) δ: 8.67 (1H, s), 7.47-7.44 (2H, m), 7.11 (1H, d, J = 2.0 Hz), 7.01 (1H, dd, J = 8.6, 2.6 Hz), 6.79 (1H, s), 6.77 (1H, dd, J = 8.6, 2.0 Hz), 6.52 (1H, d, J = 8.6 Hz), 3.87-3.83 (4H, m), 3.67-3.63 (4H, m), 3.46-3.42 (4H, m), 1.94-1.89 (4H, m). |

TABLE 11-continued

| Example No. | *—Rᵃ | | MS (ESI m/z) (M + H) | RT (min) | ¹H-NMR(300 MHz) |
|---|---|---|---|---|---|
| 6-2 | | 1-2-(bis(2-methoxyethyl)amino)benzo[d]thiazol-6-yl)-6-(3-chloro-4-(pyrrolidin-1-yl)phenyl)-4-oxo-1,4-dihydropyridine-3-carboxylic acid | 583 | 1.67 | (CDCl3) δ: 8.65 (1H, s), 7.43-7.37 (2H, m), 7.15 (1H, d, J = 2.3 Hz), 6.98 (1H, dd, J = 8.6, 2.3 Hz), 6.78-6.73 (2H, m), 6.53 (1H, d, J = 9.2 Hz), 3.83-3.78 (4H, m), 3.70-3.65 (4H, m), 3.46-3.41 (4H, m), 3.37 (6H, s), 1.94-1.89 (4H, m). |
| 6-3 | | (R)-6-(3-chloro-4-(pyrrolidin-1-yl)phenyl)-1-(2-(2-(methoxymethyl)pyrrolidin-1-yl)benzo[d]thiazol-6-yl)-4-oxo-1,4-dihydropyridine-3-carboxylic acid | 565 | 1.73 | (CDCl3) δ: 8.66 (1H, s), 7.48-7.40 (2H, m), 7.13 (1H, d, J = 2.6 Hz), 6.99 (1H, dd, J = 8.6, 2.6 Hz), 6.79-6.74 (2H, m), 6.52 (1H, d, J = 8.6 Hz), 3.65-3.50 (5H, m), 3.45-3.41 (4H, m), 3.39 (3H, s), 2.19-2.05 (4H, m), 1.94-1.89 (4H, m). |
| 6-4 | | 6-(3-chloro-4-(pyrrolidin-1-yl)phenyl)-1-(2-(4-ethylpiperazin-1-yl)benzo[d]thiazol-6-yl)-4-oxo-1,4-dihydropyridine-3-carboxylic acid | 564 | 1.18 | (MeOD) δ: 8.71 (1H, br s), 7.77 (1H, br s), 7.50-7.43 (1H, br m), 7.28-7.17 (2H, br m), 7.02-6.94 (1H, br m), 6.83 (1H, br s), 6.71-6.64 (1H, br m), 3.81 (4H, br s), 3.63-3.51 (2H, br m), 3.38 (4H, br s), 3.04 (4H, br s), 1.90 (4H, br s), 1.26 (3H, br s). |
| 6-5 | | 6-(3-chloro-4-(pyrrolidin-1-yl)phenyl)-1-(2-(4-(2-methoxyethyl)piperazin-1-yl)benzo[d]thiazol-6-yl)-4-oxo-1,4-dihydropyridine-3-carboxylic acid | 594 | 1.11 | (MeOD) δ: 8.72 (1H, br s), 7.75 (1H, br s), 7.47-7.40 (1H, br m), 7.26-7.18 (2H, br m), 7.00-6.94 (1H, br m), 6.83 (1H, br s), 6.71-6.65 (1H, br m), 3.73 (4H, br s), 3.61 (2H, br s), 3.37 (7H, br s), 2.85 (6H, br s), 1.90 (4H, br s). |

Example 7
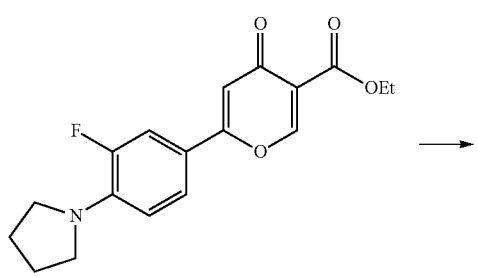
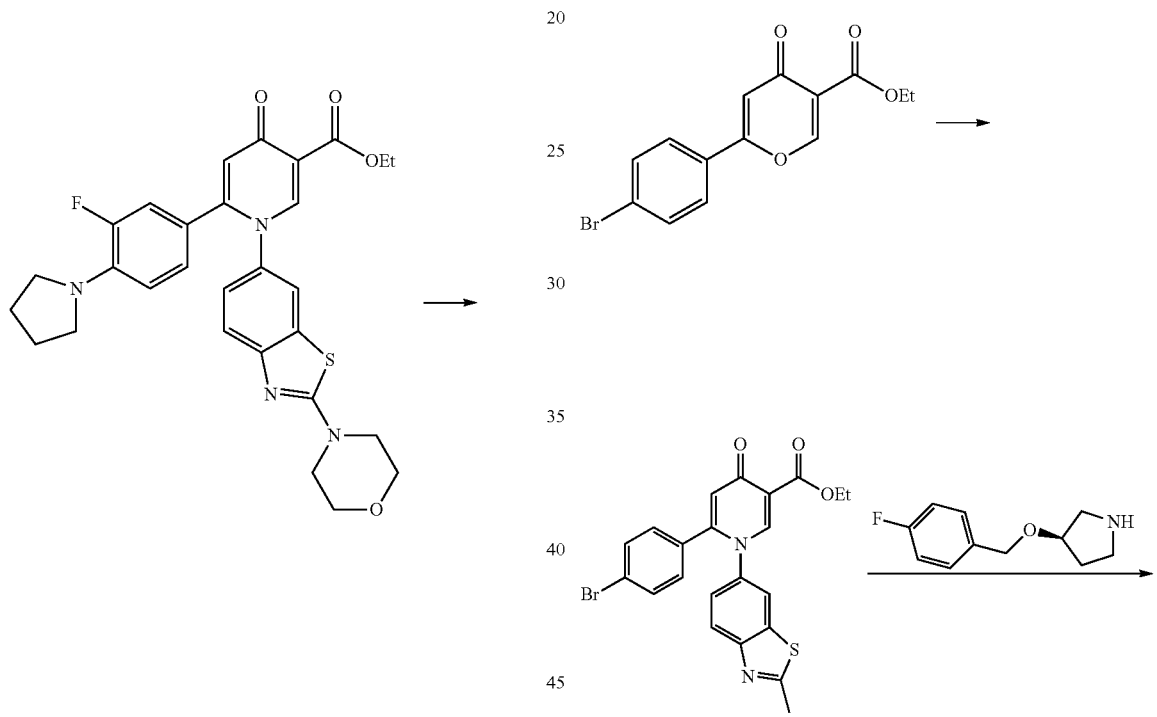
In the same manner as in Examples 1-(1) and 1-(2), the following compound was obtained.
6-(3-Fluoro-4-(pyrrolidin-1-yl)phenyl)-1-(2-morpholino-benzo[d]thiazol-6-yl)-4-oxo-1,4-dihydropyridine-3-carboxylic acid
$^1$H-NMR (CDCl$_3$) δ: 8.66 (1H, s), 7.46 (1H, d, J=2.0 Hz), 7.45 (1H, d, J=8.6 Hz), 7.00 (1H, dd, J=8.6, 2.0 Hz), 6.78 (1H, s), 6.76-6.69 (2H, m), 6.39 (1H, t, J=8.6 Hz), 3.90-3.79 (4H, m), 3.71-3.60 (4H, m), 3.44-3.32 (4H, m), 1.98-1.86 (4H, m).
MS (ESI m/z): 521 (M+H)
RT (min): 1.53
Example 8
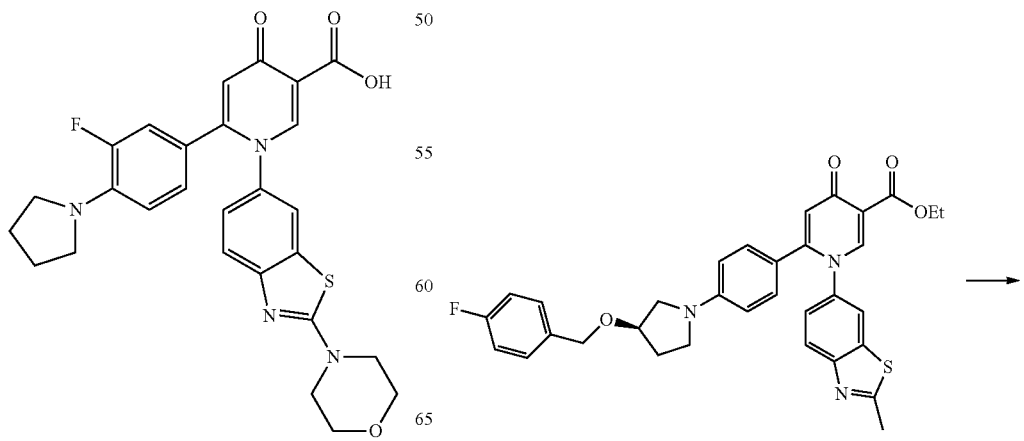

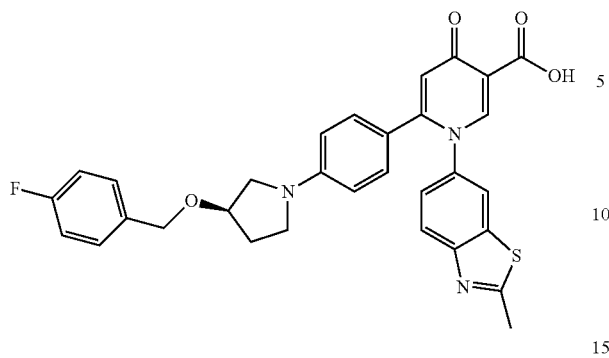

In the same manner as in Example 1-(1), the following compound was obtained.

Ethyl 6-(4-bromophenyl)-1-(2-methylbenzo[d]thiazol-6-yl)-4-oxo-1,4-dihydropyridine-3-carboxylate MS (ESI nm/z): 471 (M+H)

RT (min): 1.32

(2)

In the same manner as in Reference Example 7-(1), the following compound was obtained.

Ethyl (R)-6-(4-(3-((4-fluorobenzyl)oxy)pyrrolidin-1-yl)phenyl)-1-(2-methylbenzo[d]thiazol-6-yl)-4-oxo-1,4-dihydropyridine-3-carboxylate MS (ESI m/z): 584 (M+H)

RT (min): 1.61

(3)

In the same manner as in Example 1-(2), the following compound was obtained.

(R)-6-(4-(3-((4-Fluorobenzyl)oxy)pyrrolidin-1-yl)phenyl)-1-(2-m ethylbenzo[d]thiazol-6-yl)-4-oxo-1,4-dihydropyridine-3-carboxylic acid $^1$H-NMR (CDCl$_3$) δ: 8.68 (1H, s), 7.88 (1H, d, J=8.6 Hz), 7.70 (1H, d, J=2.0 Hz), 7.31-7.24 (2H, m), 7.16 (1H, dd, J=_=8.6, 2.0 Hz), 7.05-6.97 (2H, m), 6.94 (2H, d, J=8.6 Hz), 6.81 (1H, s), 6.31 (2H, d, J=8.6 Hz), 4.52 (1H, dd, J=11.2 Hz), 4.47 (1H, d, J=11.2 Hz), 4.32-4.20 (1H, m), 3.48-3.23 (4H, m), 2.87 (3H, s), 2.28-2.00 (2H, m).

MS (ESI m/z): 556 (M+H)

RT (min): 1.65

Example 9

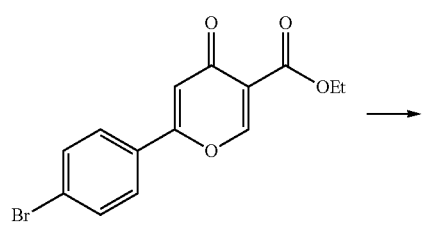

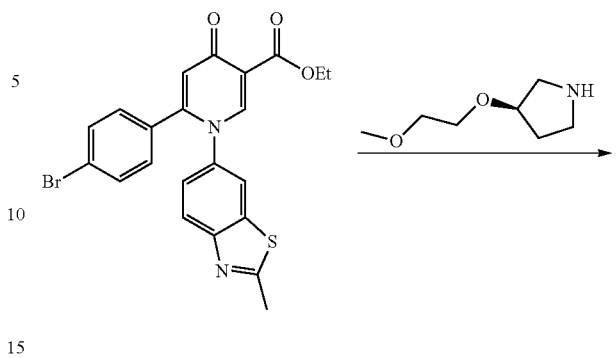

In the same manner as in Examples 8-(1), 8-(2), and 8-(3), the following compound was obtained.

(R)-6-(4-(3-(2-Methoxyethoxy)pyrrolidin-1-yl)phenyl)-1-(2-methylbenzo[d]thiazol-6-yl)-4-oxo-1,4-dihydropyridine-3-carboxylic acid $^1$H-NMR (CDCl$_3$) δ: 8.68 (1H, s), 7.88 (1H, d, J=8.6 Hz), 7.70 (11H, d, J=2.0 Hz), 7.16 (1H, dd, J=8.6, 2.0 Hz), 6.93 (2H, d, J=8.6 Hz), 6.81 (1H, s), 6.30 (21H, d, J=8.6 Hz), 4.26-4.16 (1H, m), 3.69-3.47 (4H, m), 3.47-3.33 (5H, nm), 3.33-3.21 (2H, m), 2.87 (3H, s), 2.26-1.97 (2H, m).

MS (ESI n/z): 506 (M+H)

RT (min): 1.28

Examples 10-1 to 10-4

In the same manner as in Examples 1-(1) and 1-(2), the following compounds were obtained.

TABLE 12

| Example No. | *—Rᵃ | | MS (ESI m/z) (M + H) | RT (min) | ¹H-NMR(300 MHz) |
|---|---|---|---|---|---|
| 10-1 | (benzothiazole with piperazine-N-CH₂CH₂OCH₃ substituent) | (R)-1-(2-(4-(2-methoxyethyl)piperazin-1-yl)benzo[d]thiazol-6-yl)-6-(4-(3-methoxypyrrolidin-1-yl)phenyl)-4-oxo-1,4-dihydropyridine-3-carboxylic acid | 590 | 1.02 | (DMSO-D6) δ: 8.14-8.10 (1H, m), 7.83 (1H, s), 7.34 (1H, d, J = 8.6 Hz), 7.14-7.04 (1H, m), 6.99 (2H, d, J = 8.6 Hz), 6.35 (2H, d, J = 8.6 Hz), 6.18 (1H, br s), 4.06-3.98 (1H, m), 3.57-3.12 (20H, m), 2.60-2.45 (2H, m), 2.05-1.95 (2H, m). |
| 10-2 | (benzothiazole with (R)-2-(methoxymethyl)pyrrolidinyl substituent) | 1-(2-((R)-2-(methoxymethyl)pyrrolidin-1-yl)benzo[d]thiazol-6-yl)-6-(4-((R)-3-methoxypyrrolidin-1-yl)phenyl)-4-oxo-1,4-dihydropyridine-3-carboxylic acid | 561 | 1.47 | (CDCl3) δ: 8.66 (1H, s), 7.44 (1H, d, J = 8.6 Hz), 7.41 (1H, d, J = 2.0 Hz), 6.98 (1H, cd, J = 8.6, 2.0 Hz), 6.96 (2H, d, J = 8.6 Hz), 6.79 (1H, s), 6.34 (2H, d, J = 8.6 Hz), 4.25-4.13 (1H, m), 4.11-4.03 (1H, m), 3.71-3.22 (14H, m), 2.25-1.96 (6H, m). |
| 10-3 | (benzothiazole with N,N-bis(2-methoxyethyl)amino substituent) | (R)-1-2-(bis(2-methoxyethyl)amino)benzo[d]thiazol-6-yl)-6-(4-(3-methoxypyrrolidin-1-yl)phenyl)-4-oxo-1,4-dihydropyridine-3-carboxylic acid | 579 | 1.41 | (CDCl3) δ: 8.65 (1H, s), 7.39 (1H, d, J = 8.6 Hz), 7.38 (1H, d, J = 2.0 Hz), 6.97 (1H, dd, J = 8.6, 2.0 Hz), 6.96 (2H, d, J = 8.6 Hz), 6.79 (1H, s), 6.35 (2H, d, J = 8.6 Hz), 4.12-4.03 (1H, m), 3.80 (4H, t, J = 5.3 Hz), 3.67 (4H, t, J = 5.3 Hz), 3.45-3.25 (13H, m), 2.22-1.95 (2H, m). |
| 10-4 | (benzothiazole with 4-ethylpiperazin-1-yl substituent) | (R)-1-(2-(4-ethylpiperazin-1-yl)benzo[d]thiazol-6-yl)-6-(4-(3-methoxypyrrolidin-1-yl)phenyl)-4-oxo-1,4-dihydropyridine-3-carboxylic acid | 560 | 0.95 | (CDCl3) δ: 8.66 (1H, s), 7.42 (1H, d, J = 8.6 Hz), 7.40 (1H, d, J = 2.0 Hz), 6.99 (1H, dd, J = 8.6, 2.0 Hz), 6.95 (2H, d, J = 9.2 Hz), 6.79 (1H, s), 6.33 (2H, d, J = 9.2 Hz), 4.11-4.02 (1H, m), 3.76-3.58 (4H, m), 3.44-3.22 (7H, m), 2.65-2.55 (4H, m), 2.50 (2H, q, J = 7.3 Hz), 2.23-1.95 (2H, m), 1.13 (3H, t, J = 7.3 Hz). |

Example 11

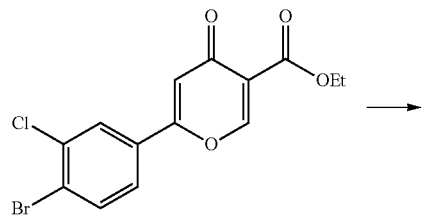

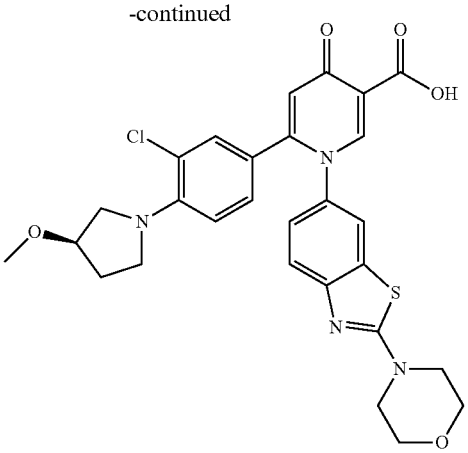

(1)

In the same manner as in Example 1-(1), the following compound was obtained.

Ethyl 6-(4-bromo-3-chlorophenyl)-1-(2-morpholinobenzo[d]thiazol-6-yl)-4-oxo-1,4-dihydropyridine-3-carboxylate MS (ESI m/z): 576 (M+H)

RT (min): 1.39

(2)

A mixture of ethyl 6-(4-bromo-3-chlorophenyl)-1-(2-morpholinobenzo[d]thiazol-6-yl)-4-oxo-1,4-dihydropyridine-3-carboxylate obtained in (1) (50 mg), chloro(2-dicyclohexylphosphino-2',6'-diisopropoxy-1,1'-biphenyl)[2-(2'-amino-1,1'-biphenyl)]palladium (II) (7 mg), cesium carbonate (113 mg), a 1,2-dimethoxyethane solution (2 mL) of (R)-3-methoxypyrrolidine obtained in Reference Example 13, and 1,2-dimethoxyethane (2 mL) was irradiated with microwaves (Initiator™, 120° C., 1 hour, 2.45 GHz, 0-240 W). The reaction mixture was cooled to room temperature and then the solvent was evaporated under reduced pressure. The obtained residue was purified by silica gel column chromatography [eluent; 50%-0% hexane/ethyl acetate→100%-75% ethyl acetate/methanol] to obtain ethyl (R)-6-(3-chloro-4-(3-methoxypyrrolidin-1-yl)phenyl)-1-(2-morpholinobenzo[d]thiazol-6-yl)-4-oxo-1,4-dihydropyridine-3-carboxylate (16.4 mg).

MS (ESI m/z): 595 (M+H)

RT (min): 1.35

(3)

In the same manner as in Example 1-(2), the following compound was obtained.

(R)-6-(3-Chloro-4-(3-methoxypyrrolidin-1-yl)phenyl)-1-(2-morpholinobenzo[d]thiazol-6-yl)-4-oxo-,4-dihydropyridine-3-carboxylic acid $^1$H-NMR (CDCl$_3$) δ: 8.67 (1H, s), 7.46 (1H, d, J=8.6 Hz), 7.43 (1H, d, J=2.0 Hz), 7.12 (1H, d, J=2.0 Hz), 7.02 (1H, dd, J=8.6, 2.0 Hz), 6.79 (1H, dd, J=8.6, 2.0 Hz), 6.78 (1H, s), 6.53 (1H, d, J=8.6 Hz), 4.05-3.97 (1H, m), 3.90-3.80 (4H, m), 3.75 (1H, dd, J=10.9, 5.0 Hz), 3.71-3.60 (4H, m), 3.59-3.48 (1H, m), 3.46-3.27 (5H, m), 2.15-1.91 (2H, m).

MS (ESI m/z): 567 (M+H)

RT (min): 1.42

Examples 12-1 to 1.2-4

In the same manner as in Examples 1-(1) and 1-(2), the following compounds were obtained.

TABLE 13

| Example No. | *R$^a$ | | MS (ESI m/z) (M + H) | RT (min) | $^1$H-NMR(300 MHz) |
|---|---|---|---|---|---|
| 12-1 | | (R)-1-(2-(bis(2-methoxyethyl)amino)benzo[d]thiazol-6-yl)-6-(3-chloro-4-(3-methoxypyrrolidin-1-yl)phenyl)-4-oxo-1,4-dihydropyridine-3-carboxylic acid | 613 | 1.52 | (CDCl3) δ: 8.65 (1H, s), 7.41 (1H, d, J = 8.6 Hz), 7.38 (1H, d, J = 2.0 Hz), 7.15 (1H, d, J = 2.0 Hz), 6.98 (1H, dd, J = 8.6, 2.0 Hz), 6.80-6.75 (2H, m), 6.54 (1H, d, J = 8.6 Hz), 4.03-3.99 (1H, m), 3.83-3.78 (4H, m), 3.77-3.72 (1H, m), 3.70-3.65 (4H, m), 3.60-3.51 (1H, m), 3.45-3.37 (2H, m), 3.36 (6H, s), 3.33 (3H, s), 2.10-1.96 (2H, m). |
| 12-2 | | (R)-6-(3-chloro-4-(3-methoxypyrrolidin-1-yl)phenyl)-1-(2-(4-(2-methoxyethyl)piperazin-1-yl)benzo[d]thiazol-6-yl)-4-oxo-1,4-dihydropyridine-3-carboxylic acid | 624 | 1.09 | (MeOD) δ: 8.70 (1H, br s), 7.77 (1H, br s), 7.51-7.44 (1H, br m), 7.29-7.18 (2H, br m), 7.03-6.97 (1H, br m), 6.83 (1H, br s), 6.71-6.65 (1H, br m), 4.02 (1H, br s), 3.86 (4H, br s), 3.73-3.66 (4H, br m), 3.55-3.48 (2H, br m), 3.41 (3H, br s), 3.26-3.15 (6H, br m), 2.01 (3H, br s), 1.29-1.21 (2H, br m). |
| 12-3 | | (R)-6-(3-chloro-4-(3-methoxypyrrolidin-1-yl)phenyl)-1-(2-(4-ethylpiperazin-1-yl)benzo[d]thiazol-6-yl)-4-oxo-1,4-dihydropyridine-3-carboxylic acid | 594 | 1.08 | (DMSO-D6) δ: 8.05 (1H, s), 7.85 (1H, d, J = 2.3 Hz), 7.36 (1H, d, J = 8.6 Hz), 7.20-7.11 (2H, m), 6.96 (1H, dd, J = 8.6, 2.0 Hz), 6.70 (1H, d, J = 8.9 Hz), 6.18 (1H, s), 4.00-3.93 (1H, m), 3.62-3.17 (15H, m), 2.38 (2H, q, J = 7.2 Hz), 1.99-1.87 (2H, m), 1.02 (3H, t, J = 7.2 Hz). |
| 12-4 | | 6-(3-chloro-4-((R)-3-methoxypyrrolidin-1-yl)phenyl)-1-(2-((R)-(2-methoxymethyl)pyrrolidin-1-yl)benzo[d]thiazol-6-yl)-4-oxo-1,4-dihydropyridine-3-carboxylic acid | 595 | 1.55 | (CDCl3) δ: 8.67 (1H, s), 7.46 (1H, d, J = 8.6 Hz), 7.40 (1H, d, J = 2.0 Hz), 7.14 (1H, d, J = 2.0 Hz), 6.99 (1H, dd, J = 8.6, 2.0 Hz), 6.79 (1H, dd, J = 8.6, 2.0 Hz), 6.78 (1H, s), 6.54 (1H, d, J = 8.6 Hz), 4.26-4.12 (1H, m), 4.05-3.96 (1H, m), 3.75 (1H, dd, J = 10.9, 5.0 Hz), 3.68-3.29 (13H, m), 2.25-1.92 (6H, m). |

Example 13

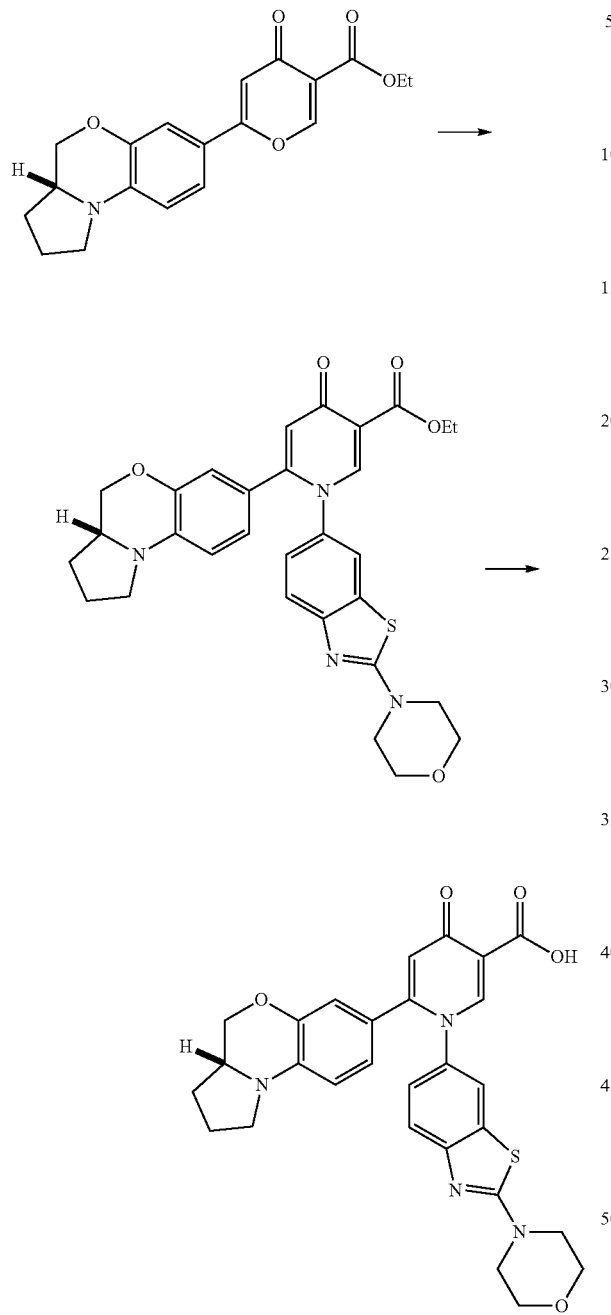

In the same manner as in Examples 1-(1) and 1-(2), the following compound was obtained.

(R)-1-(2-Morpholinobenzo[d]thiazol-6-yl)-4-oxo-6-(2,3,3a,4-tetrahydro-1H-benzo[b]pyrrolo[1,2-d][1,4]oxazin-7-yl)-1,4-dihydropyridine-3-carboxylic acid $^1$H-NMR (DMSO-D6) δ: 8.26 (1H, s), 7.90 (1H, s), 7.38 (1H, d, J=8.6 Hz), 7.21-7.10 (1H, br m), 6.69-6.60 (2H, m), 6.37 (2H, d, J=7.9 Hz), 4.42-4.35 (1H, m), 3.78-3.00 (12H, m), 2.10-1.80 (4H, m).

MS (ESI m/z): 531 (M+H)

RT (min): 1.39

Example 14

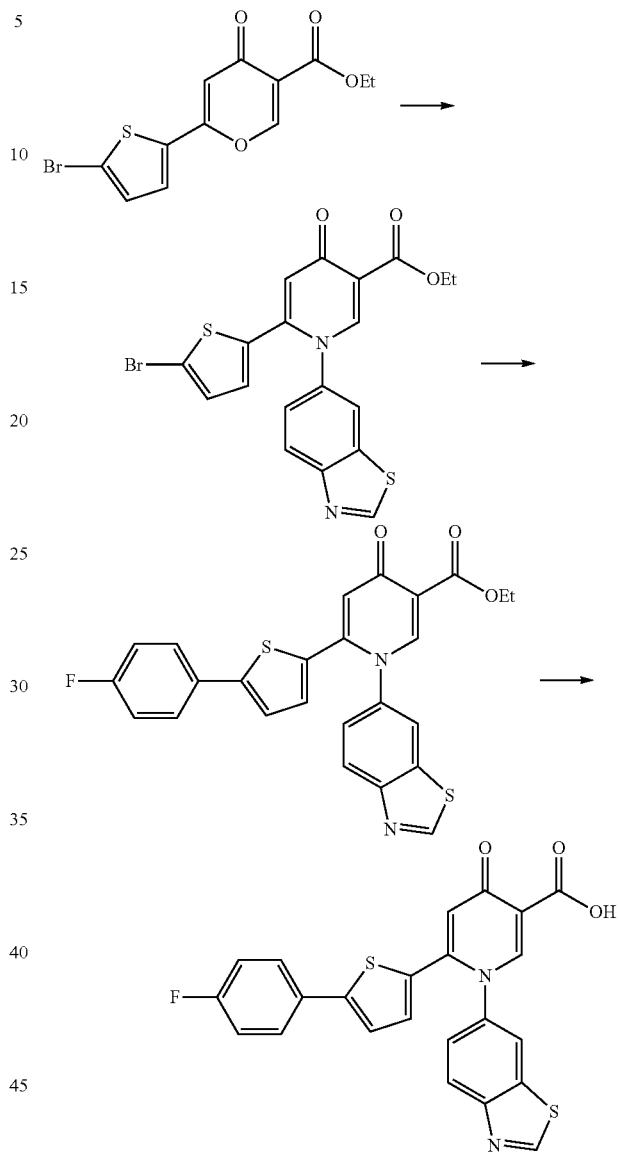

(1)

In the same manner as in Example 1-(1), the following compound was obtained.

Ethyl 1-(benzo[d]thiazol-6-yl)-6-(5-bromothiophen-2-yl)-4-oxo-1,4-dihydropyridine-3-carboxylate MS (ESI m/z): 461 (M+H)

RT (min): 1.21

(2)

A mixture of ethyl 1-(benzo[d]thiazol-6-yl)-6-(5-bromothiophen-2-yl)-4-oxo-1,4-dihydropyridine-3-carboxylate obtained in (1) (20 mg), (4-fluorophenyl)boronic acid (9.1 mg), tetrakis(triphenylphosphine)palladium (0) (5.0 mg), a 2 mol/L aqueous sodium carbonate solution (54.2 μL), and 1,2-dimethoxyethane (4 mL) was irradiated with microwaves (Initiator™, 120° C., 30 minutes, 2.45 GHz, 0-240 W). The reaction mixture was cooled to room temperature and then the solvent was evaporated under reduced pressure. The obtained residue was purified by silica gel column chromatography [eluent; 50%-0% hexane/ethyl acetate→100%-80% ethyl acetate/methanol] to obtain as a brown solid ethyl 1-(benzo[d]thiazol-6-yl)-6-(5-(4-fluorophenyl)thiophen-2-yl)-4-oxo-1,4-dihydropyridine-3-carboxylate (9.4 mg).

MS (ESI m/z): 477 (M+H)

RT (min): 1.37

(3)

In the same manner as in Example 1-(2), the following compound was obtained.

1-(Benzo[d]thiazol-6-yl)-6-(5-(4-fluorophenyl)thiophen-2-yl)-4-oxo-1,4-dihydropyridine-3-carboxylic acid $^1$H-NMR (CDCl$_3$) δ: 9.19 (1H, s), 8.69 (1H, s), 8.22 (1H, d, J=8.6 Hz), 8.00 (1H, d, J=2.0 Hz), 7.46-7.33 (31H, m), 7.09-6.96 (4H, m), 6.79 (1H, d, J=4.0 Hz).

MS (ESI m/z): 449 (M+H)

RT (min): 1.44

Example 15

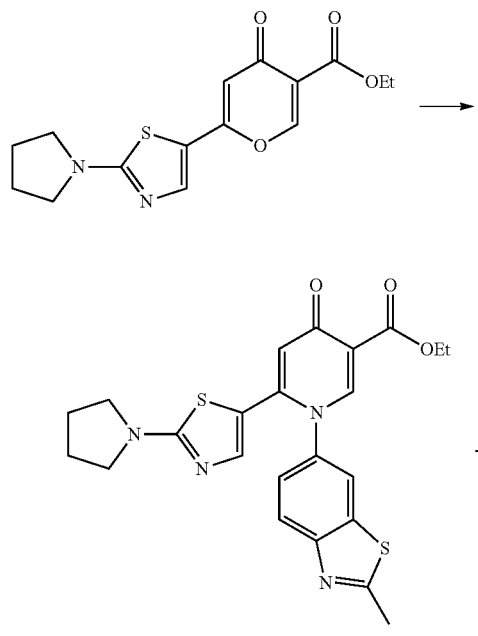

In the same manner as in Examples 1-(1) and 1-(2), the following compound was obtained.

1-(2-Methylbenzo[d]thiazol-6-yl)-4-oxo-6-(2-(pyrrolidin-1-yl)thiazol-5-yl)-1,4-dihydropyridine-3-carboxylic acid $^1$H-NMR (CDCl$_3$) δ: 8.56 (1H, s), 8.04 (1H, d, J=8.6 Hz), 7.84 (1H, d, J=2.0 Hz), 7.37 (1H, dd, J=8.6, 2.0 Hz), 6.87 (2H, s), 3.40-3.26 (4H, m), 2.91 (3H, s), 2.07-1.97 (4H, m).

MS (ESI m/z): 439 (M+H)

RT (min): 1.10

Example 16

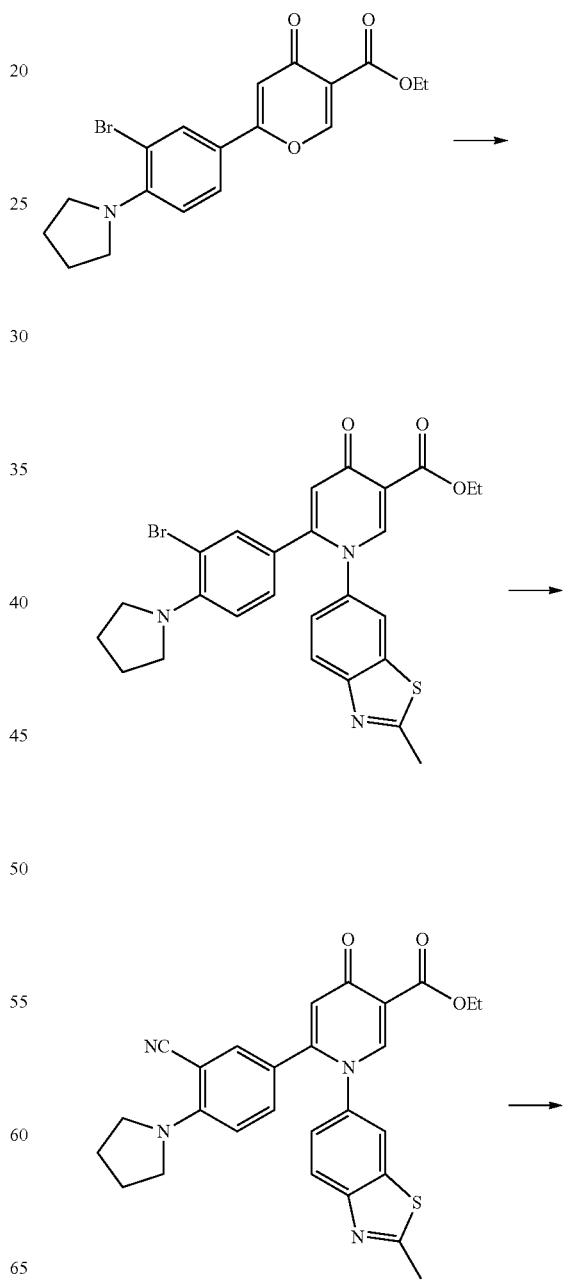

-continued

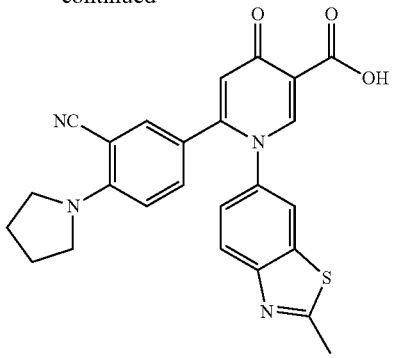

(1)
In the same manner as in Example 1-(1), the following compound was obtained.
Ethyl 6-(3-bromo-4-(pyrrolidin-1-yl)phenyl)-1-(2-methylbenzo[d]thiazol-6-yl)-4-oxo-1,4-dihydropyridine-3-carboxylate
MS (ESI m/z): 540 (M+H)
RT (min): 1.50
(2)
Ethyl 6-(3-bromo-4-(pyrrolidin-1-yl)phenyl)-1-(2-methylbenzo[d]thiazol-6-yl)-4-oxo-1,4-dihydropyridine-3-carboxylate obtained in (1) (200 mg), copper cyanide (I) (128 mg), and DMF (3 mL) were put into an Ace high pressure-resistant glass tube and stirred at 150° C. for 12 hours. The reaction mixture was cooled to room temperature, a saturated aqueous sodium hydrogen carbonate solution (9 mL) was added thereto, and the solid was collected by filtration. The obtained solid was purified by silica gel column chromatography [eluent; 100%-50% ethyl acetate/methanol] to obtain ethyl 6-(3-cyano-4-(pyrrolidin-1-yl)phenyl)-1-(2-methylbenzo[d]thiazol-6-yl)-4-oxo-1,4-dihydropyridine-3-carboxylate (150 mg) as a yellow solid.
MS (ESI m/z): 485 (M+H)
RT (min): 1.32
(3)
In the same manner as in Example 1-(2), the following compound was obtained.
6-(3-Cyano-4-(pyrrolidin-1-yl)phenyl)-1-(2-methylbenzo[d]thiazol-6-yl)-4-oxo-1,4-dihydropyridine-3-carboxylic acid
MS (ESI m/z): 457 (M+H)
RT (min): 1.34

Examples 17-1 to 17-5

In the same manner as in Examples 1-(1) and 1-(2), the following compounds were obtained.

TABLE 14

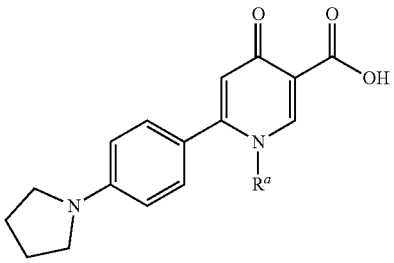

| Example No. | $R^a$ | | MS (ESI m/z) (M + H) | RT (min) | $^1$H-NMR(300 MHz) |
|---|---|---|---|---|---|
| 17-1 | * (structure) | (S)-1-(2-(3-(dimethylamino)pyrrolidin-1-yl)benzo[d]thiazol-6-yl)-4-oxo-6-(4-(pyrrolidin-1-yl)phenyl)-1,4-dihydropyridine-3-carboxylic acid | 530 | 1.05 | (CDCl3) δ: 8.66 (1H, s), 7.49-7.44 (2H, m), 7.00 (1H, dd, J = 8.6, 2.3 Hz), 6.94 (2H, d, J = 8.9 Hz), 6.80 (1H, s), 6.33 (2H, d, J = 8.9 Hz), 4.05-3.70 (3H, m), 3.66-3.55 (1H, m), 3.41-315 (5H, m), 2.70-2.38 (8H, m), 2.07-1.96 (4H, m). |
| 17-2 | * (structure) | (R)-1-(2-(3-(dimethylamino)pyrrolidin-1-yl)benzo[d]thiazol-6-yl)-4-oxo-6-(4-(pyrrolidin-1-yl)phenyl)-1,4-dihydropyridine-3-carboxylic acid | 530 | 1.04 | (CDCl3) δ: 8.66 (1H s), 7.49-7.44 (2H, m), 7.01 (1H dd, J = 8.6, 2.3 Hs), 6.94 (2H, d, J = 8.9 Hz), 6.80 (1H, s), 6.33 (2H, d, J = 8.9 Hz), 4.05-3.70 (3H, m), 3.66-3.55 (1H, m), 3.37 (1H, s), 3.27-3.18 (4H, m), 2.63 (6H, br s), 2.48-2.35 (2H, m), 2.01-1.95 (4H, m). |

TABLE 14-continued

| Example No. | Rᵃ | | MS (ESI m/z) (M + H) | RT (min) | ¹H-NMR(300 MHz) |
|---|---|---|---|---|---|
| 17-3 | [(S)-3-methoxypyrrolidin-1-yl benzothiazol-6-yl structure] | (S)-1-(2-(3-methoxypyrrolidin-1-yl)benzo[d]thiazol-6-yl)-4-oxo-6-(4-(pyrrolidin-1-yl)phenyl)-1,4-dihydropyridine-3-carboxylic acid | 517 | 1.47 | (CDCl3) δ: 8.66 (1H, s), 7.45 (1H, d, J = 8.7 Hz), 7.42 (1H, d, J = 2.3 Hz), 7.01-6.90 (3H, m), 6.78 (1H, s), 6.32 (2H, d, J = 8.7 Hz), 4.18-4.10 (1H, m), 3.75-3.58 (4H, m), 3.38 (3H, s), 3.26-3.18 (4H, m), 2.31-1.92 (6H, m). |
| 17-4 | [(R)-3-methoxypyrrolidin-1-yl benzothiazol-6-yl structure] | (R)-1-(2-(3-methoxypyrrolidin-1-yl)benzo[d]thiazol-6-yl)-4-oxo-6-(4-(pyrrolidin-1-yl)phenyl)-1,4-dihydropyridine-3-carboxylic acid | 517 | 1.47 | (CDCl3) δ: 8.66 (1H, s), 7.44 (1H, d, J = 8.7 Hz), 7.42 (1H, d, J = 2.3 Hz), 7.01-6.90 (3H, m), 6.79 (1H, s), 6.32 (2H, d, J = 8.7 Hz), 4.17-4.10 (1H, m), 3.75-3.58 (4H, m), 3.37 (3H, s), 3.26-3.18 (4H, m), 2.31-1.92 (6H, m). |
| 17-5 | [(3R,4R)-3,4-dimethoxypyrrolidin-1-yl benzothiazol-6-yl structure] | 1-(2-((3R,4R)-3,4-dimethoxypyrrolidin-1-yl)benzo[d]thiazol-6-yl)-4-oxo-6-(4-(pyrrolidin-1-yl)phenyl-1,4-dihydropyridine-3-carboxylic acid | 547 | 1.42 | (CDCl3) δ: 8.66 (1H, s), 7.46 (1H, d, J = 8.6 Hz), 7.43 (1H, d, J = 2.6 Hz), 7.00 (1H, dd, J = 8.6, 2.6 Hz), 6.94 (2H, d, J = 8.6 Hz), 6.79 (1H, s), 6.32 (2H, d, J = 8.6 Hz), 4.11-4.06 (2H, m), 3.79-3.68 (4H, m), 3.50 (6H, s), 3.26-3.19 (4H, m), 2.01-1.94 (4H, m). |

Examples 18-1 and 18-2

In the same manner as in Examples 1-(1) and 1-(2), the following compounds were obtained.

TABLE 15

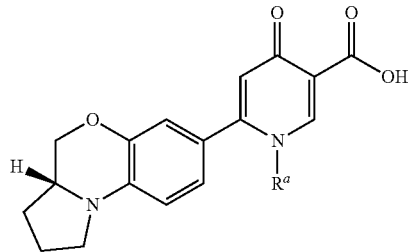

| Example No. | R$^a$ | | MS (ESI m/z) (M + H) | RT (min) | $^1$H-NMR(300 MHz) |
|---|---|---|---|---|---|
| 18-1 | * (structure) | 1-(2-((3R,4R)-3,4-dimethoxypyrrolidin-1-yl)benzo[d]thiazol-6-yl)-4-oxo-6-((S)-2,3,3a,benzo[b]pyrrolo[1,2-d][1,4]oxazin-7-yl)-1,4-dihydropyridine-3-carboxylic acid | 575 | 1.33 | (CDCl3) δ: 8.65 (1H, s), 7.46-7.38 (1H, m), 7.46 (1H, d, J = 8.6 Hz), 7.05-6.97 (1H, m), 6.78 (1H, s), 6.65 (1H, d, J = 2.0 Hz), 6.56 (1H, dd, J = 8.3, 2.0 Hz), 6.27 (1H, d, J = 8.3 Hz), 4.39 (1H, dd, J = 10.2, 3.3 Hz), 4.12-4.05 (2H, m), 3.80-3.10 (8H, m), 3.50 (6H, s), 2.14-1.88 (3H, m), 1.55-1.25 (1H, m). |
| 18-2 | * (structure) | (S)-1-(2-(3-methoxyazetidin-1-yl)benzo[d]thiazol-6-yl)-4-oxo-6-(2,3,3a,4-tetrahydro-1H-benzo[b]pyrrolo[1,2-d][1,4]oxazin-7-yl)-1,4-dihydropyridine-3-carboxylic acid | 531 | 1.37 | (CDCl3) δ: 8.64 (1H, s), 7.45 (1H, d, J = 8.8 Hz), 7.45-7.40 (1H, m), 7.00 (1H, dd, J = 8.8, 2.2 Hz), 6.78 (1H, s), 6.64 (1H, d, J = 2.1 Hz), 6.56 (1H, dd, J = 8.3, 2.1 Hz), 6.28 (1H, d, J = 8.3 Hz), 4.47-4.34 (4H, m), 4.11 (2H, dd, J = 9.1, 3.5 Hz), 3.60-3.10 (4H, m), 3.37 (3H, s), 2.17-1.89 (3H, m), 1.50-1.33 (1H, m). |

Examples 19-1 and 19-2

In the same manner as in Examples 1-(1) and 1-(2), the following compounds were obtained.

TABLE 16

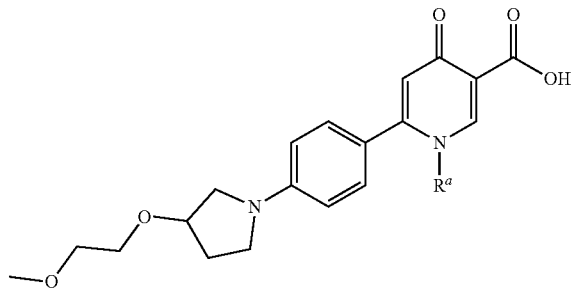

| Example No. | *—R<sup>a</sup> | | MS (ESI m/z) (M + H) | RT (min) | ¹H-NMR(300 MHz) |
|---|---|---|---|---|---|
| 19-1 | | (R)-6-(4-(3-(2-methoxyethoxy)pyrrolidin-1-yl)phenyl)-1-(2-morpholinobenzo[d]thiazol-6-yl)-4-oxo-1,4-dihydropyridine-3-carboxylic acid | 577 | 1.30 | (CDCl3) δ: 8.67 (1H, s), 7.47-7.41 (2H, m), 7.02 (1H, dd, J = 8.6, 2.0 Hz), 6.94 (2H, d, J = 8.6 Hz), 6.79 (1H, s), 6.31 (2H, d, J = 8.6 Hz), 4.26-4.20 (1H, br m), 3.87-3.82 (4H, m), 3.68-3.58 (6H, m), 3.53 (2H, q, J = 4.6 Hz), 3.45-3.35 (5H, m), 3.34-3.26 (2H, m), 2.20-2.02 (2H, m). |
| 19-2 | | 6-(4-((R)-3-(2-methoxyethoxy)pyrrolidin-1-yl)phenyl)-1-(2-((R)-2-(methoxymethyl)pyrrolidin-1-yl)benzo[d]thiazol-6-yl)-4-oxo-1,4-dihydropyridine-3-carboxylic acid | 605 | 1.44 | (CDCl3) δ: 8.66 (1H, s), 7.45 (1H, d, J = 8.6 Hz), 7.40 (1H, d, J = 2.0 Hz), 7.01-6.93 (3H, m), 6.79 (1H, s), 6.32 (2H, d, J = 8.6 Hz), 4.25-4.16 (2H, br m), 3.67-3.50 (9H, m), 3.46-3.40 (1H, m), 3.39 (3H, s), 3.37 (3H, s), 3.33-3.27 (2H, m), 2.20-2.03 (6H, m). |

Examples 20-1 and 20-2

In the same manner as in Examples 1-(1) and 1-(2), the following compounds were obtained.

TABLE 17

| Example No. | *—R^a | R^a | MS (ESI m/z) (M + H) | RT (min) | ¹H-NMR(300 MHz) |
|---|---|---|---|---|---|
| 20-1 | benzothiazole-morpholine | (R)-6-(3-fluoro-4-(3-methoxypyrrolidin-1-yl)phenyl)-1-(2-morpholinobenzo[d]thiazol-6-yl)-4-oxo-1,4-dihydropyridine-3-carboxylic acid | 551 | 1.37 | (CDCl$_3$) δ: 8.66 (1H, s), 7.46 (1H, d, J = 8.6 Hz), 7.43 (1H, d, J = 2.6 Hz), 7.02 (1H, dd, J = 8.6, 2.6 Hz), 6.78 (1H, s), 6.77-6.70 (2H, m), 6.40 (1H, t, J = 8.9 Hz), 4.05-3.97 (1H, m), 3.92-3.78 (4H, m), 3.73-3.30 (11H, m), 2.21-1.89 (2H, m). |
| 20-2 | benzothiazole-methoxyazetidine | (R)-6-(3-fluoro-4-(3-methoxypyrrolidin-1-yl)phenyl)-1-(2-(3-methoxyazetidin-1-yl)benzo[d]thiazol-yl)-4-oxo-1,4-dihydropyridine-3-carboxylic acid | 551 | 1.36 | (CDCl$_3$) δ: 8.65 (1H, s), 7.49 (1H, d, J = 8.6 Hz), 7.41 (1H, d, J = 2.6 Hz), 7.01 (1H, dd, J = 8.6, 2.6 Hz), 6.79-6.67 (3H, m), 6.39 (1H, t, J = 8.9 Hz), 4.51-4.33 (3H, m), 4.20-4.08 (2H, m), 4.05-3.96 (1H, m), 3.65-3.30 (10H, m), 2.19-1.88 (2H, m). |

Example 21

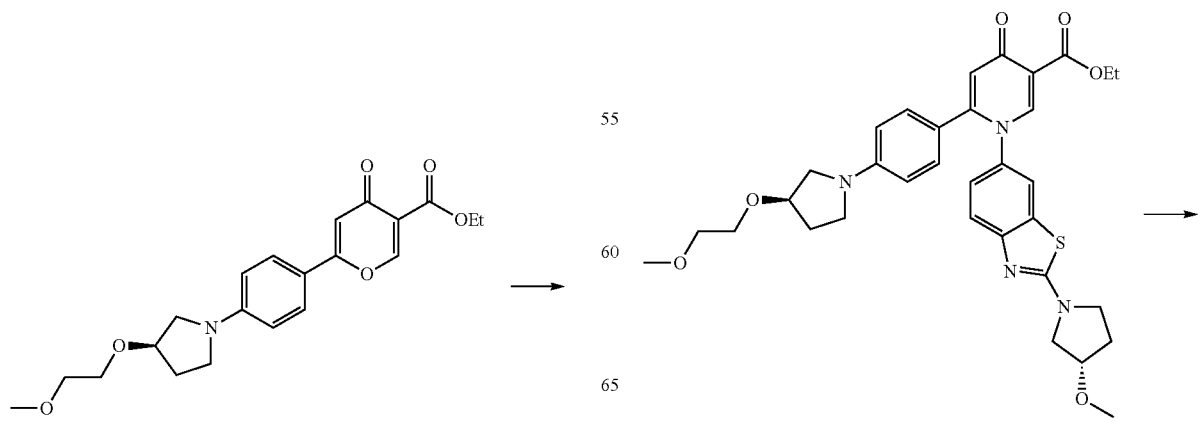

-continued

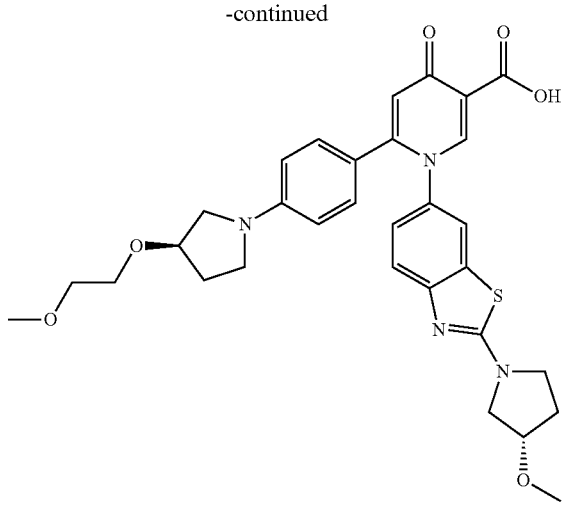

In the same manner as in Examples 1-(1) and 1-(2), the following compound was obtained.

6-(4-((R)-3-(2-Methoxyethoxy)pyrrolidin-1-yl)phenyl)-1-(2-((S)-3-methoxypyrrolidin-1-yl)benzo[d]thiazol-6-yl)-4-oxo-1,4-dihydropyridine-3-carboxylic acid $^1$H-NMR (CDCl$_3$) δ: 8.67 (1H, s), 7.46 (1H, d, J=8.6 Hz), 7.40 (1H, d, J=2.6 Hz), 6.99 (1H, dd, J=8.6, 2.6 Hz), 6.95 (21H, d, J=9.2 Hz), 6.79 (1H, s), 6.31 (2H, d, J=9.2 Hz), 4.25-4.18 (1H, m), 4.17-4.10 (1H, m), 3.73-3.25 (18H, m), 2.28-2.00 (4H, m).

MS (ESI m/z): 591 (M+H)

RT (min): 1.31

Examples 22-1 and 22-2

In the same manner as in Examples 1-(1) and 1-(2), the following compounds were obtained.

TABLE 18

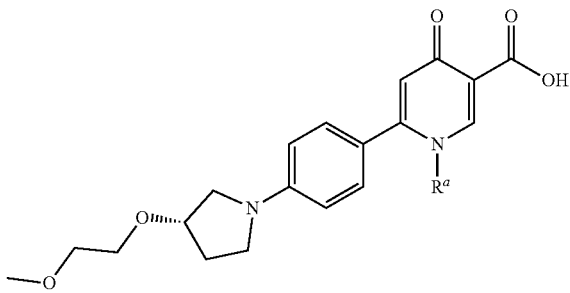

| Example No. | *—R$^a$ | | MS (ESI m/z) (M + H) | RT (min) | $^1$H-NMR(300 MHz) |
|---|---|---|---|---|---|
| 22-1 | (morpholino-benzothiazole structure) | (S)-6-(4-(3-(2-methoxyethoxy)pyrrolidin-1-yl)phenyl)-1-(2-morpholinobenzo[d]thiazol-6-yl)-4-oxo-1,4-dihydropyridine-3-carboxylic acid | 577 | 1.30 | (CDCl3) δ: 8.67 (1H, s), 7.47-7.41 (2H, m), 7.02 (1H, dd, J = 8.6, 2.0 Hz), 6.94 (2H, d, J = 9.2 Hz), 6.79 (1H, s), 6.31 (2H, d, J = 9.2 Hz), 4.25-4.19 (1H, m), 3.84 (4H, t, J = 4.6 Hz), 3.67-3.59 (6H, m), 3.56-3.50 (2H, m), 3.45-3.28 (7H, m), 2.20-2.03 (2H, m). |
| 22-2 | (methoxymethyl-pyrrolidinyl-benzothiazole structure) | 6-(4-((S)-3-(2-methoxyethoxy)pyrrolidin-1-yl)phenyl)-1-(2-((R)-2-(methoxymethyl)pyrrolidin-1-yl)benzo[d]thiazol-6-yl)-4-oxo-1,4-dihydropyridine-3-carboxylic acid | 605 | 1.44 | (CDCl3) δ: 8.66 (1H, s), 7.47-7.39 (2H, m), 7.00-6.91 (3H, m), 6.79 (1H, s), 6.32 (2H, d, J = 9.2 Hz), 4.26-4.15 (2H, m), 3.66-3.48 (8H, m), 3.45-3.24 (10H, m), 2.19-2.02 (6H, m). |

Examples 23-1 to 23-9

In the same manner as in Examples 1-(1) and 1-(2), the following compounds were obtained.

TABLE 19

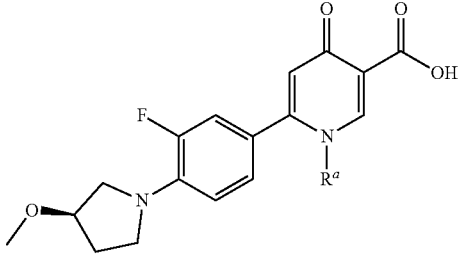

| Example No. | *—Rᵃ | | MS (ESI m/z) (M + H) | RT (min) | ¹H-NMR(300 MHz) |
|---|---|---|---|---|---|
| 23-1 | 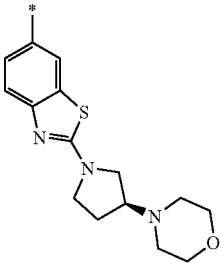 [SMILES: *c1ccc2nc(N3CC[C@H](N4CCOCC4)C3)sc2c1] | 6-(3-fluoro-4-((R)-3-methoxypyrrolidin-1-yl)phenyl)-1-(2-((S)-3-morpholinopyrrolidin-1-yl)benzo[d]thiazol-6-yl)-4-oxo-1,4-dihydropyridine-3-carboxylic acid | 620 | 1.03 | 1H-NMR (CDCl3) δ: 8.66 (1H, s), 7.46 (1H, t, J = 8.6 Hz), 7.41 (1H, d, J = 2.0 Hz), 7.00 (1H, dd, J = 8.6, 2.0 Hz), 6.79-6.70 (3H, m), 6.39 (1H, t, J = 8.9 Hz), 4.07-3.30 (13H, m), 3.15-3.03 (1H, m), 2.69-2.51 (5H, m), 2.35-2.30 (1H, m), 2.18-1.92 (5H, m). |
| 23-2 | 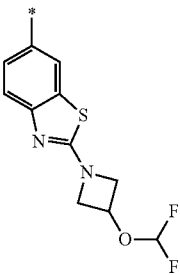 [SMILES: *c1ccc2nc(N3CC(OC(F)F)C3)sc2c1] | (R)-1-(2-(3-(difluoromethoxy)azetidin-1-yl)benzo[d]thiazol-6-yl)-6-(3-fluoro-4-(3-methoxypyrrolidin-1-yl)phenyl)-4-oxo-1,4-dihydropyridine-3-carboxylic acid | 587 | 1.47 | 1H-NMR (CDCl3) δ: 8.65 (1H, s), 7.51 (1H, t, J = 5.0 Hz), 7.43 (1H, d, J = 2.2 Hz), 7.03 (1H, dd, J = 8.7, 2.2 Hz), 6.79-6.69 (3H, m), 6.40 (1H, t, J = 8.7 Hz), 6.30 (1H, t, J = 72.5 Hz), 5.26-5.17 (1H, m), 4.55-4.48 (2H, m), 4.29 (2H, dd, J = 10.1, 4.3 Hz), 4.04-3.98 (1H, m), 362-3.34 (4H, m), 3.34 (3H, s), 2.15-2.06 (1H, m), 2.02-1.92 (1H, m). |
| 23-3 | 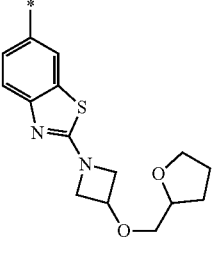 [SMILES: *c1ccc2nc(N3CC(OCC4CCCO4)C3)sc2c1] | 6-(3-fluoro-4-((R)-3-methoxypyrrolidin-1-yl)phenyl)-4-oxo-1-(2-(3-((tetrahydrofuran-2-yl)methoxy)azetidin-1-yl)benzo[d]thiazol-6-yl)-1,4-dihydropyridine-3-carboxylic acid | 621 | 1.42 | 1H-NMR (CDCl3) δ: 8.65 (1H, s), 7.47 (1H, d, J = 8.5 Hz), 7.40 (1H, d, J = 2.3 Hz), 7.00 (1H, dd, J = 8.5, 2.3 Hz), 6.78-6.69 (3H, m), 6.39 (1H, t, J = 9.0 Hz), 4.62-4.55 (1H, m), 4.42-4.35 (2H, m), 4.20-4.13 (2H, m), 4.09-3.98 (2H, m), 3.52-3.85 (1H, m), 3.83-3.75 (1H, m), 3.62-3.35 (6H, m), 3.33 (3H, s), 2.14-2.06 (1H, m), 2.04-1.85 (4H, m), 1.65-1.57 (1H, m). |
| 23-4 | 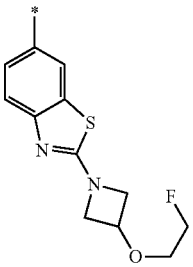 [SMILES: *c1ccc2nc(N3CC(OCCF)C3)sc2c1] | (R)-6-(3-fluoro-4-(3-methoxypyrrolidin-1-yl)phenyl)-1-(2-(3-fluoroethoxy)azetidin-1-yl)benzo[d]pyridin-6-yl)-4-oxo-1,4-dihydropyridine-3-carboxylic acid | 583 | 1.38 | 1H-NMR (CDCl3) δ: 8.65 (1H, s), 7.48 (1H, d, J = 8.7 Hz), 7.41 (1H, d, J = 2.2 Hz), 7.01 (1H, dd, J = 8.7, 2.2 Hz), 6.78-6.69 (3H, m), 6.39 (1H, t, J = 8.9 Hz), 4.67-4.57 (2H, m), 4.55-4.51 (1H, m), 4.45-4.38 (2H, m), 4.17 (2H, dd, J = 9.6, 4.2 Hz), 4.03-3.98 (1H, m), 3.80-3.75 (1H, m), 3.72-3.67 (1H, m), 3.62-3.34 (4H, m), 3.33 (3H, s), 2.14-2.06 (1H, m), 2.02-1.92 (1H, m). |

TABLE 19-continued

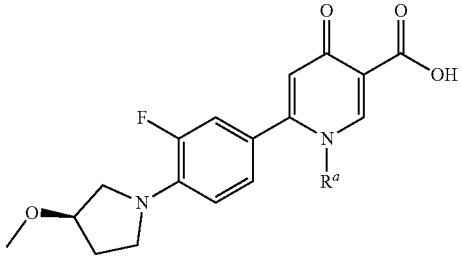

| Example No. | *R<sup>a</sup> | | MS (ESI m/z) (M + H) | RT (min) | ¹H-NMR(300 MHz) |
|---|---|---|---|---|---|
| 23-5 | 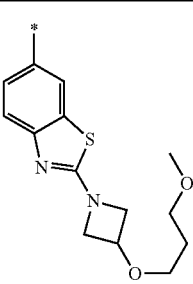 | (R)-6-(3-fluoro-4-(3-methoxypyrrolidin-1-yl)phenyl)-1-(2-(3-methoxypropoxy)azetidin-1-yl)benzo[d]pyridin-6-yl)-4-oxo-1,4-dihydropyridine-3-carboxylic acid | 609 | 1.43 | 1H-NMR (CDCl3) δ: 8.65 (1H, s), 7.48 (1H, d, J = 8.7 Hz), 7.41 (1H, d, J = 2.2 Hz), 7.00 (1H, dd, J = 8.7, 2.2 Hz), 6.78-6.59 (3H, m), 6.39 (1H, t, J = 9.0 Hz), 4.55-4.48 (1H, m), 4.42-4.35 (2H, m), 4.12 (2H, dd, J = 9.7, 4.1 Hz), 4.02-4.00 (1H, m), 3.62-3.35 (8H, m), 3.34 (3H, s), 3.33 (3H, s), 2.15-2.06 (1H, m), 2.03-1.92 (1H, m), 1.91-1.83 (2H, m). |
| 23-6 | 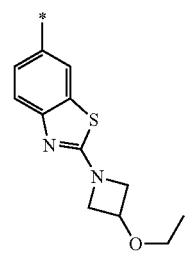 [SMILES: *c1ccc2nc(N3CC(OCC)C3)sc2c1] | (R)-1-(2-(3-ethoxyazetidin-1-yl)benzo[d]thiazol-6-yl)-6-(3-fluoro-4-(3-methoxypyrrolidin-1-yl)phenyl)-4-oxo-1,4-dihydropyridine-3-carboxylic acid | 565 | 1.45 | 1H-NMR (CDCl3) δ: 8.65 (1H, s), 7.47 (1H, d, J = 8.7 Hz), 7.41 (1H, d, J = 2.2 Hz), 7.00 (1H, dd, J = 8.7, 2.2 Hz), 6.78-6.59 (3H, m), 6.39 (1H, t, J = 8.9 Hz), 4.55-4.48 (1H, m), 4.42-4.35 (2H, m), 4.13 (2H, dd, J = 9.6, 4.2 Hz), 4.03-3.98 (1H, m), 3.62-3.56 (1H, m), 3.54-3.34 (5H, m), 3.33 (3H, s), 2.14-2.06 (1H, m), 2.02-1.92 (1H, m), 1.25 (3H, t, J = 7.0 Hz). |
| 23-7 | 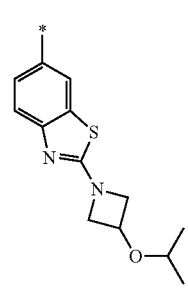 [SMILES: *c1ccc2nc(N3CC(OC(C)C)C3)sc2c1] | (R)-6-(3-fluoro-4-(3-methoxypyrrolidin-1-yl)phenyl)-1-(2-(3-isopropoxyazetidin-1-yl)benzo[d]thiazol-6-yl)-4-oxo-1,4-dihydropyridine-3-carboxylic acid | 579 | 1.54 | 1H-NMR (CDCl3) δ: 8.65 (1H, s), 7.47 (1H, d, J = 8.7 Hz), 7.40 (1H, d, J = 2.2 Hz), 7.00 (1H, dd, J = 8.6, 2.3 Hz), 6.79-6.69 (3H, m), 6.39 (1H, t, J = 9.0 Hz), 4.62-4.55 (1H, m), 4.44-4.36 (2H, m), 4.11 (2H, dd, J = 9.2, 4.6 Hz), 4.03-3.98 (1H, m), 3.72-3.34 (5H, m), 3.53 (3H, s), 2.14-2.06 (1H, m), 2.02-1.92 (1H, m), 1.19 (7H, d, J = 6.0 Hz). |
| 23-8 | 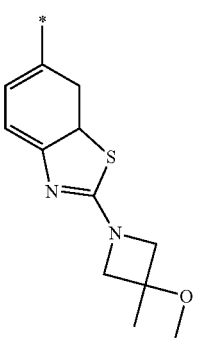 [SMILES: *C1=CC=C2N=C(N3CC(C)(OC)C3)SC2C1] | (R)-6-(3-fluoro-4-(3-methoxypyrrolidin-1-yl)phenyl)-1-(2-(3-methoxy-3-methylazetidin-1-yl)benzo[d]thiazol-6-yl)-4-oxo-1,4-dihydropyridine-3-carboxylic acid | 565 | 1.42 | 1H-NMR (CDCl3) δ: 8.65 (1H, s), 7.48 (1H, d, J = 8.7 Hz), 7.41 (1H, d, J = 2.2 Hz), 7.01 (1H, dd, J = 8.7, 2.2 Hz), 6.78-6.69 (3H, m), 6.39 (1H, t, J = 9.0 Hz), 4.20 (2H, d, J = 8.7 Hz), 4.03-3.96 (3H, m), 3.52-3.34 (3H, m), 3.33 (3H, s), 3.30 (3H, s), 2.14-2.07 (1H, m), 2.02-1.92 (2H, m), 1.59 (3H, s). |

TABLE 19-continued

| Example No. | *—Rᵃ | | MS (ESI m/z) (M + H) | RT (min) | ¹H-NMR(300 MHz) |
|---|---|---|---|---|---|
| 23-9 | (azetidine-benzothiazole structure) | (R)-6-(3-fluoro-4-(3-methoxypyrrolidin-1-yl)phenyl)-1-(2-(3-(2-methoxyethoxy)azetidin-1-yl)benzo[d]pyridin-6-yl)-4-oxo-1,4-dihydropyridine-3-carboxylic acid | 595 | 1.35 | 1H-NMR (CDCl3) δ: 8.65 (1H, s), 7.47 (1H, d, J = 8.7 Hz), 7.40 (1H, d, J = 2.2 Hz), 7 00 (1H, dd, J = 6.7, 2.2 Hz), 6.78-6.69 (3H, m), 6.39 (1H, t, J = 9.0 Hz), 4.61-4.54 (1H, m), 4.42-4.35 (2H, m), 4.17 (2H, dd, J = 9.7, 4.3 Hz), 4.03-3.98 (1H, m), 3.65-3.34 (11H, m), 3.33 (3H, s), 2.15-2.08 (1H, m), 2.02-1.92 (1H, m). |

Next, the usefulness of the representative compounds of the present invention will be described with reference to Test Examples.

Test Example 1

(Anti-HBV Assay)

Using HepG2.2.15 cells (Proc. Natl. Acad. Sci. USA, 84, 1005-1009, 1987) which have an HBV genome introduced into a hepatoblastoma cell line, HepG2, and persistently produce a virus, the anti-HBV activity of the representative compounds was evaluated in the following procedure.

The following was used as a medium:

DMEM/F-12, GlutaMAX (manufactured by Invitrogen)+5 μg/mL insulin (manufactured by Wako)+1% penicillin/streptomycin (manufactured by Sigma)+10 mmol/L HEPES (manufactured by Sigma)+50 μmol/L hydrocortisone (manufactured by Sigma)+10% FBS A mixture of a test compound with dimethyl sulfoxide (DMSO) was further added to the medium to obtain a final concentration of DMSO of 0.25% (v/v), and thus, test solutions containing the test compound at various concentrations were prepared. In addition, a test solution obtained by adding DMSO alone to the medium to obtain a final concentration of 0.25% (v/v) was prepared as a control without addition of a drug.

Test Example 1-1

(1) The HepG2.2.15 cells were suspended in the medium to prepare a. HepG2.2.15 cell suspension at 4×10⁵ cells/mL. The suspension was seeded in a 96-well microtiter plate (100 μL/well) and the plate was incubated in a 5% CO₂ incubator at 37° C. for 2 days.

(2) The culture supernatant was removed and the cells were washed twice with PBS (−) (100 μL/well).

(3) The test solution (200 μL/well) was added to the plate of (2) and the plate was incubated in a 5% CO₂ incubator at 37° C. for 4 days.

(4) The culture supernatant was removed, the test solution (200 μL/well) was added again to the plate, and the plate was incubated in a 5% CO₂ incubator at 37° C. for 3 days.

(5) The culture supernatant was collected and treated with a mixture of Buffer AL (manufactured by QIAGEN) and Proteinase K (manufactured by Invitrogen). The amount of DNA of HBV (HBV-DNA) in the obtained solution was absolutely quantified by a real-time PCR method. In addition, HBsAg (hepatitis B surface antigen) in the culture supernatant was absolutely quantified by chemiluminescent enzyme immunoassay using Lumipulse (registered trademark) HBsAg-HQ (manufactured by Fujirebio Inc.). The relative viral load (%) of a well with the compound added to a well without the compound added was calculated. An IC₅₀ of the compound was calculated using a FORECAST function (linear regression method) of Microsoft Office Excel 2007 by plotting the logarithm of the concentration against the relative viral load as a real number.

The IC₅₀ of HBV-DNA was defined as a concentration (or a logarithm dilution of the culture supernatant) of the compound, in which the amount of HBV-DNA is reduced by 50% as compared a control without the compound added.

In addition, the IC₅₀ of HBsAg was defined as a concentration (or a logarithm dilution of the culture supernatant) of the compound, in which the amount of HBsAg is reduced by 50% as compared a control without the compound added.

The results are shown in Table 20.

TABLE 20

| Example No. | IC₅₀ (μmol/L) | |
|---|---|---|
| | HBV-DNA | HBsAg |
| 1 | 0.12 | 0.12 |
| 3-1 | 0.027 | 0.021 |
| 3-2 | 0.0090 | 0.0031 |
| 3-3 | 0.0020 | 0.0050 |
| 3-4 | 0.0055 | 0.0059 |
| 3-5 | 0.0040 | 0.0080 |
| 3-6 | 0.0039 | 0.0030 |

TABLE 20-continued

| Example No. | IC$_{50}$ (μmol/L) | |
|---|---|---|
| | HBV-DNA | HBsAg |
| 3-9 | 0.0035 | 0.0060 |
| 3-10 | 0.0028 | 0.0013 |
| 3-12 | 0.0029 | 0.0024 |
| 3-13 | 0.0039 | 0.0051 |
| 4-1 | 0.018 | 0.018 |
| 4-2 | 0.0109 | 0.0053 |
| 5-1 | 0.0037 | 0.0064 |
| 5-2 | 0.0012 | 0.0016 |
| 6-1 | 0.010 | 0.0038 |
| 7 | 0.0014 | 0.0031 |
| 8 | 0.020 | 0.019 |
| 9 | 0.055 | 0.024 |
| 10-2 | 0.0052 | 0.0027 |
| 11 | 0.013 | 0.0049 |
| 14 | 0.10 | 0.091 |
| 16 | 0.018 | 0.015 |

Test Example 1-2

The test was performed by the same method as in Test Example 1-1 except that the amounts of the test solutions of (3) and (4) of Test Example 1-1 was changed to 100 μL/well. The results are shown in Table 21.

TABLE 21

| Example No. | IC$_{50}$ (μmol/L) | |
|---|---|---|
| | HBV-DNA | HBsAg |
| 21 | 0.0083 | 0.017 |
| 22-1 | 0.044 | 0.089 |
| 22-2 | 0.010 | 0.022 |
| 23-1 | 0.0017 | 0.0043 |
| 23-2 | 0.00096 | 0.0028 |
| 23-3 | 0.00061 | 0.0017 |
| 23-4 | 0.00088 | 0.0038 |
| 23-5 | 0.00050 | 0.0027 |
| 23-6 | 0.00045 | 0.0011 |
| 23-7 | 0.00065 | 0.0011 |
| 23-8 | 0.00089 | 0.0014 |
| 23-9 | 0.00068 | 0.0018 |

It was found that the representative compounds of the present invention reduce the amount of DNA of HBV. In addition, it was also found that the representative compounds inhibit HBsAg.

Test Example 2

(Anti-HBV Assay in PXB-Cells)

Using fresh human hepatocytes (PXB-cells, manufactured by PhenixBio Co., Ltd.) collected from a PXB mouse (a chimeric mouse with human hepatocytes), the anti-HBV activity of the representative compounds was evaluated in the following procedure.

The following was used as a medium:

DMEM (manufactured by Sigma)+0.25 μg/mL insulin (manufactured by Wako)+1% penicillin/streptomycin. (manufactured by Sigma)+20 mmol/L HEPES (manufactured by Sigma)+15 μg/mL L-proline (manufactured by Sigma)+50 nmol/L dexamethasone (manufactured by Sigma)+5 ng/mL EGF (manufactured by Peprotech)+0.1 mmol/L ascorbic acid 2-phosphate (manufactured by Wako)+10% FBS+2% DMSO Each of the test compounds) was further added to the medium to prepare a test solution containing each of the test compounds at various concentrations.

Test Example 2-1

(1) PXB-cells seeded at a seeding density of $2.1 \times 10^5$ cells/cm$^2$ in a 96-well microliter plate were incubated in a 5% $CO_2$ incubator at 37° C. until a day on which the cells were infected.

(2) HBV (genotype AeUS) derived from a PXB mouse serum was suspended in the medium containing 4% PEG-8000, and added to the plate of (1) at about 10 copies/cell such that the PXB cells were infected (100 μL/well), and the plate was incubated in a 5% $CO_2$ incubator at 37° C. for 1 day.

(3) The culture supernatant on day 1 post infection was removed and the cells were washed three times with DMEM containing 10% FBS and 1% penicillin/streptomycin. Then, the medium was added to the plate (100 μL/well) and the plate was incubated in a 5% $CO_2$ incubator at 37° C. for 1 day.

(4) The culture supernatant on day 2 post infection was removed and the cells were washed three times with DMEM containing 10% FBS and 1% penicillin/streptomycin. Then, the medium was added to the plate (100 μL/well) and the plate was incubated in a 5% $CO_2$ incubator at 37° C. for 5 days.

(5) The culture supernatant on day 7 post infection was removed, the medium was added to the plate (100 μL/well), and the plate was incubated in a 5% $CO_2$ incubator at 37° C. for 5 days.

(6) The culture supernatant on day 12 post infection was removed, the medium was added to the plate (100 μL/well), and the plate was incubated in a 5% $CO_2$ incubator at 37° C. for 5 days.

(7) The culture supernatant on day 17 post infection was removed, the test solution was added to the plate (100 μL/well), and the plate was incubated in a 5% $CO_2$ incubator at 37° C. for 5 days. As a control without the compound added, the medium was added to the plate (100 μL/well) and the plate was incubated in a 5% $CO_2$ incubator at 37° C. for 5 days.

(8) The culture supernatant on day 22 post infection was removed, the test solution was added to the plate (100 μL/well), and the plate was incubated in a 5% $CO_2$ incubator at 37° C. for 5 days. As a control without the compound added, the medium was added to the plate (100 μL/well) and the plate was incubated in a 5% $CO_2$ incubator at 37° C. for 5 days.

(9) The culture supernatant on day 27 post infection was removed, the test solution was added to the plate (100 μL/well), and the plate was incubated in a 5% $CO_2$ incubator at 37° C. for 5 days. As a control without the compound added, the medium was added to the plate (100 μL/well) and the plate was incubated in a 5% $CO_2$ incubator at 37° C. for 5 days.

(10) The culture supernatant on day 32 post infection was collected.

(11) The collected culture supernatant on day 32 post infection was purified with a QIAamp (registered trademark) DNA Blood Mini Kit (manufactured by QIAGEN). The amount of HBV-DNA in the obtained solution was absolutely quantified by a real-time PCR method. In addition, the amount of HBsAg in the culture supernatant was absolutely quantified by chemiluminescent enzyme immunoassay using Lumipulse (registered trademark) HBsAg-HQ (manufactured by Fujirebio Inc.). A relative viral load (%) with respect to a control without the compound added was each calculated. An $IC_{50}$ of the compound was calculated using a FORECAST function (linear regression method) of Microsoft Office Excel 2007 by plotting the logarithm of the concentration against the relative viral load as a real number.

The results are shown in Table 22.

TABLE 22

| Example No. | $IC_{50}$ (µmol/L) | |
|---|---|---|
| | HBV-DNA | HBsAg |
| 3-1 | 0.23 | 0.54 |
| 3-2 | 0.47 | 0.15 |
| 3-3 | 0.052 | 0.077 |
| 3-4 | 0.022 | 0.014 |
| 3-10 | 0.015 | 0.039 |
| 3-13 | <0.008 | 0.039 |
| 3-14 | 0.024 | 0.089 |
| 5-1 | 0.20 | 0.15 |
| 5-3 | 0.025 | 0.052 |
| 5-6 | 0.041 | 0.062 |
| 6-2 | 0.025 | 0.081 |
| 6-3 | 0.030 | 0.057 |
| 6-5 | <0.008 | 0.016 |
| 7 | 0.012 | 0.041 |
| 9 | 0.58 | 0.33 |
| 10-2 | 0.018 | 0.022 |
| 10-3 | 0.047 | 0.056 |
| 10-4 | 0.061 | 0.078 |
| 11 | 0.028 | 0.082 |
| 12-1 | <0.008 | 0.011 |
| 12-2 | 0.028 | 0.042 |
| 16 | 0.47 | 0.19 |

Test Example 2-2

(1) PXB-cells seeded at a seeding density of $2.1 \times 10^5$ cells/cm² in a 96-well microliter plate were incubated in a 5% $CO_2$ incubator at 37° C. until a day on which the cells were infected.

(2) A HBV (genotype CAT) prepared by transfecting an HBV plasmid into an HepG2 cell was suspended in the medium containing 4% PEG-8000, and added to the plate of (1) at about 30 copies/cell such that the PXB cells were infected (100 µL/well), and the plate was incubated in a 5% $CO_2$ incubator at 37° C. for 1 day.

(3) The culture supernatant on day 1 post infection was removed and the cells were washed three times with DMEM containing 10% FBS and 1% penicillin/streptomycin. Then, the medium was added to the plate (100 µL/well) and the plate was incubated in a 5% $CO_2$ incubator at 37° C. for 1 day.

(4) The culture supernatant on day 2 post infection was removed and the cells were washed three times with DMEM containing 10% FBS and 1% penicillin/streptomycin. Then, the medium was added to the plate (100 µL/well) and the plate was incubated in a 5% $CO_2$ incubator at 37° C. for 5 days.

(5) The culture supernatant on day 7 post infection was removed, the medium was added to the plate (100 µL/well), and the plate was incubated in a 5% $CO_2$ incubator at 37° C. for 5 days.

(6) The culture supernatant on day 12 post infection was removed, the medium was added to the plate (100 µL/well), and the plate was incubated in a 5% $CO_2$ incubator at 37° C. for 5 days.

(7) The culture supernatant on day 17 post infection was removed, the test solution was added to the plate (100 µL/well), and the plate was incubated in a 5% $CO_2$ incubator at 37° C. for 5 days. As a control without the compound added, the medium was added to the plate (100 µL/well) and the plate was incubated in a 5% $CO_2$ incubator at 37° C. for 5 days.

(8) The culture supernatant on day 22 post infection was removed, the test solution was added to the plate (100 µL/well), and the plate was incubated in a 5% $CO_2$ incubator at 37° C. for 5 days. As a control without the compound added, the medium was added to the plate (100 µL/well) and the plate was incubated in a 5% $CO_2$ incubator at 37° C. for 5 days.

(9) The culture supernatant on day 27 post infection was removed, the test solution was added to the plate (100 µL/well), and the plate was incubated in a 5% $CO_2$ incubator at 37° C. for 5 days. As a control without the compound added, the medium was added to the plate (100 µL/well) and the plate was incubated in a 5% $CO_2$ incubator at 37° C. for 5 days.

(10) The culture supernatant on day 32 post infection was collected.

(11) The collected culture supernatant on day 32 post infection was treated with a mixture of Buffer AL (manufactured by QIAGEN) and Proteinase K (manufactured by Invitrogen). The amount of HBV-DNA in the obtained solution was absolutely quantified by a real-time PCR method. In addition, the amount of HBsAg in the culture supernatant was absolutely quantified by chemiluminescent enzyme immunoassay using Lumipulse (registered trademark) HBsAg-HQ (manufactured by Fujirebio Inc.). A relative viral load (%) with respect to a control without the compound added was each calculated. An $IC_{50}$ of the compound was calculated using a FORECAST function (linear regression method) of Microsoft Office Excel 2007 by plotting the logarithm of the concentration against the relative viral load as a real number.

The representative compounds of the present invention (for example, the $IC_{50}$ in each of Examples 3-4, 17-1, 17-2, 17-3, 18-1, 18-2, 19-1, 19-2, 20-1, and 20-2) was less than 0.5 µmol/L for both of the amount of HBV-DNA, and HBsAg.

In addition, the $IC_{50}$ (HBV-DNA/HBsAg) of Example 6-5, 19-2 and 20-2 was each 0.076/0.061 µmol/L, 0.072/0.072 µmol/L, and 0.068/0.050 µmol/L.

Test Example 3

(In Vivo Efficacy Study in Chimeric Mouse with Human Hepatocytes)

Test Example 3-1

An in vivo efficacy study with a. PXB mouse (a chimeric mouse with human hepatocytes) was carried out in PhenixBio Co., Ltd. 27-Week-or-more-old male mice having body weights of 15 g or more after the elapse of 12 weeks from the infection with HBV genotype C were allocated into three groups (2 mice per group) and used.

The compounds of Examples 6-5 and 10-2 were each orally administered at 100 mg/kg twice a day for 14 days. The other group was taken as a control group for which administration was not carried out. A first administration day was taken as day 0, and before administration on day 0, day 3, Day 7, and day 10, and on day 14, the blood was collected from the orbital venous plexus under anesthesia with isoflurane. The serum was separated from the collected blood and purified with a QIAamp (registered trademark) DNA Blood Mini Kit (manufactured by QIAGEN). The amount of HBV-DNA in the obtained solution was absolutely quantified by a real-time PCR method. In addition, the amount of HBsAg and the amount of HBcrAg in the serum were each absolutely quantified by chemiluminescent enzyme immunoassay using Lumipulse (registered trademark) HBsAg-HQ (manufactured by Fujirebio Inc.) and Lumipulse (registered trademark) HBcrAg (manufactured by Fujirebio Inc.).

The results are shown in Table 23.

TABLE 23

| Group | Day 0 | Day 3 | Day 7 | Day 10 | Day 14 |
|---|---|---|---|---|---|
| HBV-DNA in serum (copies/mL) | | | | | |
| 6-5 | 2.3E+09 | 8.7E+08 | 2.7E+08 | 3.4E+08 | 3.3E+08 |
|  | 2.1E+09 | 7.1E+08 | 2.9E+08 | 6.3E+08 | 8.4E+08 |
| 10-2 | 1.5E+09 | 1.0E+09 | 6.9E+08 | 8.4E+08 | 9.6E+08 |
|  | 3.2E+09 | 1.4E+09 | 4.7E+08 | 6.4E+08 | 1.3E+09 |
| Control | 3.7E+09 | 3.7E+09 | 4.3E+09 | 3.4E+09 | 2.7E+09 |
|  | 3.2E+09 | 3.0E+09 | 2.6E+09 | 3.6E+09 | 2.4E+09 |
| HBsAg in serum (IU/mL) | | | | | |
| 6-5 | 3,578 | 781 | 570 | 588 | 540 |
|  | 2,370 | 357 | 345 | 355 | 349 |
| 10-2 | 2,930 | 638 | 450 | 476 | 522 |
|  | 2,629 | 564 | 429 | 407 | 477 |
| Control | 2,692 | 2,616 | 3,198 | 3,212 | 3,202 |
|  | 2,731 | 2,639 | 2,563 | 3,008 | 2,909 |

| Group | Day 0 | Day 3 | Day 7 | Day 14 |
|---|---|---|---|---|
| HBcrAg in serum (U/mL) | | | | |
| 6-5 | 4.5E+08 | 1.5E+08 | 8.7E+07 | 7.5E+07 |
|  | 2.9E+08 | 9.7E+07 | 7.7E+07 | 9.1E+07 |
| 10-2 | 2.7E+08 | 8.8E+07 | 7.5E+07 | 7.8E+07 |
|  | 4.1E+08 | 1.4E+08 | 7.3E+07 | 9.8E+07 |
| Control | 3.7E+08 | 4.8E+08 | 4.1E+08 | 3.7E+08 |
|  | 4.5E+08 | 4.3E+08 | 3.6E+08 | 4.3E+08 |

By administering the compound, the amounts of HBV-DNA, HBsAg, and HBcrAg in the serum decreased, and thus, the efficacy was confirmed even in the chimeric mouse with human hepatocytes.

Test Example 3-2

An in vivo efficacy study with a PXB mouse (a chimeric mouse with human hepatocytes) was carried out in PhenixBio Co., Ltd. 19-Week-or-more-old male mice having body weights of 10.5 g or more after the elapse of 13 weeks or more from the infection with HBV genotype C were allocated into the respective groups and used. The studies were carried out twice, and a 21-day administration withdrawal period was provided between the first study and the second study.

The first administration day in the first study was taken as day 0, and the compound of Example 6-5 was orally administered at 1 mg/kg, 3 mg/kg, 10 mg/kg, and 30 mg/kg twice a day, or 0.5% methylcellulose (vehicle) was orally administered once a day for 14 days. Before administration on day 0, day 3, Day 7, and day 10, and on day 14, the blood was collected from the orbital venous plexus under anesthesia with isoflurane.

The first administration day in the second study was taken as day 35, and the compounds of Examples 19-2 and 20-2 were each orally administered at 3 mg/kg twice a day, or 0.5% methylcellulose (vehicle) was orally administered once a day for 14 days. Before administration on day 35, day 38, day 42, and day 45, the blood was collected from the orbital venous plexus under anesthesia with isoflurane. On day 49, the blood was collected from the heart under anesthesia with isoflurane.

The serum was separated from the collected blood and purified with a QIAamp (registered trademark) DNA Blood Mini Kit (manufactured by QIAGEN). The amount of HBV-DNA in the obtained solution was absolutely quantified by a real-time PCR method. In addition, the amount of HBsAg in the serum was absolutely quantified by chemiluminescent enzyme immunoassay using Lumipulse (registered trademark) HBsAg-HQ (manufactured by Fujirebio Inc.).

The results are shown in Tables 24 and 25.

TABLE 24

Results of first study

| Group | Day 0 | Day 3 | Day 7 | Day 10 | Day 14 |
|---|---|---|---|---|---|
| HBV-DNA in blood (copies/mL) | | | | | |
| 30 mg/kg | 1.6E+09 | 8.3E+08 | 7.5E+08 | 8.0E+08 | 6.1E+08 |
|  | 1.2E+09 | 4.4E+08 | 3.7E+08 | 4.9E+08 | 2.6E+08 |
| 10 mg/kg | 1.1E+09 | 8.0E+08 | 3.3E+08 | 7.3E+08 | 4.9E+08 |
|  | 1.2E+09 | 4.5E+08 | 4.0E+08 | 3.9E+08 | 3.6E+08 |
| 3 mg/kg | 1.8E+09 | 5.7E+08 | 4.9E+08 | 5.7E+08 | 6.1E+08 |
|  | 9.8E+08 | 5.6E+08 | 4.0E+08 | 6.2E+08 | 5.2E+08 |
| 1 mg/kg | 8.4E+08 | 1.6E+09 | 1.4E+09 | 1.2E+09 | 6.8E+08 |
|  | 1.1E+09 | 7.7E+08 | 1.1E+09 | 1.2E+09 | 6.4E+08 |
| Vehicle | 1.3E+09 | 1.1E+09 | 1.3E+09 | 8.5E+08 | 1.2E+09 |
|  | 7.1E+08 | 7.6E+08 | 9.5E+08 | 1.1E+09 | 9.0E+08 |
| HBsAg in serum (IU/mL) | | | | | |
| 30 mg/kg | 2,291 | 673 | 458 | 359 | 408 |
|  | 2,328 | 592 | 370 | 392 | 268 |
| 10 mg/kg | 2,500 | 595 | 445 | 394 | 368 |
|  | 2,409 | 421 | 366 | 329 | 398 |
| 3 mg/kg | 2,722 | 972 | 859 | 959 | 1,012 |
|  | 2,314 | 1,059 | 876 | 1,025 | 837 |
| 1 mg/kg | 1,910 | 2,288 | 2,444 | 1,947 | 1,777 |
|  | 2,498 | 2,694 | 2,663 | 2,431 | 2,344 |
| Vehicle | 2,833 | 2,564 | 2,724 | 2,629 | 2,628 |
|  | 2,152 | 2,738 | 2,233 | 2,441 | 2,316 |

TABLE 25

Results of second study

| Group | Day 35 | Day 38 | Day 42 | Day 45 | Day 49 |
|---|---|---|---|---|---|
| HBV-DNA in blood (copies/mL) | | | | | |
| 19-2 | 6.1E+08 | 2.1E+08 | 3.3E+08 | 4.2E+08 | 1.4E+08 |
|  | 3.7E+08 | 6.2E+08 | 2.5E+08 | 3.0E+08 | 1.8E+08 |
| 20-2 | 8.2E+08 | 4.6E+08 | 2.6E+08 | 3.5E+08 | 2.3E+08 |
|  | 8.3E+08 | 4.0E+08 | 5.0E+08 | 3.1E+08 | 2.7E+08 |
| Medium | 4.2E+08 | 7.5E+08 | 6.8E+08 | 5.5E+08 | 5.4E+08 |
|  | 1.7E+08 | 4.3E+08 | 4.4E+08 | 3.3E+08 | 3.1E+08 |
| HBsAg in serum (IU/mL) | | | | | |
| 19-2 | 1,872 | 968 | 992 | 1,548 | 1,509 |
|  | 2,473 | 2,558 | 1,238 | 1,644 | 1,348 |
| 20-2 | 2,556 | 948 | 832 | 859 | 1,444 |
|  | 3,408 | 1,061 | 1,478 | 1,185 | 924 |
| Medium | 2,505 | 2,664 | 2,233 | 2,838 | 2,546 |
|  | 2,003 | 2,298 | 2,033 | 1,980 | 2,130 |

In the group of the compounds, a decrease in HBV-DNA and HBsAg in the serum was observed at 3 mg/kg twice a day.

Test Example 3-3

An in vivo efficacy study with a PXB mouse (a chimeric mouse with human hepatocytes) was carried out in PhenixBio Co., Ltd. Male mice having body weights of 15 g or more after the elapse of 8 weeks from the infection with HBV genotype C were allocated into the respective groups and used.

The compounds of Example 20-2 was orally administered at 2 mg/kg, 6 mg/kg, and 20 mg/kg once a day, and at 1 mg/kg, 3 mg/kg, and 10 mg/kg twice a day, or 0.5% methylcellulose (vehicle) was orally administered once a day for 14 days. A first administration day was taken as day 0, and before administration on day 0, day 3, Day 7, and day 10, and on day 14, the blood was collected from the orbital venous plexus under anesthesia with isoflurane.

The serum was separated from the collected blood and purified with a QIAamp (registered trademark) DNA Blood Mini Kit (manufactured by QIAGEN). The amount of HBV-DNA in the obtained solution was absolutely quantified by a real-time PCR method. In addition, the amount of HBsAg in the serum was absolutely quantified by chemiluminescent enzyme immunoassay using Lumnipulse (registered trademark) HBsAg-HQ (manufactured by Fujirebio Inc.).

The results are shown in Table 26.

TABLE 26

| Group | Day 0 | Day 3 | Day 7 | Day 10 | Day 14 |
|---|---|---|---|---|---|
| HBV-DNA in blood (copies/mL) | | | | | |
| 20 mg/kg Once a day | 2.3E+08 | 2.1E+08 | 1.6E+08 | 3.3E+08 | 2.1E+08 |
| | 4.6E+08 | 2.0E+08 | 1.4E+08 | 2.5E+08 | 2.9E+08 |
| | 2.8E+08 | 9.7E+07 | 8.2E+07 | 1.5E+08 | 1.6E+08 |
| 10 mg/kg Twice a day | 3.8E+08 | 1.7E+08 | 1.6E+08 | 1.7E+08 | 2.0E+08 |
| | 4.0E+08 | 2.5E+08 | 1.1E+08 | 2.7E+08 | 2.3E+08 |
| | 4.2E+08 | 2.7E+08 | 2.1E+08 | 1.5E+08 | 2.6E+08 |
| 6 mg/kg Once a day | 6.7E+08 | 3.8E+08 | 3.5E+08 | 3.8E+08 | 2.2E+08 |
| | 1.6E+08 | 2.0E+08 | 1.5E+08 | 2.2E+08 | 1.5E+08 |
| | 4.3E+08 | 1.7E+08 | 3.3E+08 | 1.5E+08 | 7.7E+08 |
| 3 mg/kg Twice a day | 3.4E+08 | 2.2E+08 | 2.8E+08 | 3.1E+08 | 3.7E+08 |
| | 3.8E+08 | 1.8E+08 | 1.2E+08 | 4.3E+08 | 3.4E+08 |
| | 4.6E+08 | 2.1E+08 | 1.8E+08 | 3.5E+08 | 3.6E+08 |
| 2 mg/kg Once a day | 4.5E+08 | 2.6E+08 | 1.7E+08 | 4.2E+08 | 2.7E+08 |
| | 4.7E+08 | 3.3E+08 | 3.1E+08 | 4.3E+08 | 4.3E+08 |
| | 4.4E+08 | 2.7E+08 | 5.3E+08 | 3.9E+08 | 3.5E+08 |
| 1 mg/kg Twice a day | 2.8E+08 | 1.7E+08 | 2.7E+08 | 2.6E+08 | 2.5E+08 |
| | 1.4E+08 | 1.2E+08 | 1.4E+08 | 1.4E+08 | 1.3E+08 |
| | 4.6E+08 | 3.7E+08 | 2.3E+08 | 3.7E+08 | 6.9E+08 |
| Medium | 4.5E+08 | 8.6E+08 | 8.0E+08 | 7.9E+08 | 6.7E+08 |
| | 6.7E+08 | 6.4E+08 | 7.8E+08 | 1.3E+09 | 8.4E+08 |
| | 5.1E+08 | 5.9E+08 | 5.9E+08 | 6.6E+08 | 4.2E+08 |
| HBsAg in serum (IU/mL) | | | | | |
| 20 mg/kg Once a day | 3,225 | 1,239 | 1,003 | 1,200 | 1,037 |
| | 3,886 | 1,019 | 877 | 1,104 | 1,159 |
| | 2,106 | 517 | 385 | 493 | 497 |
| 10 mg/kg Twice a day | 3,678 | 994 | 707 | 861 | 931 |
| | 2,545 | 735 | 547 | 593 | 620 |
| | 3,727 | 901 | 708 | 676 | 738 |
| 6 mg/kg Once a day | 3,883 | 3,331 | 3,453 | 2,920 | 2,569 |
| | 1,905 | 1,529 | 1,321 | 1,342 | 1,312 |
| | 3,703 | 2,004 | 2,025 | 1,100 | 1,879 |
| 3 mg/kg Twice a day | 2,582 | 1,034 | 1,275 | 1,017 | 1,051 |
| | 2,395 | 1,048 | 785 | 900 | 910 |
| | 3,879 | 1,801 | 1,286 | 1,379 | 1,375 |
| 2 mg/kg Once a day | 2,534 | 2,393 | 1,612 | 1,946 | 1,526 |
| | 2,701 | 1,918 | 2,211 | 1,609 | 2,321 |
| | 3,776 | 3,502 | 3,236 | 3,623 | 3,366 |
| 1 mg/kg Twice a day | 3,352 | 3,056 | 3,033 | 2,356 | 2,833 |
| | 2,640 | 2,193 | 1,691 | 1,694 | 2,077 |
| | 4,436 | 4,655 | 3,774 | 3,775 | 4,276 |

TABLE 26-continued

| Group | Day 0 | Day 3 | Day 7 | Day 10 | Day 14 |
|---|---|---|---|---|---|
| Medium | 4,808 | 4,625 | 5,792 | 5,827 | 5,708 |
| | 4,882 | 5,147 | 5,172 | 6,104 | 5,756 |
| | 5,019 | 5,084 | 5,491 | 5,629 | 5,650 |

Because the group to which the compound was administered at 3 mg/kg twice a day exhibited stronger anti-HBV activity than the group to which the compound was administered at 6 mg/kg once a day, it was considered that it is important to maintain a concentration of the compound in the blood for a long time for the efficacy of the present compound.

It was shown that the compounds of the present invention have excellent anti-HBV activity.

The compounds represented by General Formula [1] or a salt thereof exhibit excellent anti-HBV activity and are useful as an anti-hepatitis B virus agent.

What is claimed is:

1. A compound represented by General Formula [1] or a salt thereof:

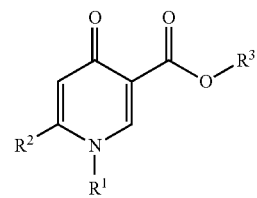

[1]

in the formula, $R^1$ represents a benzothiazolyl group which may be substituted (in which a carbon atom constituting the 6-membered ring of the benzothiazolyl group of $R^1$ is bonded to the nitrogen atom of the pyridone ring);

$R^2$ represents a $C_{2-6}$ alkenyl group which may be substituted, a $C_{2-6}$ alkynyl group which may be substituted, a $C_{3-8}$ cycloalkyl group which may be substituted, an aryl group which may be substituted, or a heterocyclic group which may be substituted; and $R^3$ represents a hydrogen atom or a carboxy-protecting group.

2. The compound or a salt thereof according to claim 1, wherein the compound is a compound represented by General Formula [1-1]:

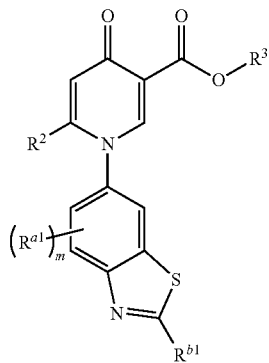

[1-1]

in the formula, $R^{a1}$'s are each independently the same as or different from each other, and represent a halogen atom, a cyano group, a nitro group, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, a carbamoyl group which may be substituted, a sulfamoyl group which may be substituted, or a carboxyl group which may be protected;

$R^{b1}$ represents a hydrogen atom, a halogen atom, a cyano group, a nitro group, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, an acylamino group which may be substituted, a carbamoyl group which may be substituted, a sulfamoyl group which may be substituted, a heterocyclic group which may be substituted, or a carboxyl group which may be protected;

$R^2$ represents a $C_{2-6}$ alkenyl group which may be substituted, a $C_{2-6}$ alkynyl group which may be substituted, a $C_{3-8}$ cycloalkyl group which may be substituted, an aryl group which may be substituted, or a heterocyclic group which may be substituted;

$R^3$ represents a hydrogen atom or a carboxy-protecting group; and m represents an integer of 0 to 3.

3. The compound or a salt thereof according to claim 2, wherein $R^{a1}$'s are each independently the same as or different from each other, and are each a halogen atom, a $C_{1-6}$ alkyl group which may be substituted, or a $C_{1-6}$ alkoxy group which may be substituted; and
m is an integer of 0 or 1.

4. The compound or a salt thereof according to claim 2, wherein $R^{b1}$ is a hydrogen atom, a halogen atom, a $C_{1-6}$ alkyl group which may be substituted, a $C_{1-6}$ alkoxy group which may be substituted, a $C_{1-6}$ alkylamino group which may be substituted, a di($C_{1-6}$ alkyl)amino group which may be substituted, or a heterocyclic group which may be substituted.

5. The compound or a salt thereof according to claim 1, wherein $R^2$ is a phenyl group which may be substituted, a thienyl group which may be substituted, a thiazolyl group which may be substituted, or a benzoxazinyl group which may be substituted.

6. The compound or a salt thereof according to claim 1, wherein $R^2$ is a phenyl group which may have one or more substituents selected from the substituent group A1, a thienyl group which may have one or more substituents selected from the substituent group $A_1$, a thiazolyl group which may have one or more substituents selected from the substituent group $A_1$, or a benzoxazinyl group represented by General Formula [2]:

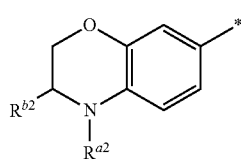

[2]

in the formula, $R^{a2}$ represents a hydrogen atom, a $C_{1-6}$ alkyl group which may be substituted, an acyl group which may be substituted, a $C_{1-6}$ alkylsulfonyl group which may be substituted, or an arylsulfonyl group which may be substituted;

$R^{b2}$ represents a hydrogen atom, a $C_{1-6}$ alkyl group which may be substituted, an aryl group which may be substituted, an acyl group which may be substituted, a carbamoyl group which may be substituted, a sulfamoyl group which may be substituted, a heterocyclic group which may be substituted, or a carboxyl group which may be protected; or $R^{a2}$ and $R^{b2}$ may be combined with an atom to which they are bonded to form a 5-membered heterocycle which may be substituted or a 6-membered heterocycle which may be substituted; and * represents a bonding position, in which the substituent group $A_1$ consists of groups represented by:
a halogen atom,
a cyano group,
a nitro group,
a $C_{1-6}$ alkyl group which may have one or more substituents selected from the substituent group $A_2$,
an aryl group which may have one or more substituents selected from the substituent group A2,
a $C_{1-6}$ alkoxy group which may have one or more substituents selected from the substituent group $A_2$,
a $C_{1-6}$ alkylamino group which may have one or more substituents selected from the substituent group $A_2$,
a di($C_{1-6}$ alkyl)amino group which may have one or more substituents selected from the substituent group $A_2$,
a carbamoyl group which may have one or more substituents selected from the substituent group $A_2$,
a sulfamoyl group which may have one or more substituents selected from the substituent group $A_2$,
a heterocyclic group which may have one or more substituents selected from the substituent group $A_2$, and
a carboxyl group which may be protected;
the substituent group $A_2$ consists of groups represented by:
a halogen atom,
a cyano group,
a nitro group,
a $C_{1-6}$ alkyl group which may have one or more substituents selected from the substituent group $A_3$,
an aryl group which may have one or more substituents selected from the substituent group $A_3$,
a $C_{1-6}$ alkoxy group which may have one or more substituents selected from the substituent group $A_3$,
a $C_{1-6}$ alkylamino group which may have one or more substituents selected from the substituent group $A_3$,
a di($C_{1-6}$ alkyl)amino group which may have one or more substituents selected from the substituent group $A_3$,
an acylamino group which may have one or more substituents selected from the substituent group $A_3$,
a carbamoyl group which may have one or more substituents selected from the substituent group $A_3$,
a sulfamoyl group which may have one or more substituents selected from the substituent group $A_3$,
a heterocyclic group which may have one or more substituents selected from the substituent group $A_3$, and
a carboxyl group which may be protected;
the substituent group $A_3$ consists of groups represented by:
a halogen atom,
a cyano group,
a nitro group, a $C_{1-6}$ alkyl group which may have one or more substituents selected from the substituent group $A_4$,
an aryl group which may have one or more substituents selected from the substituent group $A_4$,
a $C_{1-6}$ alkoxy group which may have one or more substituents selected from the substituent group $A_4$,
a $C_{1-6}$ alkylamino group which may have one or more substituents selected from the substituent group $A_4$,
a di($C_{1-6}$ alkyl)amino group which may have one or more substituents selected from the substituent group $A_4$,
a carbamoyl group which may have one or more substituents selected from the substituent group $A_4$,
a sulfamoyl group which may have one or more substituents selected from the substituent group $A_4$,
a heterocyclic group which may have one or more substituents selected from the substituent group $A_4$, and
a carboxyl group which may be protected; and
the substituent group $A_4$ consists of groups represented by:
a halogen atom,
a cyano group,
a nitro group,
a $C_{1-6}$ alkyl group,
an aryl group,
a $C_{1-6}$ alkoxy group,
a $C_{1-6}$ alkylamino group,
a di($C_{1-6}$ alkyl)amino group,
a carbamoyl group,
a sulfamoyl group,
a heterocyclic group, and
a carboxyl group.

7. The compound or a salt thereof according to claim 6, wherein the substituent group $A_1$ is:
a halogen atom,
a cyano group,
a $C_{1-6}$ alkyl group which may have one or more substituents selected from the substituent group $A_2$,
a $C_{1-6}$ alkoxy group which may have one or more substituents selected from the substituent group $A_2$,
a $C_{1-6}$ alkylamino group which may have one or more substituents selected from the substituent group $A_2$,
a di($C_{1-6}$ alkyl)amino group which may have one or more substituents selected from the substituent group $A_2$, or
a heterocyclic group which may have one or more substituents selected from the substituent group $A_2$;
the substituent group $A_2$ is:
a $C_{1-6}$ alkoxy group which may have one or more substituents selected from the substituent group $A_3$,
an acylamino group which may have one or more substituents selected from the substituent group $A_3$, or
a carbamoyl group which may have one or more substituents selected from the substituent group $A_3$;
the substituent group $A_3$ is:
a $C_{1-6}$ alkyl group which may have one or more substituents selected from the substituent group $A_4$,
an aryl group which may have one or more substituents selected from the substituent group $A_4$, or
a $C_{1-6}$ alkoxy group which may have one or more substituents selected from the substituent group $A_4$; and
the substituent group $A_4$ is:
a halogen atom,
a cyano group, or
a $C_{1-6}$ alkyl group.

8. The compound or a salt thereof according to claim 6, wherein the substituent group $A_1$ is:
a halogen atom,
a cyano group,
a nitro group,
a $C_{1-6}$ alkyl group which may have one or more substituents selected from the substituent group $A_2$,
an aryl group which may have one or more substituents selected from the substituent group $A_2$,
a $C_{1-6}$ alkoxy group which may have one or more substituents selected from the substituent group $A_2$,
a $C_{1-6}$ alkylamino group which may have one or more substituents selected from the substituent group $A_2$,
a di($C_{1-6}$ alkyl)amino group which may have one or more substituents selected from the substituent group $A_2$,
a carbamoyl group which may have one or more substituents selected from the substituent group $A_2$,
a sulfamoyl group which may have one or more substituents selected from the substituent group $A_2$,
a heterocyclic group which may have one or more substituents selected from the substituent group $A_2$, or
a carboxyl group which may be protected; and
the substituent group $A_2$ is:
a halogen atom,
a cyano group,
a nitro group,
a $C_{1-6}$ alkyl group,
an aryl group,
a $C_{1-6}$ alkoxy group,
a $C_{1-6}$ alkylamino group,
a di($C_{1-6}$ alkyl)amino group,
a carbamoyl group,
a sulfamoyl group,
a heterocyclic group, or
a carboxyl group.

9. The compound or a salt thereof according to claim 6, wherein the substituent group $A_1$ is:
a halogen atom,
a cyano group,
a nitro group,
a $C_{1-6}$ alkyl group,
an aryl group,
a $C_{1-6}$ alkoxy group,
a $C_{1-6}$ alkylamino group,
a di($C_{1-6}$ alkyl)amino group,
a carbamoyl group,
a sulfamoyl group,
a heterocyclic group, or
a carboxyl group.

10. The compound or a salt thereof according to claim 6, wherein $R^{a2}$ is a hydrogen atom or a $C_{1-6}$ alkyl group which may be substituted;
$R^{b2}$ is a hydrogen atom; or
$R^{a2}$ and $R^{b2}$ may be combined with an atom to which they are bonded to form a 5-membered heterocycle which may be substituted.

11. A pharmaceutical composition comprising:
the compound or a salt thereof according to claim 1.

12. A method for suppressing hepatitis B virus comprising:
administering the compound or a salt thereof according to claim 1 to a subject.

13. A method for inhibiting production of DNA of a hepatitis B virus comprising:
administering the compound or a salt thereof according to claim 1 to a subject.

14. A method for inhibiting production or secretion of a hepatitis B surface antigen comprising:
   administering the compound or a salt thereof according to claim 1 to a subject.

15. A method for treating or preventing HBV infection, comprising:
   administering the compound or a salt thereof as described in claim 1 to a subject.

16. A method for inhibiting the production or secretion of HBsAg, comprising:
   administering the compound or a salt thereof as described in claim 1 to a subject.

* * * * *